US007829572B2

(12) United States Patent
Didiuk et al.

(10) Patent No.: US 7,829,572 B2
(45) Date of Patent: Nov. 9, 2010

(54) PYRIDO[4,3-D]PYRIMIDIN-4(3H)-ONE DERIVATIVES AS CALCIUM RECEPTOR ANTAGONISTS

(75) Inventors: Mary T. Didiuk, Madison, CT (US); Kevin K. Liu, East Lyme, CT (US); David A. Griffith, Old Saybrook, CT (US); Angel Guzman-Perez, Mystic, CT (US); Feng C. Bi, Groton, CT (US); Daniel P. Walker, Chesterfield, MO (US)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 11/867,255

(22) Filed: Oct. 4, 2007

(65) Prior Publication Data
US 2008/0085887 A1   Apr. 10, 2008

Related U.S. Application Data

(60) Provisional application No. 60/828,162, filed on Oct. 4, 2006, provisional application No. 60/969,083, filed on Aug. 30, 2007.

(51) Int. Cl.
C07D 471/00 (2006.01)
A61K 31/519 (2006.01)
A61P 3/14 (2006.01)
A61P 19/02 (2006.01)

(52) U.S. Cl. .................................. 514/264.1; 544/279
(58) Field of Classification Search .............. 514/264.1; 544/279
See application file for complete search history.

(56) References Cited

U.S. PATENT DOCUMENTS

| 4,140,789 A | 2/1979 | Jaeggi et al. ........... 424/248.55 |
| 4,343,940 A | 8/1982 | Kreighbaum et al. ....... 544/283 |
| 4,379,788 A | 4/1983 | Heider et al. ............... 424/251 |
| 4,422,711 A | 12/1983 | Wolowicz ................... 339/252 |
| 4,431,440 A | 2/1984 | Bhalla et al. .................. 71/92 |
| 4,588,812 A | 5/1986 | Saeva et al. ................. 544/250 |
| 4,731,106 A | 3/1988 | Green et al. ................... 71/92 |
| 4,994,495 A | 2/1991 | Clough et al. ............... 514/574 |
| 4,999,381 A | 3/1991 | Crowley et al. ............. 514/618 |
| 5,055,471 A | 10/1991 | de Fraine et al. ........... 514/459 |
| 5,100,886 A | 3/1992 | Seaman et al. .............. 514/188 |
| 5,124,329 A | 6/1992 | Clough et al. ............... 514/241 |
| 5,126,338 A | 6/1992 | Worthington et al. ....... 514/210 |
| 5,145,856 A | 9/1992 | Clough et al. ............... 514/274 |
| 5,147,875 A | 9/1992 | Coates et al. ............... 514/259 |
| 5,153,199 A | 10/1992 | Baker et al. ................. 514/255 |
| 5,158,953 A | 10/1992 | Chern et al. ................ 514/267 |
| 5,162,325 A | 11/1992 | Chakravarty et al. ........ 514/259 |
| 5,185,339 A | 2/1993 | Pilkington et al. .......... 514/256 |
| 5,206,245 A | 4/1993 | Clough et al. ............... 514/269 |
| 5,236,927 A | 8/1993 | Jones et al. ................. 514/259 |
| 5,238,956 A | 8/1993 | Clough et al. ............... 514/506 |
| 5,240,928 A | 8/1993 | Allen et al. ................. 514/259 |
| 5,252,574 A | 10/1993 | Allen et al. ................. 514/259 |
| 5,260,326 A | 11/1993 | Sauter et al. ................ 514/383 |
| 5,264,439 A | 11/1993 | Greenlee et al. ............ 514/259 |
| 5,290,780 A | 3/1994 | Venkatesan et al. ......... 514/259 |
| 5,304,565 A | 4/1994 | Morimoto et al. ........... 514/340 |
| 5,334,722 A | 8/1994 | Crowley et al. ............. 546/289 |
| 5,385,894 A | 1/1995 | de Laszlo et al. ............. 514/80 |
| 5,401,745 A | 3/1995 | Bagley et al. ............... 514/259 |
| 5,409,930 A | 4/1995 | Spada et al. ................ 514/248 |
| 5,420,133 A | 5/1995 | Dhanoa et al. .............. 514/256 |
| 5,439,910 A | 8/1995 | deFraine et al. ............. 514/256 |
| 5,466,693 A | 11/1995 | Warrington et al. ......... 514/269 |
| 5,476,868 A | 12/1995 | Wingert et al. ............. 514/383 |
| 5,482,941 A | 1/1996 | Terrett ....................... 514/253 |
| 5,710,346 A | 1/1998 | Takahashi et al. ........... 568/723 |
| 5,719,098 A | 2/1998 | Hahn et al. ................. 502/407 |
| 5,721,238 A | 2/1998 | Heiker et al. ............... 514/259 |
| 5,753,651 A | 5/1998 | dePadova .................. 514/223.5 |

(Continued)

FOREIGN PATENT DOCUMENTS

BE   1003002   10/1994

(Continued)

OTHER PUBLICATIONS

Google Health, Rheumatoid Arthritis, 2010, https://health.google.com/health/ref/Rheumatoid+arthritis, downloaded May 6, 2010.*

(Continued)

*Primary Examiner*—James O Wilson
*Assistant Examiner*—Cecilia M Jaisle
(74) *Attorney, Agent, or Firm*—Jennifer A. Kispert; John A. Wichtowski

(57) ABSTRACT

The present invention is directed to novel pyrido[4,3-d]pyrimidin-4(3H)-one derivatives and pharmaceutically acceptable salts thereof of structural formula I

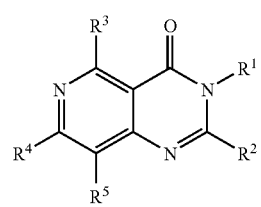

wherein the variables $R^1$, $R^2$, $R^3$, $R^4$ and $R^5$ are as described herein. Also provided are pharmaceutical compositions comprising the compounds of formula I as well as methods of treatment employing compounds of formula I to treat a disease or disorder characterized by abnormal bone or mineral homeostasis such as hypoparathyroidism, osteoporosis, osteopenia, periodontal disease, Paget's disease, bone fracture, osteoarthritis, rheumatoid arthritis, and humoral hypercalcemia of malignancy.

22 Claims, 1 Drawing Sheet

U.S. PATENT DOCUMENTS

| | | | |
|---|---|---|---|
| 5,756,502 A | 5/1998 | Padia | 514/248 |
| 5,863,932 A | 1/1999 | Matsunaga | 514/383 |
| 5,942,509 A | 8/1999 | Clough et al. | 514/241 |
| 5,948,775 A | 9/1999 | Koko et al. | 514/212 |
| 5,994,382 A | 11/1999 | Schwalge et al. | 514/383 |
| 5,998,455 A | 12/1999 | Knauf-Beiter et al. | 514/383 |
| 6,011,068 A | 1/2000 | Nemeth et al. | 514/654 |
| 6,031,003 A | 2/2000 | Nemeth et al. | 514/579 |
| 6,060,479 A | 5/2000 | Chenard et al. | 514/258 |
| 6,100,270 A | 8/2000 | Campbell | 514/258 |
| 6,107,336 A | 8/2000 | Elbe et al. | 514/471 |
| 6,110,471 A | 8/2000 | Conti et al. | 424/400 |
| 6,136,812 A | 10/2000 | Chenard et al. | 514/259 |
| 6,187,779 B1 | 2/2001 | Pamukcu et al. | 514/259 |
| 6,211,236 B1 | 4/2001 | Muller et al. | 514/539 |
| 6,211,244 B1 | 4/2001 | Van Wagenen et al. | 514/649 |
| 6,225,315 B1 | 5/2001 | Ellis | 514/250 |
| 6,225,318 B1 | 5/2001 | Sobolov-Jaynes et al. | 514/259 |
| 6,235,730 B1 | 5/2001 | Sato et al. | 514/211.11 |
| 6,239,130 B1 | 5/2001 | Pascal et al. | 514/220 |
| 6,245,792 B1 | 6/2001 | Muller et al. | 514/383 |
| 6,255,352 B1 | 7/2001 | Grammenos et al. | 514/640 |
| 6,303,615 B1 | 10/2001 | Elliott et al. | 514/259 |
| 6,306,864 B1 | 10/2001 | Welch et al. | 514/259 |
| 6,306,865 B1 | 10/2001 | Pendergast et al. | 514/267 |
| 6,313,146 B1 | 11/2001 | Van Wagenen et al. | 514/337 |
| 6,331,543 B1 | 12/2001 | Garvey et al. | 514/350 |
| 6,337,332 B1 | 1/2002 | Carpino | 514/259 |
| 6,350,765 B1 | 2/2002 | Schelberger et al. | 514/355 |
| 6,369,090 B1 | 4/2002 | Schelberger et al. | 514/384 |
| 6,380,204 B1 | 4/2002 | Chenard et al. | 514/259 |
| 6,391,874 B1 | 5/2002 | Cockerill et al. | 514/233.5 |
| 6,465,472 B1 | 10/2002 | Upasani et al. | 514/258 |
| 6,518,277 B1 | 2/2003 | Sadhu et al. | 514/266.1 |
| 6,545,004 B1 | 4/2003 | Finer et al. | 514/266.2 |
| 6,559,160 B1 | 5/2003 | Schall et al. | 514/284 |
| 6,562,830 B1 | 5/2003 | Pamukcu et al. | 514/259 |
| 6,627,755 B1 | 9/2003 | Chenard et al. | 544/284 |
| 6,664,390 B2 | 12/2003 | Barth et al. | 544/119 |
| 6,713,485 B2 | 3/2004 | Carter et al. | 514/266.24 |
| 6,828,315 B1 | 12/2004 | Gaudilliere et al. | 514/217.09 |
| 6,890,930 B1 | 5/2005 | Mederski et al. | 514/266.2 |
| 6,897,213 B1 | 5/2005 | Padia | 514/234.5 |
| 6,916,956 B2 | 7/2005 | Shinagawa et al. | 564/88 |
| 7,060,706 B1 | 6/2006 | Mederski et al. | 514/266.31 |
| 7,157,476 B2 | 1/2007 | Come et al. | 514/341 |
| 7,271,179 B2 | 9/2007 | Bemis et al. | 514/312 |
| 7,407,962 B2 | 8/2008 | Aronov et al. | 514/258.1 |
| 7,462,612 B2 | 12/2008 | Hale et al. | 514/235.5 |
| 7,488,727 B2 | 2/2009 | Cochran et al. | 514/235.8 |
| 2001/0034345 A1 | 10/2001 | Greenamyre et al. | 514/249 |
| 2001/0055570 A1 | 12/2001 | Naef | 424/44 |
| 2002/0094326 A1 | 7/2002 | Donahue et al. | 424/93.21 |
| 2002/0119967 A1 | 8/2002 | Moulon et al. | 514/220 |
| 2002/0128171 A1 | 9/2002 | Watkins et al. | 514/1 |
| 2002/0161014 A1 | 10/2002 | Sadhu et al. | 514/266.2 |
| 2002/0169159 A1 | 11/2002 | Medina et al. | 514/227.5 |
| 2002/0177601 A1 | 11/2002 | Himmelsbach et al. | 514/266.2 |
| 2003/0013733 A1 | 1/2003 | Apodaca et al. | 514/306 |
| 2003/0060626 A1 | 3/2003 | Clough et al. | 544/123 |
| 2003/0069230 A1 | 4/2003 | Becker et al. | 514/223.2 |
| 2003/0166581 A1 | 9/2003 | Almarsson et al. | 514/23 |
| 2004/0006130 A1 | 1/2004 | Shinagawa et al. | 514/467 |
| 2004/0009980 A1 | 1/2004 | Bhatnagar et al. | 514/241 |
| 2004/0019049 A1 | 1/2004 | Boyce et al. | 514/243 |
| 2004/0048853 A1 | 3/2004 | Bergnes | 514/218 |
| 2004/0067969 A1 | 4/2004 | Bergnes et al. | 514/266.3 |
| 2004/0077668 A1 | 4/2004 | Feng et al. | 514/266.23 |
| 2004/0102450 A1 | 5/2004 | Ewing et al. | 514/252.13 |
| 2004/0106616 A1 | 6/2004 | Bakthavatchalam et al. | 514/243 |
| 2004/0110777 A1 | 6/2004 | Annis et al. | 514/264.1 |
| 2004/0132732 A1 | 7/2004 | Han et al. | 514/248 |
| 2004/0142949 A1 | 7/2004 | Bergnes et al. | 514/266.2 |
| 2004/0142958 A1 | 7/2004 | Herzberg et al. | 514/282 |
| 2004/0167198 A1 | 8/2004 | Wrasidlo et al. | 514/414 |
| 2004/0176361 A1 | 9/2004 | Fujio et al. | 514/224.2 |
| 2004/0186140 A1 | 9/2004 | Cherney et al. | 514/340 |
| 2004/0198790 A1 | 10/2004 | Mori et al. | 514/383 |
| 2004/0204431 A1 | 10/2004 | Scarborough et al. | 514/266.2 |
| 2004/0214819 A1 | 10/2004 | Rudolf et al. | 514/222.5 |
| 2004/0242568 A1 | 12/2004 | Feng et al. | 514/223.8 |
| 2004/0242572 A1 | 12/2004 | Stenkamp et al. | 514/227.2 |
| 2004/0242604 A1 | 12/2004 | Bhattacharya et al. | 514/266.4 |
| 2004/0248890 A1 | 12/2004 | Gonzalez, III et al. | 514/227.8 |
| 2004/0259826 A1 | 12/2004 | Fraley et al. | 514/44 |
| 2005/0004177 A1 | 1/2005 | Roark | 514/341 |
| 2005/0038016 A1 | 2/2005 | Connolly et al. | 514/223.2 |
| 2005/0038051 A1 | 2/2005 | Nunnari et al. | 514/266.2 |
| 2005/0043239 A1 | 2/2005 | Douangpanya et al. | 514/12 |
| 2005/0054651 A1 | 3/2005 | Natarajan et al. | 514/249 |
| 2005/0059651 A1 | 3/2005 | Armstrong et al. | 514/212.03 |
| 2005/0059662 A1 | 3/2005 | Boyce et al. | 514/243 |
| 2005/0107448 A1 | 5/2005 | Shinagawa et al. | 514/357 |
| 2005/0130954 A1 | 6/2005 | Mitchell et al. | 514/210.21 |
| 2005/0136065 A1 | 6/2005 | Valiante, Jr. | 424/164.1 |
| 2005/0137213 A1 | 6/2005 | Cai et al. | 514/262.1 |
| 2005/0181066 A1 | 8/2005 | Grimminger et al. | 424/608 |
| 2005/0182045 A1 | 8/2005 | Nagase et al. | 514/217.06 |
| 2005/0192297 A1 | 9/2005 | Boyce et al. | 514/266.2 |
| 2005/0203110 A1 | 9/2005 | Coleman et al. | 514/264.1 |
| 2005/0227309 A1 | 10/2005 | Corry et al. | 435/32 |
| 2005/0227919 A1 | 10/2005 | Ashworth et al. | 514/12 |
| 2005/0239809 A1 | 10/2005 | Watts et al. | 514/263.21 |
| 2005/0245539 A1 | 11/2005 | Mendla et al. | 514/254.06 |
| 2006/0009455 A1 | 1/2006 | Corte et al. | 514/249 |
| 2006/0017426 A1 | 1/2006 | Yang et al. | 323/283 |
| 2006/0019974 A1 | 1/2006 | Mederski et al. | 514/266.22 |
| 2006/0025420 A1 | 2/2006 | Brauns et al. | 514/252.16 |
| 2006/0052345 A1 | 3/2006 | Shcherbakova et al. | 514/81 |
| 2006/0063707 A1 | 3/2006 | Baudry et al. | 514/8 |
| 2006/0069099 A1 | 3/2006 | Fu et al. | 514/251 |
| 2006/0079538 A1 | 4/2006 | Hallahan et al. | 514/263.21 |
| 2006/0079685 A1 | 4/2006 | Altmann et al. | 544/283 |
| 2006/0094723 A1 | 5/2006 | Dunkern et al. | 514/248 |
| 2006/0106038 A1 | 5/2006 | Bouscary et al. | 514/263.21 |
| 2006/0148693 A1 | 7/2006 | Wollin | 514/12 |
| 2006/0154935 A1 | 7/2006 | Wilson et al. | 514/252.17 |
| 2006/0154942 A1 | 7/2006 | Culshaw et al. | 514/266.24 |
| 2006/0217426 A1 | 9/2006 | Eto et al. | 514/355 |
| 2006/0258651 A1 | 11/2006 | Linschoten | 514/229.5 |
| 2006/0264449 A1 | 11/2006 | Bergnes et al. | 514/266.2 |
| 2007/0032508 A1 | 2/2007 | Bradbury et al. | 514/255.05 |
| 2007/0060601 A1 | 3/2007 | Arrington et al. | 514/266.31 |
| 2007/0082873 A1 | 4/2007 | Lingenhohl et al. | 514/80 |
| 2007/0149546 A1 | 6/2007 | Bradbury et al. | 514/255.05 |
| 2007/0149553 A1 | 6/2007 | Arrington et al. | |
| 2007/0161792 A1 | 7/2007 | Shcherbakova et al. | |
| 2007/0185114 A1 | 8/2007 | Dunkern et al. | 514/243 |
| 2007/0203226 A1 | 8/2007 | Marquis, Jr. | 514/444 |
| 2007/0232607 A1 | 10/2007 | Bradbury et al. | 514/234.5 |
| 2007/0232628 A1 | 10/2007 | Luengo et al. | 514/266.3 |
| 2007/0244136 A1 | 10/2007 | Hennequin et al. | 514/266.1 |

FOREIGN PATENT DOCUMENTS

| | | |
|---|---|---|
| EP | 1110953 | 6/1995 |
| EP | 0934934 | 2/1999 |
| EP | 1964548 | 9/2008 |
| GB | 2295387 | 11/1994 |
| WO | WO 9304373 | 3/1993 |
| WO | WO 9322921 | 11/1993 |
| WO | WO 9418959 | 9/1994 |
| WO | WO 9737967 | 10/1997 |
| WO | WO 9844925 | 10/1998 |

| WO | WO 9845255 | 10/1998 |
| WO | WO 9951569 | 10/1999 |
| WO | WO 9961241 | 10/1999 |
| WO | WO 9959584 | 11/1999 |
| WO | WO 0045816 | 8/2000 |
| WO | WO 0238106 | 5/2002 |
| WO | WO 0248115 | 6/2002 |
| WO | WO 02102782 | 12/2002 |
| WO | WO 03076418 | 9/2003 |
| WO | WO 2004030672 | 4/2004 |
| WO | WO 9410845 | 5/2004 |
| WO | WO 2004041755 | 5/2004 |
| WO | WO 2004043956 | 5/2004 |
| WO | WO 2004092120 | 10/2004 |
| WO | WO 2005030746 | 4/2005 |
| WO | WO 2005039593 | 5/2005 |
| WO | WO 2005039594 | 5/2005 |
| WO | WO 2005041879 | 5/2005 |
| WO | WO 2005044194 | 5/2005 |
| WO | WO 2005049039 | 6/2005 |
| WO | WO 2005049041 | 6/2005 |
| WO | WO 2005049042 | 6/2005 |
| WO | WO 2005058295 | 6/2005 |
| WO | WO 2005113556 | 12/2005 |
| WO | WO 2005120511 | 12/2005 |
| WO | WO 2006012577 | 2/2006 |
| WO | WO 2006016262 | 2/2006 |
| WO | WO 2006024834 | 3/2006 |
| WO | WO 2006066070 | 6/2006 |
| WO | WO 2007062370 | 5/2007 |

OTHER PUBLICATIONS

Raubenheimer, Advances in Anatomic Pathology, Jan. 2004, vol. 11, #1, pp. 38-48.*

Fitzpatrick, Osteoporos. Int. (2010) 21:[Su[[I1], Article OC19, S16-S18.*

Garner, et al., Endocrin., 142(9): 3996-4005, 2001.*

Arey, B. J., et al., "A Novel Calcium-Sensing Receptor Antagonist Transiently Stimulates Parathyroid Hormone Secretion in Vivo", *Endocrinology*, vol. 146, No. 4, pp. 2015-2022, (2005).

Bak, et al., *Calcif. Tissue International*, "The Effects of Aging on Fracture Healing in Rats", vol. 45, pp. 292-297 (1989).

Cottet, et al., Recommendable routes to trifluoromethyl-substituted pyridine- and quinolinecarboxylic acids. *European Journal of Organic Chemistry* (2003), vol. (8), 1559-1568.

Hu, J., et al., "A Region in the Seven-transmembrane Domain of the Human $Ca^{2+}$ Receptor Critical Response to $Ca^{2+}$", *The Journal of Biological Chemistry*, vol. 280, No. 6, pp. 5113-5120, (2005).

Kiyama, et al., Synthesis and evaluation of novel nonpeptide angiotensin II receptor antagonists: imidazo[4,5-c]pyridine derivatives with an aromatic substituent. *Chemical & Pharmaceutical Bulletin* (1995), vol. 43(3), pp. 450-460.

Kessler, et al., N(1)-Arylsulfonyl-N(2)-(1-(1-naphthyl)ethyl)-1,2-diaminocyclohexanes: a new class of calcilytic agents acting at the calcium-sensing receptor. *Chembiochem : a European journal of chemical biology* (2004), vol. 5(8), pp. 1131-1136.

Murray, T. M., "Parathyroid Hormone Secretion and Action: Evidence for Discrete Receptors for the Carboxyl-Terminal Region and Related Bological Actions of Carboxyl-Terminal Ligands," *Endocrine Reviews*, vol. 26, No. 1, pp. 78-113, (2005).

Nemeth, E. F., "The search for calcium receptor antagonists (calcilytics)." *Journal of Molecular Endocrinology* (2002), 29(1), 15-21.

Nemeth, E. F., et al., "Pharmacodynamics of the Type II Calcimimetic Compound Cinacalcet HCl," *Journal of Pharmacology and Experimental Therapeutics*, vol. 308, No. 2, pp. 627-635, (2004).

Pearse, et al.,*Injury*, "Outcome following a second hip fracture", vol. 34(7), pp. 518-521 (2003).

Shcherbakova, et al., 3H-Quinazolin-4-ones as a new calcilytic template for the potential treatment of osteoporosis, *Bioorganic & Medicinal Chemistry Letters* (2005), vol. 15(6), pp. 1557-1560.

Steddon, et al., Calcimimetics and calcilytics-fooling the calcium receptor, *Lancet* (2005), vol. 365(9478), pp. 2237-2239.

Takeuchi, et al., "Enhancement of the dissolution rate of a poorly water-soluble drug (tolbutamide) by a spray-drying solvent deposition method and disintegrants" *J. Pharm. Pharmacol.*, vol. 39, pp. 769-773 (1987).

Morrison and Boyd, Organic Chemistry, $3^{rd}$ Edition, Chapter 31, Heterocyclic Compounds, pp. 1002-1006, Allyn and Bacon, Inc. Boston MA 1973 ($7^{th}$ printing Jan. 1975).

Sussman, A.S., "The Effect of Heterocyclic and other Compounds upon the Germination of Ascospores of *Neurospora tetrasperma*", Journal Gen. Microbiol., 1953, pp. 211-216, vol. 8.

Crews, P., et al., "Localization or Delocalization of Nonbonded Electrons in Unsaturated Heterocycles", Journal of Organic Chemistry, 1973, pp. 4391-4395, vol. 38, No. 26.

Amin, M., et al., "Synthetic Approaches to Unsaturated Five-membered Heterocycles Containing Both Ring and Side-chain Phosphorus Atoms", Journal of Heterocyclic Chemistry, Mar.-Apr. 1985, pp. 513-522, vol. 22.

Kurita, J., et al., "Studies on Diazepines. XXV.[1]) Syntheses of Fully Unsaturated 1,4-Oxazepines and 1*H*-1,4-Diazepines Using Photochemical Valence Isomerization of Tricycloheptene Systems", Chem. Pharm. Bull., 1987, pp. 3166-3174, vol. 35, No. 8.

Holmes, A.H., et al., "The Synthesis of Fully Unsaturated 11-, 12-, and 13-Membered Sulfur Heterocycles[1]", Journal of the American Chemical Society, Aug. 26, 1970, pp. 5284-5284, vol. 92, No. 17.

Shcherbakova et al, Bioorganic & Medicinal Chemistry Letters, vol. 15, No. 10, May 16, 2005, pp. 2537-2540.

* cited by examiner

PYRIDO[4,3-D]PYRIMIDIN-4(3H)-ONE DERIVATIVES AS CALCIUM RECEPTOR ANTAGONISTS

FIELD OF INVENTION

The present invention is directed toward novel pyrido[4,3-d]pyrimidin-4(3H)-one derivatives, pharmaceutical compositions containing these compounds, methods for their use and processes for their production. These novel pyrido[4,3-d]pyrimidin-4(3H)-one derivatives are able to inhibit calcium receptor activity and thus act as calcium receptor antagonists.

BACKGROUND OF THE INVENTION

In mammals, extracellular $Ca^{2+}$ is under rigid homeostatic control with the serum calcium concentration strictly maintained at a concentration of approximately 1.1 to 1.3 mM in a healthy mammal. The extracellular $Ca^{2+}$ homeostasis depends on integrated regulation of $Ca^{2+}$ fluxes with respect to the intestine, kidneys and bone. The extracellular $Ca^{2+}$ regulates various processes such as blood coagulation, nerve and muscle excitability, and normal bone homeostasis. When the $Ca^{2+}$ serum concentration decreases by 50% tetania occurs, and when the $Ca^{2+}$ serum concentration increases by 50% consciousness is clouded, in both instances a potentially life threatening circumstance. Extracellular $Ca^{2+}$ also inhibits the secretion of parathyroid hormone (PTH) from parathyroid cells, inhibits bone resorption by osteoclasts, stimulates secretion of calcitonin from C-cells and is involved in re-absorption and excretion in the kidney.

The extracellular calcium-sensing receptor (CaSR) is a hormone-like receptor, more particularly a plasma membrane-bound G protein-coupled receptor (GPCR) that belongs to family 3 of the GPCR superfamily. Family 3 of the GPCR superfamily includes metabotropic glutamate receptors (mGluRs), γ-aminobutyric acid B-type receptors (GABABRS) as well as putative pheromone and taste receptors. The CaSR has a large extracellular domain exhibiting "Venus flytrap" topology, a seven-transmembrane domain and a relatively large cytoplasmic domain. Human CaSR consists of 1078 amino acids and shares 93% amino acid homology with bovine CaSR. The CaSR senses and is activated by changes in extracellular $Ca^{2+}$ levels. The presence of CaSR on certain specialized cells enables those $Ca^{2+}$-sensing cells to respond to changes in extracellular $Ca^{2+}$ concentration. Examples of $Ca^{2+}$-sensing cells include the parathyroid-secreting cells of the parathyroid gland, the calcitonin-secreting C cells of the thyroid gland and certain cells in the kidney. In addition, the CaSR has been found in a wide variety of other tissues including intestine, bone, bone marrow, brain, skin, pancreas, lung and heart.

The CaSR on the surface of parathyroid chief cells is the primary entity that regulates secretion of PTH from parathyroid cells. Activation of the CaSR on parathyroid chief cells by extracellular $Ca^{2+}$ suppresses PTH production and secretion, inhibits parathyroid cellular proliferation and likely inhibits PTH gene expression. The CaSR on the surface of the calcitonin-secreting C cells of the thyroid gland mediate the stimulatory action of high extracellular $Ca^{2+}$ concentration on calcitonin secretion, thereby increasing the circulating level of the $Ca^{2+}$-lowering hormone calcitonin. The CaSR is also present in the kidney, along much of the nephrons and at the basolateral surface in the cortical thick ascending limb. In the basolateral surface in the cortical thick ascending limb the CaSR is thought to mediate high $Ca^{2+}$-induced inhibition of the tubular re-absorption of $Ca^{2+}$ and magnesium. A reduction of renal cortical synthesis of $1,25(OH)_2$ vitamin D and polyuria with dilute urine are partially the result of hypercalcaemic activation of the CaSR in the nephron.

PTH is the primary endocrine hormone regulating $Ca^{2+}$ homeostasis in the blood and extracellular fluids. PTH, by acting on bone and kidney cells, increases the level of $Ca^{2+}$ in the plasma. This increase in plasma $Ca^{2+}$ concentration then acts as a negative feedback signal, thereby depressing PTH secretion. The reciprocal relationship between extracellular $Ca^{2+}$ and PTH secretion forms an important mechanism for maintaining bodily $Ca^{2+}$ homeostasis. PTH has been found to increase bone turnover, but the overall effect on bone is dependent on temporal changes in circulating levels of PTH. Sustained elevations in circulating plasma PTH levels, as occurs in hyperparathyroidism, have been found to result in a net catabolic effect on bone. By contrast, transient increases in plasma PTH levels, achieved by daily or near daily injection of exogenous hormone, have been found to exhibit a net anabolic effect on bone. The effect of PTH on bone is likely due to PTH being able to induce a rapid release of calcium from bone and mediate other changes by acting directly on osteoblasts and indirectly on osteoclasts. PTH affects cellular metabolic activity, ion transport, cell shape, gene transcriptional activity and secretion of proteases in osteoblasts. Also, PTH stimulates the production of RANKL, a protein that plays a crucial role in osteoclast differentiation and activity.

Various compounds are known to modulate the effects of extracellular $Ca^{2+}$ on the CaSR. Calcimimetics are agents that act as allosteric modulators of the CaSR that increase the sensitivity of the CaSR to activation by extracellular $Ca^{2+}$. Calcilytics, or calcium receptor antagonists, are agents that act as modulators of the CaSR that inhibit CaSR activity. This inhibition of the CaSR activity results in a decrease of one or more CaSR activities that are evoked by extracellular $Ca^{2+}$.

Certain urea derivatives, such as those disclosed in PCT International Publication WO 02/059102, are described as having calcimimetic activity. In addition, certain phenylalkylamine derivatives have been identified as calcimimetics. Phenylalkylamine calcimimetic compounds include (R)—N-(1-(3-methoxyphenyl)ethyl)-3-phenylpropan-1-amine hydrochloride (NPS-467); (R)-3-(2-chlorophenyl)-N-(1-(3-methoxyphenyl)ethyl)propan-1-amine hydrochloride (NPS R-568, tecalcet hydrochloride) and (R)-(−)-N-(1-(naphthalen-1-yl)ethyl)-3-(3-(trifluoromethyl)phenyl)propan-1-amine hydrochloride (NPS-1493, cinacalcet hydrochloride). Cinacalcet hydrochloride and uses thereof are disclosed in U.S. Pat. Nos. 6,011,068; 6,031,003; 6,211,244 and 6,313,146. Cinacalcet hydrochloride is marketed as Sensipar® and Minpara® in the U.S. and Europe, respectively, and is indicated for the treatment of secondary hyperparathyroidism in patients with chronic kidney disease on dialysis and for hypercalcemia in patients with parathyroid carcinoma.

Calcilytics, or calcium receptor antagonists, have been described in various publications such as PCT International Publication Nos. WO 93/04373; WO 94/18959; WO 95/11211; WO 97/37967; WO 98/44925; WO 98/45255; WO 99/51241; WO 99/51569; WO 00/45816; WO 02/14259; WO 02/38106; WO 2004/041755; and WO 2005/030746; Nemeth, E. F.; *Journal of Molecular Endocrinology* (2002) 29, 15-21; Kessler, A. et al.; *ChemBioChem* (2004) 5, 1131; Steddon, S. J. et al.; *Lancet* (2005) 365, 2237-2239; and Shcherbakova, I.; et al.; *Bioorganic & Medicinal Chemistry Letters* (2005) 15, 1557-1560.

Calcium receptor antagonists are useful in the treatment of various disease states characterized by abnormal levels of one or more components, e.g., polypeptides such as hormones, enzymes or growth factors, the expression and/or secretion of which is regulated or affected by activity at one or more CaSR. Target diseases or disorders for calcium receptor antagonists include diseases involving abnormal bone and mineral homeostasis. Abnormal calcium homeostasis is characterized by one or more of the following activities: an abnormal increase or decrease in serum calcium; an abnormal increase or decrease in urinary excretion of calcium; an abnormal increase or decrease in bone calcium levels (for example, as assessed by bone mineral density measurements); an abnormal absorption of dietary calcium; an abnormal increase or decrease in the production and/or release of messengers which affect serum calcium levels such as PTH and calcitonin; and an abnormal change in the response elicited by messengers which affect serum calcium levels.

The novel calcium receptor antagonists of this invention are useful in the treatment of diseases associated with abnormal bone or mineral homeostasis. Thus, these calcium receptor antagonists are useful in the treatment of hypoparathyroidism, osteoporosis, osteopenia, periodontal disease, bone fracture, osteoarthritis, rheumatoid arthritis, Paget's disease, humoral hypercalcemia associated with malignancy.

SUMMARY OF THE INVENTION

The present invention is directed towards calcium receptor antagonist compounds, pharmaceutical compositions containing the calcium receptor antagonist compounds and methods of treatment employing the calcium receptor antagonist compounds.

More specifically, the present invention is directed to calcium receptor antagonists that are pyrido[4,3-d]pyrimidin-4(3H)-one derivatives of structural formula I

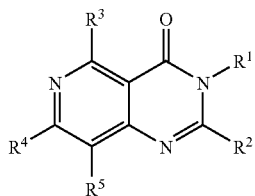

I wherein
$R^1$ is -Q or $(C_1-C_6)$alkyl-Q;
$R^2$ is $(C_1-C_6)$alkyl, $(C_3-C_7)$cycloalkyl, aryl or heteroaryl; wherein said aryl or heteroaryl is substituted with hydroxy and additionally said $(C_1-C_6)$alkyl, $(C_3-C_7)$cycloalkyl, aryl or heteroaryl within the definition of $R^2$ is optionally substituted with one to three substituents independently selected from halo, cyano, trifluoromethyl, trifluoromethoxy, $(C_1-C_6)$alkyl, $(C_1-C_6)$alkoxy or hydroxy;
$R^3$ is hydrogen, $(C_1-C_6)$alkyl, $(C_3-C_7)$cycloalkyl, $(C_1-C_6)$alkyl-Q, aryl, heteroaryl, $OR^6$, or $NR^7R^8$; wherein said $(C_1-C_6)$alkyl, $(C_3-C_7)$cycloalkyl, aryl or heteroaryl is optionally substituted with one to three substituents independently selected from halo, cyano, trifluoromethyl, trifluoromethoxy, $(C_1-C_6)$alkyl; $(C_1-C_6)$alkoxy, $NR^7R^8$ or hydroxy;
$R^4$ and $R^5$ are each independently hydrogen, halo, cyano, $(C_1-C_6)$alkyl optionally substituted with one to three fluoro, aryl, heteroaryl, or $OR^6$;
$R^6$ at each occurrence is independently $(C_1-C_6)$alkyl, $(C_3-C_7)$cycloalkyl, $(C_3-C_7)$cycloalkyl-$(C_1-C_6)$alkyl, aryl, heteroaryl, $(C_1-C_6)$alkylaryl, or $(C_1-C_6)$alkylheteroaryl; each of said $(C_1-C_6)$alkyl, $(C_3-C_7)$cycloalkyl, $(C_3-C_7)$cycloalkyl-$(C_1-C_6)$alkyl, aryl, heteroaryl, $(C_1-C_6)$alkylaryl, or $(C_1-C_6)$alkylheteroaryl optionally substituted with one to three substituents independently selected from halo, hydroxy or $(C_1-C_3)$alkyl;
$R^7$ and $R^8$, at each occurrence, are independently hydrogen, $(C_1-C_6)$alkyl, or $(C_3-C_7)$cycloalkyl; or $R^7$ and $R^8$ taken together with the nitrogen to which they are attached form a 3 to 7 membered fully saturated, partially saturated or fully unsaturated ring optionally containing one to two additional heteroatoms independently selected from $N(R^9)_n$; O or $S(O)_p$
n is 0 or 1;
p is 0, 1 or 2;
$R^9$ is hydrogen or $(C_1-C_6)$alkyl;
Q, at each occurrence, is independently aryl or heteroaryl; wherein said aryl or heteroaryl is optionally substituted with one to three substituents independently selected from halo, cyano, trifluoromethyl, trifluoromethoxy, $(C_1-C_6)$alkyl, $(C_1-C_6)$alkoxy or hydroxy;

or a pharmaceutically acceptable salt thereof.

"Halo" refers to fluoro, chloro, bromo or iodo.

"$(C_1-C_6)$alkyl" refers to a hydrocarbon group having one to six carbon atoms joined together by single carbon-carbon bonds. The $(C_1-C_6)$alkyl group may be straight-chain or contain one or more branches and may be unsubstituted or substituted as specified. Examples of $(C_1-C_6)$alkyl groups include methyl, ethyl, n-propyl, isopropyl, n-butyl, sec-butyl, tert-butyl, n-pentyl, (1-methyl)butyl, (2-methyl)butyl, (3-methyl)butyl, (1,2-dimethyl)propyl, n-hexyl, (1-methyl)pentyl, (2-methyl)pentyl, (3-methyl)pentyl, (4-methyl)pentyl, (1-ethyl)butyl, (2-ethyl)butyl, (1,2-dimethyl)butyl, (1,3-dimethyl)butyl, (2,3-dimethyl)butyl and the like.

"$(C_1-C_6)$alkoxy" refers to an oxygen joined to a $(C_1-C_6)$ alkyl group. The $(C_1-C_6)$alkyl group in the $(C_1-C_6)$alkoxy moiety may be straight-chain or contain one or more branches and may be unsubstituted or substituted as specified. Examples of $(C_1-C_6)$alkoxy groups include methoxy, ethoxy, n-propoxy, isopropoxy, n-butoxy, sec-butoxy, tert-butoxy, n-pentoxy and the like. Likewise, alkyl or alkoxy groups of differing length such as "$(C_1-C_3)$alkyl" or "$(C_1-C_3)$alkoxy" are defined in the same manner but limited to the number of carbons present.

"$(C_3-C_7)$cycloalkyl" refers to a saturated carbocyclic group having three to seven carbons and encompasses cyclopropyl, cyclobutyl, cyclopentyl, cyclohexyl and cycloheptyl. The $(C_3-C_7)$cycloalkyl group can be unsubstituted or substituted as specified.

"Aryl" refers to a six to sixteen membered carbocyclic aromatic group having at least one ring with a conjugated pi-electron system. The aryl group can have conjugated or fused rings and can be unsubstituted or substituted as specified. Examples of aryl groups include phenyl, naphthalenyl, anthracenyl, phenanthrenyl, azulenyl and biphenyl.

"Heteroaryl" refers to a five to sixteen membered aromatic group with at least one ring with a conjugated pi-electron system and containing one to four heteroatoms such as N, O or S. The hetroaryl group can have conjugated or fused rings and can be unsubstituted or substituted as specified. Examples of heteroaryl groups include thienyl, furanyl, pyrrolyl, pyrazolyl, imidazoyl, oxazolyl, isoxazolyl, thiazolyl, isothiazolyl, triazolyl, oxadiazolyl, thiadiazolyl, tetrazolyl, pyridinyl, pyridizinyl, pyrimidinyl, pyrazinyl, triazinyl, indolyl, isoindolyl, indolizinyl, benzofuranyl, benzothienyl, indazolyl, benzimidazoyl, benzthiazolyl, purinyl, quinolizinyl, quinolinyl, isoquinolinyl, cinnolinyl, phthalazinyl, quinazolinyl, quinoxalinyl, naphthyridinyl, pteridinyl, carbazolyl, acridinyl, phenazinyl, phenothiazinyl or phenoxazinyl.

DETAILED DESCRIPTION OF THE INVENTION

Figure 1:
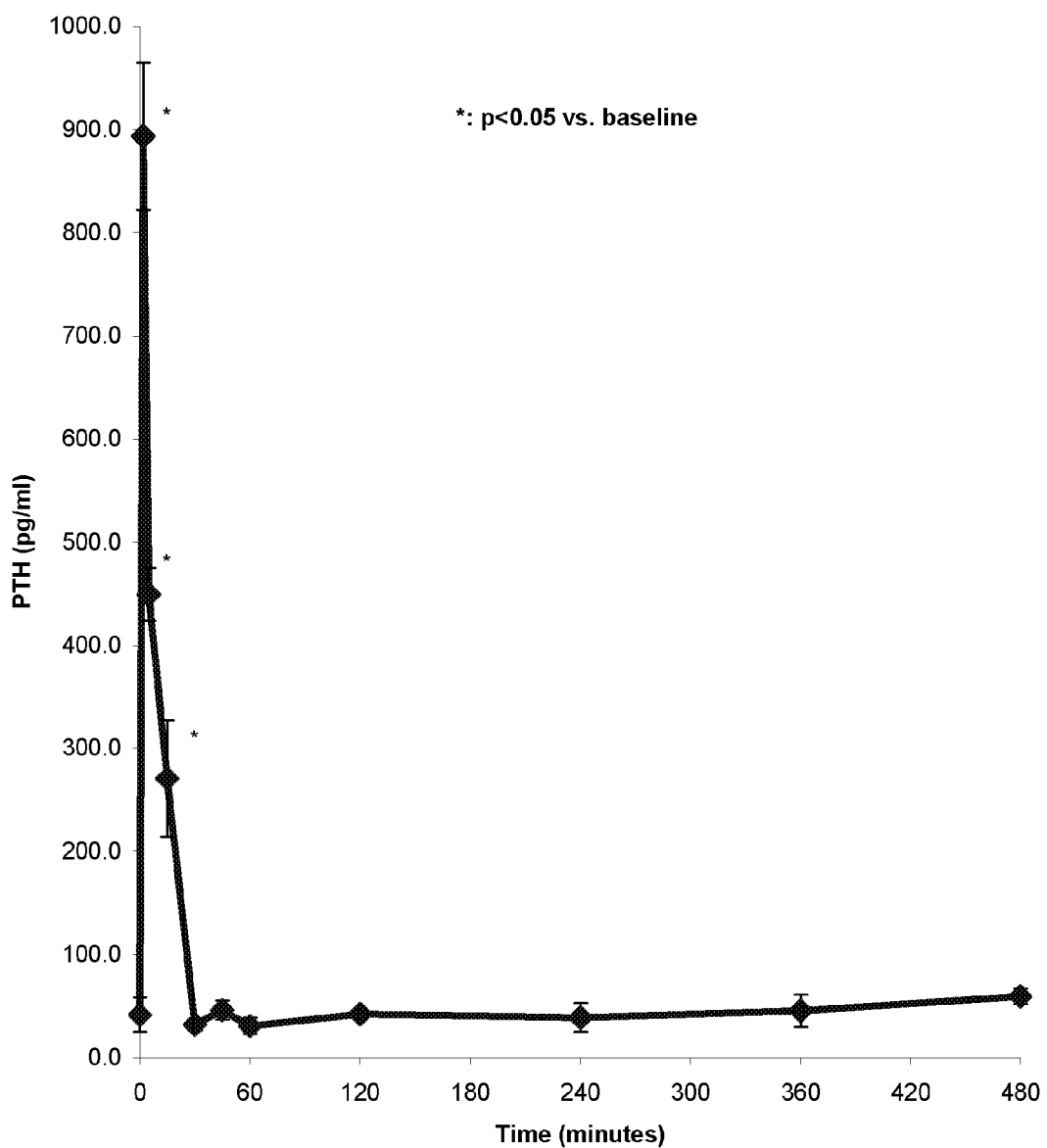
FIG. 1 is a chart depicting plasma PTH levels from the time of intravenous injection to 480 minutes following intravenous injection of 1 mg/kg of the compound of Example 1, 2-(2-Hydroxy-phenyl)-3-phenethyl-5-trifluoromethyl-3H-pyrido[4,3-d]pyri-midin-4-one), in normal rats.

The present invention provides novel pyrido[4,3-d]pyrimidin-4(3H)-one derivatives and pharmaceutically acceptable salts thereof of structural formula I

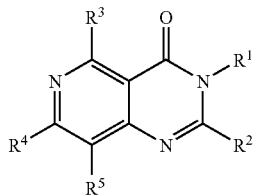

wherein the variables $R^1$, $R^2$, $R^3$, $R^4$ and $R^5$ are described hereinabove. The pharmaceutically acceptable salts of the compounds of formula I include the acid addition and base salts (including disalts) thereof.

Suitable acid addition salts are formed from acids which form non-toxic salts. Examples include the acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts. For a review on suitable salts, see "Handbook of Pharmaceutical Salts: Properties, Selection, and Use" by Stahl and Wermuth (Wiley-VCH, Weinheim, Germany, 2002).

A pharmaceutically acceptable salt of a compound of formula I may be readily prepared by mixing together solutions of the compound of formula I and the desired acid or base, as appropriate. The salt may precipitate from solution and be collected by filtration or may be recovered by evaporation of the solvent. The degree of ionization in the salt may vary from completely ionized to almost non-ionized.

The compounds of the invention include compounds of formula I as hereinbefore defined, polymorphs, and isomers thereof (including optical, geometric and tautomeric isomers) as hereinafter defined and isotopically-labeled compounds of formula I.

The compounds of the present invention may be administered as prodrugs. Thus certain derivatives of compounds of formula I which may have little or no pharmacological activity themselves can, when administered into or onto the body, be converted into compounds of formula I having the desired activity, for example, by hydrolytic cleavage. Such derivatives are referred to as 'prodrugs'. Further information on the use of prodrugs may be found in 'Pro-drugs as Novel Delivery Systems, Vol. 14, ACS Symposium Series (T Higuchi and W Stella) and 'Bioreversible Carriers in Drug Design', Pergamon Press, 1987 (ed. E B Roche, American Pharmaceutical Association).

Prodrugs can, for example, be produced by replacing appropriate functionalities present in the compounds of formula I with certain moieties known to those skilled in the art as 'pro-moieties' as described, for example, in "Design of Prodrugs" by H Bundgaard (Elsevier, 1985).

Some examples of such prodrugs include:
(i) where the compound of formula I contains a carboxylic acid functionality (—COOH), an ester thereof, for example, replacement of the hydrogen with $(C_1$-$C_8)$alkyl;
(ii) where the compound of formula I contains an alcohol functionality (—OH), an ether thereof, for example, replacement of the hydrogen with $(C_1$-$C_6)$alkanoyloxymethyl; and
(iii) where the compound of formula I contains a primary or secondary amino functionality (—$NH_2$ or —NHR where R is not H), an amide thereof, for example, replacement of one or both hydrogens with $(C_1$-$C_{10})$alkanoyl. Further examples of replacement groups in accordance with the foregoing examples and examples of other prodrug types may be found in the aforementioned references. Finally, certain compounds of formula I may themselves act as prodrugs of other compounds of formula I.

Compounds of formula I containing one or more asymmetric carbon atoms can exist as two or more stereoisomers. Where a compound of formula I contains an alkenyl or alkenylene group, geometric cis/trans (or Z/E) isomers are possible. Where the compound contains, for example, a keto or oxime group or an aromatic moiety, tautomeric isomerism ('tautomerism') can occur. It follows that a single compound may exhibit more than one type of isomerism.

Included within the scope of the claimed compounds of formula I are all stereoisomers, geometric isomers and tautomeric forms of the compounds of formula I, including compounds exhibiting more than one type of isomerism, and mixtures of one or more thereof. Also included are acid addition or base salts wherein the counterion is optically active, for example, D-lactate or L-lysine, or racemic, for example, DL-tartrate or DL-arginine. Cis/trans isomers may be separated by conventional techniques well known to those skilled in the art, for example, chromatography and fractional crystallisation. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound of formula (I) contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to a skilled person. Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% isopropanol, typically from 2 to 20%, and from 0 to 5% of an alkylamine, typically 0.1% diethylamine. Concentration of the eluate affords the enriched mixture. Mixtures of stereoisomers may be separated by conventional techniques known to those skilled in the art. [see, for example, "Stereochemistry of Organic Compounds" by E L Eliel (Wiley, New York, 1994).]

The present invention includes all pharmaceutically acceptable isotopically-labelled compounds of formula I wherein one or more atoms are replaced by atoms having the same atomic number, but an atomic mass or mass number different from the atomic mass or mass number usually found in nature.

Examples of isotopes suitable for inclusion in the compounds of the invention include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulfur, such as $^{35}$S. Certain isotopically-labelled compounds of formula I, for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection. Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances. Substitution with positron emitting isotopes, such as $^{11}$C, $^{18}$F, $^{15}$O and $^{13}$N, can be useful in Positron Emission Topography (PET) studies for examining substrate receptor occupancy. Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

A preferred embodiment of the present invention are compounds of Formula I as described above wherein $R^2$ is aryl or heteroaryl, wherein said aryl or heteroaryl is substituted with hydroxy and optionally substituted with one to three substituents independently selected from $(C_1-C_6)$alkoxy or halo; or a pharmaceutically acceptable salt thereof. Another preferred embodiment of this invention is a compound of Formula I, wherein $R^2$ is 2-hydroxy-phenyl or 3-hydroxy-pyridin-2-yl; wherein said 2-hydroxy-phenyl or 3-hydroxy-pyridin-2-yl is optionally substituted with one to two substituents independently selected from $(C_1-C_6)$alkoxy or fluoro; or a pharmaceutically acceptable salt thereof. Yet another preferred embodiment of the present invention is a compound of Formula I as described above wherein $R^1$ is $(C_1-C_6)$alkyl-Q; and Q is phenyl optionally substituted with one or two fluoro; or a pharmaceutically acceptable salt thereof.

Another preferred embodiment of the present invention is a compound of Formula I, wherein $R^1$ is phenethyl or 1-methyl-2-(phenyl)ethyl, wherein said phenethyl or 1-methyl-2-(phenyl)ethyl is optionally substituted on phenyl with one or two halo; and $R^2$ is 2-hydroxy-phenyl or 3-hydroxy-pyridin-2-yl, wherein said 2-hydroxy-phenyl or 3-hydroxy-pyridin-2-yl is optionally substituted with one or two substituents independently selected from $(C_1-C_3)$alkyl or halo; or a pharmaceutically acceptable salt thereof.

Another preferred embodiment of the present invention is a compound of Formula I, wherein $R^1$ is phenethyl or 1-methyl-2-(phenyl)ethyl, wherein said phenethyl or 1-methyl-2-(phenyl)ethyl is optionally substituted on phenyl with one or two halo; and $R^2$ is 2-hydroxy-phenyl or 3-hydroxy-pyridin-2-yl, wherein said 2-hydroxy-phenyl or 3-hydroxy-pyridin-2-yl is optionally substituted with one or two substituents independently selected from $(C_1-C_3)$alkyl or halo; $R^3$ is $(C_1-C_6)$alkyl, $(C_1-C_6)$alkyl-Q, aryl, heteroaryl, $OR^6$, or $NR^7R^8$, wherein said $(C_1-C_6)$alkyl, aryl or heteroaryl is optionally substituted with one to three substituents independently selected from halo, cyano, trifluoromethyl, trifluoromethoxy, $(C_1-C_6)$alkyl, $(C_1-C_6)$alkoxy, $NR^7R^8$ or hydroxy; and $R^4$ and $R^5$ are each hydrogen; or a pharmaceutically acceptable salt thereof.

Another preferred embodiment of the present invention is a compound of Formula I, wherein $R^1$ is phenethyl or 1-methyl-2-(phenyl)ethyl, wherein said phenethyl or 1-methyl-2-(phenyl)ethyl is optionally substituted on phenyl with one or two halo; $R^2$ is 2-hydroxy-phenyl or 3-hydroxy-pyridin-2-yl, wherein said 2-hydroxy-phenyl or 3-hydroxy-pyridin-2-yl is optionally substituted with one or two substituents independently selected from $(C_1-C_3)$alkyl or halo; $R^3$ is trifluoromethyl; and $R^4$ and $R^5$ are each hydrogen; or a pharmaceutically acceptable salt thereof.

Another preferred embodiment of the present invention is a compound of Formula I, wherein $R^1$ is phenethyl or 1-methyl-2-(phenyl)ethyl, wherein said phenethyl or 1-methyl-2-(phenyl)ethyl is optionally substituted on phenyl with one or two halo; and $R^2$ is 2-hydroxy-phenyl or 3-hydroxy-pyridin-2-yl, wherein said 2-hydroxy-phenyl or 3-hydroxy-pyridin-2-yl is optionally substituted with one or two substituents independently selected from $(C_1-C_3)$alkyl or halo; $R^3$ is $(C_1-C_6)$alkyl; and $R^4$ and $R^5$ are each hydrogen; or a pharmaceutically acceptable salt thereof.

Another preferred embodiment of the present invention is a compound of Formula I, wherein $R^1$ is phenethyl or 1-methyl-2-(phenyl)ethyl, wherein said phenethyl or 1-methyl-2-(phenyl)ethyl is optionally substituted on phenyl with one or two halo; and $R^2$ is 2-hydroxy-phenyl or 3-hydroxy-pyridin-2-yl, wherein said 2-hydroxy-phenyl or 3-hydroxy-pyridin-2-yl is optionally substituted with one or two substituents independently selected from $(C_1-C_3)$alkyl or halo; $R^3$ is $(C_1-C_6)$alkyl-Q; and $R^4$ and $R^5$ are each hydrogen; or a pharmaceutically acceptable salt thereof.

Another preferred embodiment of the present invention is a compound of Formula I, wherein $R^1$ is phenethyl or 1-methyl-2-(phenyl)ethyl, wherein said phenethyl or 1-methyl-2-(phenyl)ethyl is optionally substituted on phenyl with one or two halo; and $R^2$ is 2-hydroxy-phenyl or 3-hydroxy-pyridin-2-yl, wherein said 2-hydroxy-phenyl or 3-hydroxy-pyridin-2-yl is optionally substituted with one or two substituents independently selected from $(C_1-C_3)$alkyl or halo; $R^3$ is aryl, wherein said aryl is optionally substituted with one to three substituents independently selected from halo, cyano, trifluoromethyl, trifluoromethoxy, $(C_1-C_6)$alkyl, $(C_1-C_6)$alkoxy, $NR^7R^8$ or hydroxy; and $R^4$ and $R^5$ are each hydrogen; or a pharmaceutically acceptable salt thereof.

Another preferred embodiment of the present invention is a compound of Formula I, wherein $R^1$ is phenethyl or 1-methyl-2-(phenyl)ethyl, wherein said phenethyl or 1-methyl-2-(phenyl)ethyl is optionally substituted on phenyl with one or two halo; and $R^2$ is 2-hydroxy-phenyl or 3-hydroxy-pyridin-2-yl, wherein said 2-hydroxy-phenyl or 3-hydroxy-pyridin-2-yl is optionally substituted with one or two substituents independently selected from $(C_1-C_3)$alkyl or halo; $R^3$ is heteroaryl; wherein said heteroaryl is optionally substituted with one to three substituents independently selected from halo, cyano, trifluoromethyl, trifluoromethoxy, $(C_1-C_6)$alkyl, $(C_1-C_6)$alkoxy, $NR^7R^8$ or hydroxy; and $R^4$ and $R^5$ are each hydrogen; or a pharmaceutically acceptable salt thereof.

Another preferred embodiment of the present invention is a compound of Formula I, wherein $R^1$ is phenethyl or 1-methyl-2-(phenyl)ethyl, wherein said phenethyl or 1-methyl-2-(phenyl)ethyl is optionally substituted on phenyl with one or two halo; and $R^2$ is 2-hydroxy-phenyl or 3-hydroxy-pyridin-2-yl, wherein said 2-hydroxy-phenyl or 3-hydroxy-pyridin-2-yl is optionally substituted with one or two substituents independently selected from $(C_1-C_3)$alkyl or halo; $R^3$ is $OR^6$; and $R^4$ and $R^5$ are each hydrogen; or a pharmaceutically acceptable salt thereof.

Another preferred embodiment of the present invention is a compound of Formula I, wherein $R^1$ is phenethyl or 1-methyl-2-(phenyl)ethyl, wherein said phenethyl or 1-methyl-2-(phenyl)ethyl is optionally substituted on phenyl with one or two halo; and $R^2$ is 2-hydroxy-phenyl or 3-hydroxy-pyridin-2-yl, wherein said 2-hydroxy-phenyl or 3-hydroxy-pyridin-2-yl is optionally substituted with one or two substituents independently selected from $(C_1-C_3)$alkyl or halo; $R^3$ is $NR^7R^8$; and $R^4$ and $R^5$ are each hydrogen; or a pharmaceutically acceptable salt thereof.

A preferred embodiment of the present invention is a compound of Formula I wherein $R^3$ is trifluoromethyl; or a pharmaceutically acceptable salt thereof. Another preferred embodiment of the present invention is a compound of Formula I wherein $R^3$ is trifluoromethyl; and $R^4$ and $R^5$ are each independently hydrogen or methyl; or a pharmaceutically acceptable salt thereof. Yet another preferred embodiment of the present invention is a compound of Formula I wherein $R^2$ is aryl or heteroaryl, wherein said aryl or heteroaryl is substituted with hydroxy and optionally substituted with one to three substituents independently selected from $(C_1-C_3)$alkyl, $(C_1-C_3)$alkoxy or fluoro; $R^3$ is trifluoromethyl; and $R^4$ and $R^5$ are each independently hydrogen or methyl; or a pharmaceutically acceptable salt thereof. Yet another preferred embodiment of the present invention is a compound of Formula I wherein $R^2$ is hydroxy-phenyl or hydroxy-pyridyl, wherein said hydroxy-phenyl or hydroxy-pyridyl is optionally substituted with one to three substituents independently selected from methyl, methoxy or fluoro; $R^3$ is trifluoromethyl; and $R^4$ and $R^5$ are each independently hydrogen or methyl; or a pharmaceutically acceptable salt thereof.

Another preferred embodiment of the present invention is a compound of Formula I wherein $R^1$ is $(C_1-C_6)$alkyl-Q; Q is phenyl optionally substituted with one or two substituents independently selected from fluoro, methyl or methoxy; $R^2$ is hydroxy-phenyl or hydroxy-pyridyl, wherein said hydroxy-phenyl or hydroxy-pyridyl is optionally substituted with one to three substituents independently selected from methyl, methoxy or fluoro; $R^3$ is trifluoromethyl; and $R^4$ and $R^5$ are each independently hydrogen or methyl; or a pharmaceutically acceptable salt thereof. Still another preferred embodiment of the present invention is a compound of Formula I wherein $R^1$ is phenethyl or 1-methyl-2-(phenyl)ethyl, wherein said phenethyl or 1-methyl-2-(phenyl)ethyl is optionally substituted on phenyl with one or two fluoro; $R^3$ is trifluoromethyl; and $R^4$ and $R^5$ are each independently hydrogen or methyl; or a pharmaceutically acceptable salt thereof.

Another preferred embodiment of the present invention is a compound of Formula I wherein $R^1$ is phenethyl or 1-methyl-2-(phenyl)ethyl, wherein said phenethyl or 1-methyl-2-(phenyl)ethyl is optionally substituted on phenyl with one or two halo; $R^2$ is hydroxy-phenyl or hydroxy-pyridyl, wherein said hydroxy-phenyl or hydroxy-pyridyl is optionally substituted with one or two substituents independently selected from $(C_1-C_3)$alkyl or halo; $R^3$ is trifluoromethyl; and $R^4$ and $R^5$ are each independently hydrogen or methyl; or a pharmaceutically acceptable salt thereof.

Another preferred embodiment of the present invention is a compound of Formula I wherein $R^1$ is phenethyl or 1-methyl-2-(phenyl)ethyl, wherein said phenethyl or 1-methyl-2-(phenyl)ethyl is optionally substituted on phenyl with one or two substituents independently selected from halo,$(C_1-C_3)$alkyl or $(C_1-C_3)$alkoxy; $R^2$ is 2-hydroxy-phenyl or 3-hydroxy-pyridin-2-yl, wherein said 2-hydroxy-phenyl or 3-hydroxy-pyridin-2-yl is optionally substituted with one or two substituents independently selected from $(C_1-C_3)$alkyl or halo; $R^3$ is $(C_1-C_6)$alkyl, $(C_3-C_7)$cycloalkyl, $(C_1-C_6)$alkyl-Q, aryl, heteroaryl, or $OR^6$; wherein said $(C_1-C_6)$alkyl, $(C_3-C_7)$cycloalkyl, aryl or heteroaryl is optionally substituted with one to three substituents independently selected from fluoro, cyano, trifluoromethyl, trifluoromethoxy, $(C_1-C_3)$alkyl; $(C_1-C_3)$alkoxy, $NR^7R^8$ or hydroxy; and $R^4$ and $R^5$ are each independently hydrogen or methyl; or a pharmaceutically acceptable salt thereof.

Another preferred embodiment of the present invention is a compound selected from the group consisting of:
2-(2-Hydroxy-phenyl)-3-phenethyl-5-trifluoromethyl-3H-pyrido[4,3-d]pyri-midin-4-one;
2-(3-Fluoro-2-hydroxy-phenyl)-3-phenethyl-5-trifluoromethyl-3H-pyrido[4,3-d]pyrimidin-4-one;
2-(3-Hydroxy-pyridin-2-yl)-3-phenethyl-5-trifluoromethyl-3H-pyrido[4,3-d]pyrimidin-4-one;
(R)-2-(2-Hydroxy-phenyl)-3-(1-methyl-2-phenyl-ethyl)-5-trifluoromethyl-3H-pyrido[4,3-d]pyrimidin-4-one;
(S)-2-(2-Hydroxy-phenyl)-3-(1-methyl-2-phenyl-ethyl)-5-trifluoromethyl-3H-pyrido[4,3-d]pyrimidin-4-one;
(R)-2-(3-Hydroxy-pyridin-2-yl)-3-(1-methyl-2-phenyl-ethyl)-5-trifluoromethyl-3H-pyrido[4,3-d]pyrimidin-4-one;
(R, S)-2-(3-Hydroxy-pyridin-2-yl)-3-(1-methyl-2-(2-fluorophenyl)ethyl)-5-trifluoromethyl-3H-pyrido[4,3-d]pyrimidin-4-one;
(R)-2-(3-Hydroxy-pyridin-2-yl)-3-(1-methyl-2-(2-fluorophenyl)ethyl)-5-trifluoromethyl-3H-pyrido[4,3-d]pyrimidin-4-one;
(S)-2-(3-Hydroxy-pyridin-2-yl)-3-(1-methyl-2-(2-fluorophenyl)ethyl)-5-trifluoromethyl-3H-pyrido[4,3-d]pyrimidin-4-one;
2-(2-Hydroxyphenyl)-3-(2-fluorophenyl)ethyl)-5-trifluoromethyl-3H-pyrido[4,3-d]pyrimidin-4-one;
2-(2-Hydroxyphenyl)-3-(3-fluorophenyl)ethyl)-5-trifluoromethyl-3H-pyrido[4,3-d]pyrimidin-4-one;
2-(3-Fluoro-2-hydroxy-phenyl)-3-[2-(2-fluoro-phenyl)-ethyl]-5-trifluoromethyl-3H-pyrido[4,3-d]pyrimidin-4-one;
2-(2-Hydroxy-phenyl)-7-methyl-3-(phenyl-ethyl)-5-trifluoromethyl-3H-pyrido[4,3-d]pyrimidin-4-one;
2-(3-Fluoro-2-hydroxy-phenyl)-3-[2-(3-fluoro-phenyl)-ethyl]-5-trifluoromethyl-3H-pyrido[4,3-d]pyrimidin-4-one;
3-[2-(2-Fluoro-phenyl)-ethyl]-2-(3-hydroxy-pyridin-2-yl)-5-trifluoromethyl-3H-pyrido[4,3-d]pyrimidin-4-one;
3-[2-(3,4-Difluoro-phenyl)-ethyl]-2-(3-hydroxy-pyridin-2-yl)-5-trifluoromethyl-3H-pyrido[4,3-d]pyrimidin-4-one;
3-[2-(2,4-Difluoro-phenyl)-ethyl]-2-(3-hydroxy-pyridin-2-yl)-5-trifluoromethyl-3H-pyrido[4,3-d]pyrimidin-4-one;
3-[2-(3,4-Difluoro-phenyl)-ethyl]-2-(3-hydroxy-pyridin-2-yl)-5-trifluoromethyl-3H-pyrido[4,3-d]pyrimidin-4-one;
2-(2-Hydroxy-phenyl)-5-methylamino-3-phenethyl-3H-pyrido[4,3-d]pyrimidin-4-one;

2-(2-Hydroxy-phenyl)-5-isopropylamino-3-phenethyl-3H-pyrido[4,3-d]pyrimidin-4-one;
2-(2-Hydroxy-phenyl)-3-phenethyl-5-pyrrolidin-1-yl-3H-pyrido[4,3-d]pyrimidin-4-one;
2-(2-Hydroxy-phenyl)-5-(4-methyl-piperazin-1-yl)-3-phenethyl-3H-pyrido[4,3-d]pyrimidin-4-one;
2-(2-Hydroxy-phenyl)-3-phenethyl-5-piperazin-1-yl-3H-pyrido[4,3-d]pyrimidin-4-one;
5-Dimethylamino-2-(2-hydroxy-phenyl)-3-phenethyl-3H-pyrido[4,3-d]pyrimidin-4-one;
2-(2-Hydroxy-phenyl)-5-morpholin-4-yl-3-phenethyl-3H-pyridin-4-one;
5-Azetidin-1-yl-2-(2-hydroxy-phenyl)-3-phenethyl-3H-pyrido[4,3-]d-pyrimidin-4-one;
2-(2-Hydroxy-phenyl)-3-phenethyl-5-phenyl-3H-pyrido[4,3-d]pyrimidin-4-one;
5-Benzyl-2-(2-hydroxy-phenyl)-3-phenethyl-3H-pyrido[4,3-d]pyrimidin-4-one;
2-(2-Hydroxy-phenyl)-5-methyl-3-phenethyl-3H-pyrido[4,3-d]pyrimidi-4-one;
5-(6-Dimethylamino-pyridin-3-yl)-2-(2-hydroxy-phenyl)-3-phenethyl-3H-pyrido[4,3-d]pyrimidin-4-one;
5-(6-Dimethylamino-5-methyl-pyridin-3-yl)-2-(2-hydroxy-phenyl)-3-phenethyl-3H-pyrido[4,3-d]pyrimidin-4-one;
5-(6-pyrrolidine-5-pyridin-3-yl)-2-(2-hydroxy-phenyl)-3-phenethyl-3H-pyrido[4,3-d]pyrimidin-4-one;
2-(2-Hydroxy-phenyl)-5-methoxy-3-phenethyl-3H-pyrido[4,3-d]pyrimidin-4-one;
2-(2-Hydroxy-phenyl)-5-(1-methyl-cyclopropylmethoxy)-3-phenethyl-3H-pyrido[4,3-d]pyrimidin-4-one;
2-(2-Hydroxy-phenyl)-3-phenethyl-5-propoxy-3H-pyrido[4,3-d]pyrimidin-4-one;
5-Cyclobutyloxy-2-(2-hydroxy-phenyl)-3-phenethyl-3H-pyrido[4,3-d]pyrimidin-4-one;
2-(2-Hydroxy-phenyl)-5-isobutoxy-3-phenethyl-3H-pyrido[4,3-d]pyrimidin-4-one;
2-(2-Hydroxy-phenyl)-5-isopropoxy-3-phenethyl-3H-pyrido[4,3-d]pyrimidin-4-one;
2-(2-Hydroxy-phenyl)-3-phenethyl-5-(2,2,2-trifluoro-ethoxy)-3H-pyrido[4,3-d]pyrimidin-4-one;
3-(1-(3,4-difluorophenyl)propan-2-yl)-2-(3-hydroxypyridin-2-yl) 5-(trifluoromethyl)pyrido[4,3-d]pyrimidin-4(3H)-one;
(R)-3-(1-(3,4-difluorophenyl)propan-2-yl)-2-(3-hydroxypyridin-2-yl) 5-(trifluoromethyl)pyrido[4,3-d]pyrimidin-4(3H)-one;
(S)-3-(1-(3,4-difluorophenyl)propan-2-yl)-2-(3-hydroxypyridin-2-yl) 5-(trifluoromethyl)pyrido[4,3-d]pyrimidin-4(3H)-one;
3-(1-(2,4-difluorophenyl)propan-2-yl)-2-(3-hydroxypyridin-2-yl)-5-(trifluoromethyl)pyrido[4,3-d]pyrimidin-4(3H)-one;
3-(1-(2,4-difluorophenyl)propan-2-yl)-2-(3-hydroxypyridin-2-yl)-5-(trifluoromethyl)pyrido[4,3-d]pyrimidin-4(3H)-one;
3-(2-methoxyphenethyl)-2-(3-hydroxypyridin-2-yl)-5-(trifluoromethyl)pyrido[4,3-d]pyrimidin-4(3H)-one;
3-(2,3-difluorophenethyl)-2-(3-hydroxypyridin-2-yl)-5-(trifluoromethyl)pyrido[4,3-d]pyrimidin-4(3H)-one;
3-(5-fluoro-2-methoxyphenethyl)-2-(3-hydroxypyridin-2-yl)-5-(trifluoromethyl)pyrido[4,3-d]pyrimidin-4(3H)-one;
3-(2-fluoro-6-methoxyphenethyl)-2-(3-hydroxypyridin-2-yl)-5-(trifluoromethyl)pyrido[4,3-d]pyrimidin-4(3H)-one;
2-(3-hydroxypyridin-2-yl)-3-(1-(2-methoxyphenyl)propan-2-yl)-5-(trifluoromethyl)pyrido[4,3-d]pyrimidin-4(3H)-one;
2-(3-hydroxypyridin-2-yl)-3-(1-(2-methoxyphenyl)propan-2-yl)-5-(trifluoromethyl)pyrido[4,3-d]pyrimidin-4(3H)-one;
2-(3-hydroxypyridin-2-yl)-3-(1-(2-methoxyphenyl)propan-2-yl)-5-(trifluoromethyl)pyrido[4,3-d]pyrimidin-4(3H)-one;
3-(1-(2-fluorophenyl)butan-2-yl)-2-(3-hydroxypyridin-2-yl)-5-(trifluoromethyl)pyrido[4,3-d]pyrimidin-4(3H)-one;
3-(3-fluoro-2-methoxyphenethyl)-2-(3-hydroxypyridin-2-yl)-5-(trifluoromethyl)pyrido[4,3-d]pyrimidin-4(3H)-one;
3-(2-cyclopentylethyl)-2-(3-hydroxypyridin-2-yl)-5-(trifluoromethyl)pyrido[4,3-d]pyrimidin-4(3H)-one;
3-(2-cyclohexylethyl)-2-(3-hydroxypyridin-2-yl)-5-(trifluoromethyl)pyrido[4,3-d]pyrimidin-4(3H)-one;
(R)-3-(1-cyclohexylpropan-2-yl)-2-(3-hydroxypyridin-2-yl)-5-(trifluoromethyl)pyrido[4,3-d]pyrimidin-4(3H)-one;
(S)-3-(1-cyclohexylpropan-2-yl)-2-(3-hydroxypyridin-2-yl)-5-(trifluoromethyl)pyrido[4,3-d]pyrimidin-4(3H)-one;
(R, S)-2-(3-hydroxypyridin-2-yl)-3-(2-(tetrahydro-2H-pyran-2-yl)ethyl)-5-(trifluoromethyl)pyrido[4,3-d]pyrimidin-4(3H)-one;
(R)-2-(3-fluoro-2-hydroxyphenyl)-3-(1-phenylpropan-2-yl)-5-(trifluoromethyl)pyrido[4,3-d]pyrimidin-4(3H)-one;
(R)-2-(1H-imidazol-2-yl)-3-(1-phenylpropan-2-yl)-5-(trifluoromethyl)pyrido[4,3-d]pyrimidin-4(3H)-one;
N-(2-(3-(2-fluorophenethyl)-4-oxo-5-(trifluoromethyl)-3,4-dihydropyrido[4,3-d]pyrimidin-2-yl)pyridin-3-yl)acetamide;
(R)-3-(1-phenylpropan-2-yl)-2-(thiazol-4-yl)-5-(trifluoromethyl)pyrido[4,3-d]pyrimidin-4(3H)-one;
3-phenethyl-2-(thiazol-4-yl)-5-(trifluoromethyl)pyrido[4,3-d]pyrimidin-4(3H)-one;
3-(2-methoxyphenethyl)-2-(2-hydroxyphenyl)-5-(trifluoromethyl)pyrido[4,3-d]pyrimidin-4(3H)-one;
3-(2-fluorophenethyl)-2-(thiazol-4-yl)-5-(trifluoromethyl)pyrido[4,3-d]pyrimidin-4(3H)-one;
(R)-2-cyclopentyl-3-(1-phenylpropan-2-yl)-5-(trifluoromethyl)pyrido[4,3-d]pyrimidin-4(3H)-one;
2-isopropyl-3-phenethyl-5-(trifluoromethyl)pyrido[4,3-d]pyrimidin-4(3H)-one
2-cyclopentyl-3-phenethyl-5-(trifluoromethyl)pyrido[4,3-d]pyrimidin-4(3H)-one;
3-(2-methoxyphenethyl)-2-(thiazol-4-yl)-5-(trifluoromethyl)pyridin-4(3H)-one;
3-(2-cyclohexylethyl)-2-(thiazol-4-yl)-5-(trifluoromethyl)pyrido[4,3-d]pyrimidin-4(3H)-one;
2-(3-(2-cyclohexylethyl)-4-oxo-5-(trifluoromethyl)-3,4-dihydropyrido[4,3-d]pyrimidin-2-yl)benzonitrile;
2-(3-aminopyridin-2-yl)-3-phenethyl-5-(trifluoromethyl)pyrido[4,3-d]pyrimidin-4(3H)-one;
N-(2-(4-oxo-3-phenethyl-5-(trifluoromethyl)-3,4-dihydropyrido[4,3-d]pyrimidin-2-yl)pyridin-3-yl)methanesulfonamide;
3-(1-(2-fluorophenyl)propan-2-yl)-2-(thiazol-4-yl)-5-(trifluoromethyl)pyrido[4,3-d]pyrimidin-4(3H)-one;
2-(3-hydroxypyridin-2-yl)-3-isopentyl-5-(trifluoromethyl)pyrido[4,3-d]pyrimidin-4(3H)-one;

2-(3-hydroxypyridin-2-yl)-3-((tetrahydro-2H-pyran-4-yl) methyl)-5-(trifluoromethyl)pyrido[4,3-d]pyrimidin-4 (3H)-one;

2-(3-hydroxypyridin-2-yl)-3-(2-(tetrahydro-2H-pyran-4-yl) ethyl)-5-(trifluoromethyl)pyrido[4,3-d]pyrimidin-4(3H)-one;

3-(2-fluoro-5-methoxyphenethyl)-2-(3-hydroxypyridin-2-yl)-5-(trifluoromethyl)pyrido[4,3-d]pyrimidin-4(3H)-one;

3-(2-fluoro-3-methoxyphenethyl)-2-(3-hydroxypyridin-2-yl)-5-(trifluoromethyl)pyrido[4,3-d]pyrimidin-4(3H)-one;

2-(3-(2-fluorophenethyl)-4-oxo-5-(trifluoromethyl)-3,4-dihydroquinazolin-2-yl)benzonitrile N-(2-(3-(2-fluorophenethyl)-4-oxo-5-(trifluoromethyl)-3,4-dihydropyrido[4,3-d]pyrimidin-2-yl)pyridin-3-yl)-2,2,2-trifluoroacetamide;

(R)-2,2,2-trifluoro-N-(2-(4-oxo-3-(1-phenylpropan-2-yl)-5-(trifluoromethyl)-3,4-dihydropyrido[4,3-d]pyrimidin-2-yl)pyridin-3-yl)acetamide;

3-cyclohexyl-2-(3-hydroxypyridin-2-yl)-5-(trifluoromethyl)pyrido[4,3-d]pyrimidin-4(3H)-one 3-(cyclohexylmethyl)-2-(3-hydroxypyridin-2-yl)-5-(trifluoromethyl)pyrido[4,3-d]pyrimidin-4(3H)-one;

3-Phenethyl-5-trifluoromethyl-2-(3-trifluoromethyl-pyridin-2-yl)-3H-pyrido[4,3-d]pyrimidin-4-one;

2-(5-aminothiazol-4-yl)-3-phenethyl-5-(trifluoromethyl)pyrido[4,3-d]pyrimidin-4(3H)-one;

2-(2-(difluoromethyl)phenyl)-3-phenethyl-5-(trifluoromethyl)pyrido[4,3-d]pyrimidin-4(3H)-one;

2-(3-(difluoromethyl)pyridin-2-yl)-3-phenethyl-5-(trifluoromethyl)pyrido[4,3-d]pyrimidin-4(3H)-one;

3-(2-cyclohexylethyl)-5-(trifluoromethyl)-2-(2-(trifluoromethyl)phenyl)pyrido[4,3-d]pyrimidin-4(3H)-one; and 3-(2-cyclohexylethyl)-5-(trifluoromethyl)-2-(3-(trifluoromethyl)pyridin-2-yl)pyrido[4,3-d]pyrimidin-4(3H)-one; or a pharmaceutically acceptable salt thereof.

Another embodiment of the present invention is a pharmaceutical composition comprising a compound according to Formula I as described in any of the preceding embodiments hereinabove and a pharmaceutically acceptable carrier, adjuvant or diluent.

Another embodiment of the present invention are novel intermediate compounds 4-Amino-2-(trifluoromethyl)nicotinic acid or 4-Amino-2-chloronicotinic acid; or a pharmaceutically acceptable salt thereof.

Another embodiment of the present invention is a method of treating a disease or disorder characterized by abnormal bone or mineral homeostasis which comprises the administration to a patient in need of treatment thereof a therapeutically effective amount of a compound according to Formula I as described in any of the preceding embodiments hereinabove. A preferred embodiment of the present invention is the method according to the preceding embodiment wherein the disease or disorder characterized by abnormal bone or mineral homeostasis is selected from the group consisting of osteoporosis, osteopenia, periodontal disease, Paget's disease, bone fracture, osteoarthritis, rheumatoid arthritis, and humoral hypercalcemia of malignancy. Yet another preferred embodiment is the method according to the preceding embodiment wherein the disease or disorder characterized by abnormal bone or mineral homeostasis is osteoporosis.

The following reaction schemes, Reaction Schemes I-IV, depict methods of synthesis for compounds of formula I. In the following general methods for preparation of the compounds of formula I the variables $R^1$, $R^2$, $R^3$, $R^4$, and $R^5$, are as previously defined for a compound of the formula I unless otherwise stated. The Reaction Schemes herein described are intended to provide a general description of the methodology employed in the preparation of many of the Examples given. However, it will be evident from the detailed descriptions given in the Experimental section that the modes of preparation employed extend further than the general procedures described herein. In particular it is noted that the compounds prepared according to these Schemes may be modified further to provide new Examples within the scope of this invention. The reagents and intermediates used in the following examples are either commercially available or can be prepared according to standard literature procedures by those skilled in the art of organic synthesis.

Reaction Scheme I, below, depicts the synthesis of intermediates of formula V which are useful for preparing compounds of formula I. Treatment of an appropriately substituted pyridine of formula IX with an appropriate base, such as lithium diisopropylethylamide, in an appropriate solvent, such as THF, at approximately −65° C. to −78° C. followed by addition of $CO_2$ and acidification upon workup provides the corresponding nicotinic acid of formula VIII. Treatment of the appropriately substituted nicotinic acid of formula VIII with an appropriate base, such as n-butyl lithium and lithium 2,2,6,6-tetramethylpiperidide (LiTMP), followed by trapping with an appropriate halogen source, such as hexachloroethane, and followed by esterification, with diazomethane for example, provides the corresponding chlorinated pyridine ester of formula VII. The chlorinated pyridine ester VII is then treated with an appropriate nitrogen source, such as azide anion (i.e. sodium azide) in an appropriate solvent, such as DMF, typically at 40° C. to 50° C. for 1 to 24 hours, to provide the azido pyridine ester of formula VI [Cf: Kiyama, *Chem. Pharm. Bull.* 1995, 43, 450.]. Reduction of the azide group in the compound of formula VI to the corresponding amine can be carried out using several procedures known in the art, such as catalytic hydrogenation, treatment with aqueous hydriodic acid at ambient temperature or treatment with triphenylphosphine. Saponification of the ester can then be carried out in a variety of ways such as aqueous lithium hydroxide in an appropriate solvent such as dioxane:MeOH:water (3:2:1) at a temperature of 40° C. to 100° C., preferably at approximately 85° C. for 1 to 24 hours to provide the corresponding nicotinic acid of formula V. It is to be appreciated that the group $R^3$ in the compounds of formulae IX, VIII, VII, VI and V can have the same meaning as defined for group $R^3$ in compounds of formula I or alternatively can be a functionality that can be converted to a group $R^3$ as defined for compounds of formula I. For example, $R^3$ in formulae IX, VIII, VII, VI and V can be a halo group, such as chloro, which can then be further converted, for example, as shown in Reaction Scheme VI, below to a group $R^3$ as defined for a compound of formula I.

Reaction Scheme I

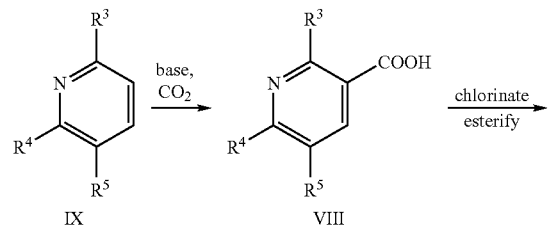

-continued

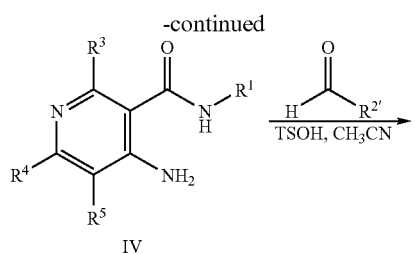

VII

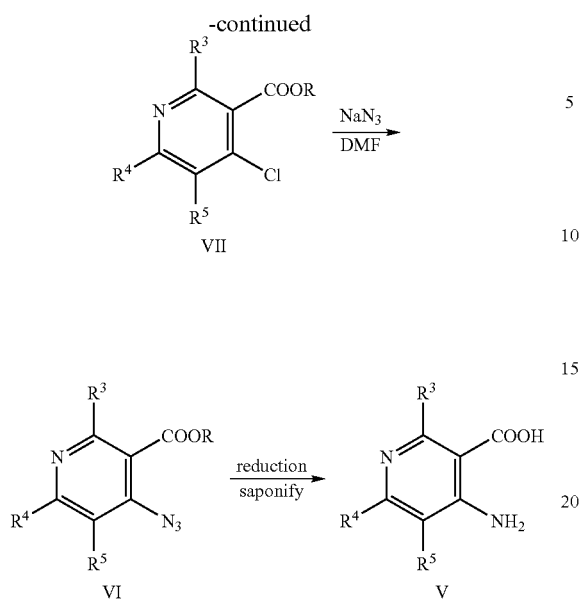

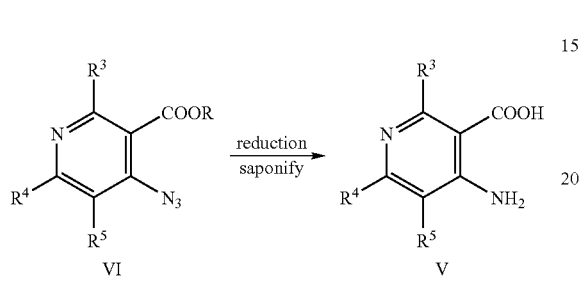

VI        V

Reaction Scheme II, below, depicts the preparation of compounds of Formula I. Formula IV compounds are prepared by reacting the corresponding acid of Formula V with a variety of primary amines of general formula $R^1NH_2$ under standard amide coupling conditions for a period between 4 to 24 hours. Formula III compounds are prepared by reaction of Formula IV compounds with an appropriate aldehyde, $R^{2'}CHO$, in the presence of a catalytic amount of an acid, such as p-toluenesulfonic acid, in a suitable reaction inert solvent such as acetonitrile or toluene at a temperature between 55° C. to 100° C., typically 80° C., for a period between 1 to 24 hours. The $R^{2'}$ moiety in the aldehyde of formula $R^{2'}CHO$ is one in which a protected hydroxy group typically exists, such as a methoxy or benzyloxy, which can subsequently be deprotected to the free hydroxy present in group $R^2$ in the compound of Formula I. Compounds of Formula III are then treated with an oxidizing agent such as potassium permanganate in a polar solvent such as acetone at a temperature between 20° C. to 50° C., typically ambient temperature, to provide compounds of Formula II after a period of 1 to 24 hours. Compounds of Formula II which contain a protected hydroxy group such as a suitable methyl ether moiety or benzyloxy moiety, may be converted to the free hydroxy (such as a phenolic hydroxy group) by standard deprotection conditions.

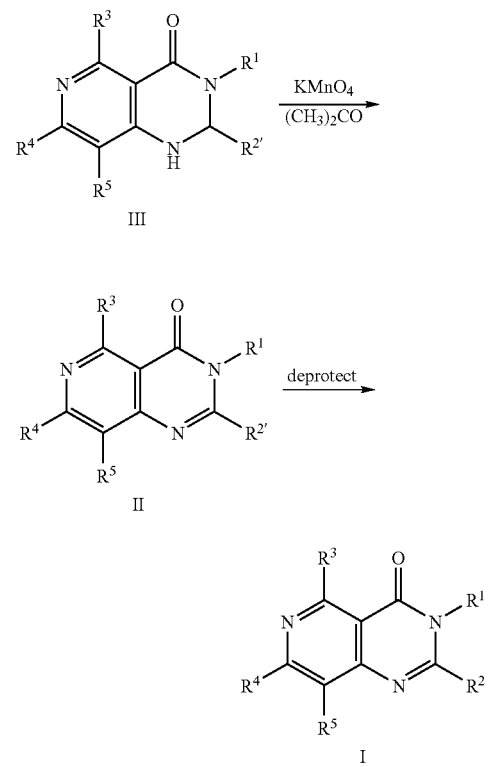

In the reaction schemes described herein it is to be understood that hydroxy groups in intermediates useful for preparing compounds of Formula I may be protected by other conventional protecting groups known to those skilled in the art. For example, intermediates containing a hydroxy group may be protected as the corresponding benzyloxy ether and subsequently deprotected by hydrogenation to provide the free hydroxy derivative. Suitable protecting groups and methods for their removal are illustrated in *Protective Groups in Organic Synthesis,* $3^{rd}$ Ed., Theodora W. Greene, and Peter G. M. Wuts (John Wiley & Sons, 1999). For example, in cases where the compound of formula II contains a suitable methyl ether moiety, the compound of Formula II is dissolved in a suitable solvent such as methylene chloride at a temperature between −78° C. to 10° C. followed by the addition of boron trichloride or boron tribromide. The reaction mixture is stirred at 10° C. to 50° C. for 1 to 24 hours to provide the desired deprotected compound of Formula I. Similarly, compounds of formula II containing a suitable benzyloxy moiety can be deprotected to provide compounds of formula I by hydrogenation, such as H-cube hydrogenation (Pd/C cartridge) carried out at ambient temperature using methanol as solvent.

Reaction Scheme II

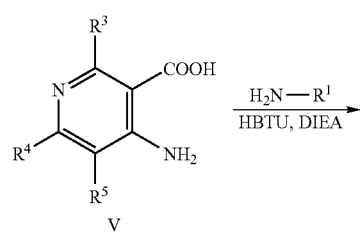

V

Reaction Scheme III

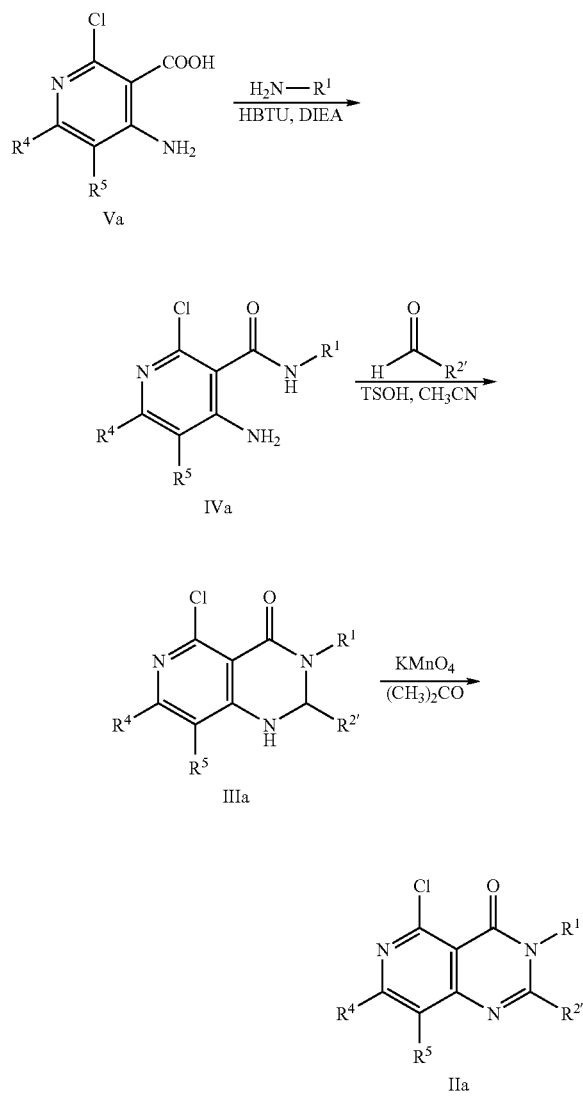

Reaction Scheme IV

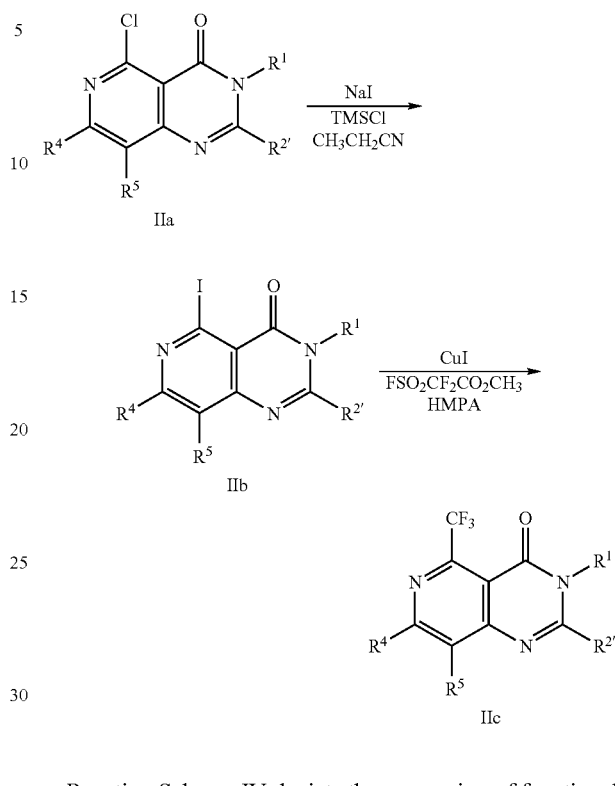

Reaction Scheme IV depicts the conversion of functional groups at the $R^3$ position of various intermediates useful in preparing compounds of Formula I. Formula IIa compounds, wherein $R^3$ is chloro, are converted to Formula IIb compounds, wherein $R^3$ is iodo, by reaction with a reagent such as sodium iodide and trimethylsilyl chloride in the dark in an inert solvent such as acetonitrile or propionitrile at a temperature between 55° C. to 120° C., typically 100° C., for a period between 1 to 24 hours. The compounds of Formula IIc are prepared by reacting the compounds of Formula IIb with methyl-2,2-difluoro-2-(fluoro-sulfonyl)acetate and copper iodide in a mixture of solvent such as HMPA and DMF at a temperature between 55° C. to 120° C., typically 80° C., for a period between 1 to 24 hours. The $R^2$ group in the compounds of formulae IIa, IIb and IIc is one in which a protected hydroxy group exists, such as a methoxy or benzyloxy, which can subsequently be deprotected to the free hydroxy present in group $R^2$ of the corresponding compound within formula I.

Reaction Scheme III depicts Formula IVa compounds prepared by reacting the corresponding acid of Formula Va with a variety of primary amines of general formula $R^1NH_2$ under standard amide coupling conditions for a period between 4 to 24 hours. Formula IIIa compounds may be prepared by reaction of Formula IVa compounds with an appropriate aldehyde, $R^{2'}CHO$, in the presence of a catalytic amount of an acid, such as p-toluenesulfonic acid, in a suitable reaction inert solvent such as acetonitrile or toluene at a temperature between 55° C. to 100° C., typically 80° C., for a period between 1 to 24 hours. The $R^{2'}$ moiety in the aldehyde of formula $R^{2'}CHO$ is one in which a protected hydroxy group exists, such as a methoxy or benzyloxy, which can subsequently be deprotected to the free hydroxy present in group $R^2$ in the compound of formula I. Compounds of Formula IIIa are then treated with an oxidizing agent such as potassium permanganate in a polar solvent such as acetone at a temperature between 20° C. to 50° C., typically ambient to provide compounds of Formula IIa after a period of 1 to 24 hours.

Reaction Scheme V

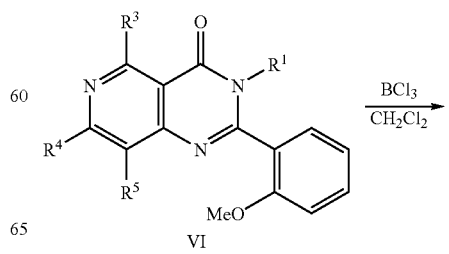

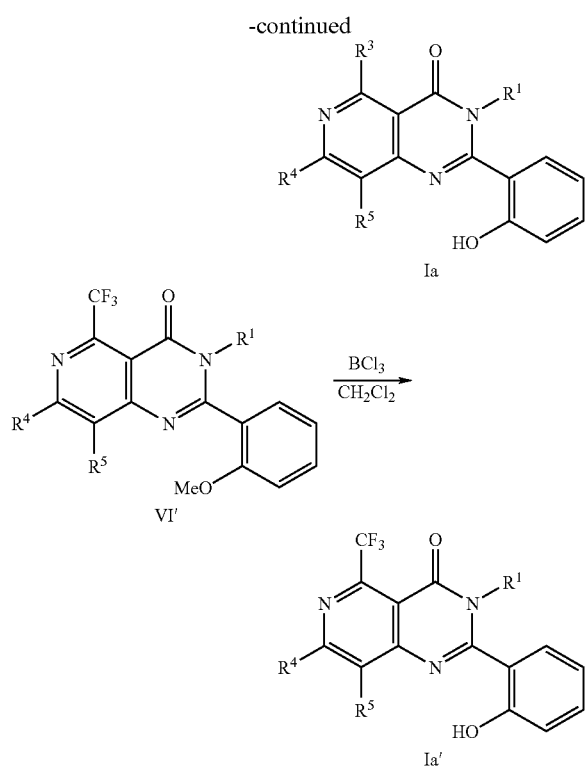

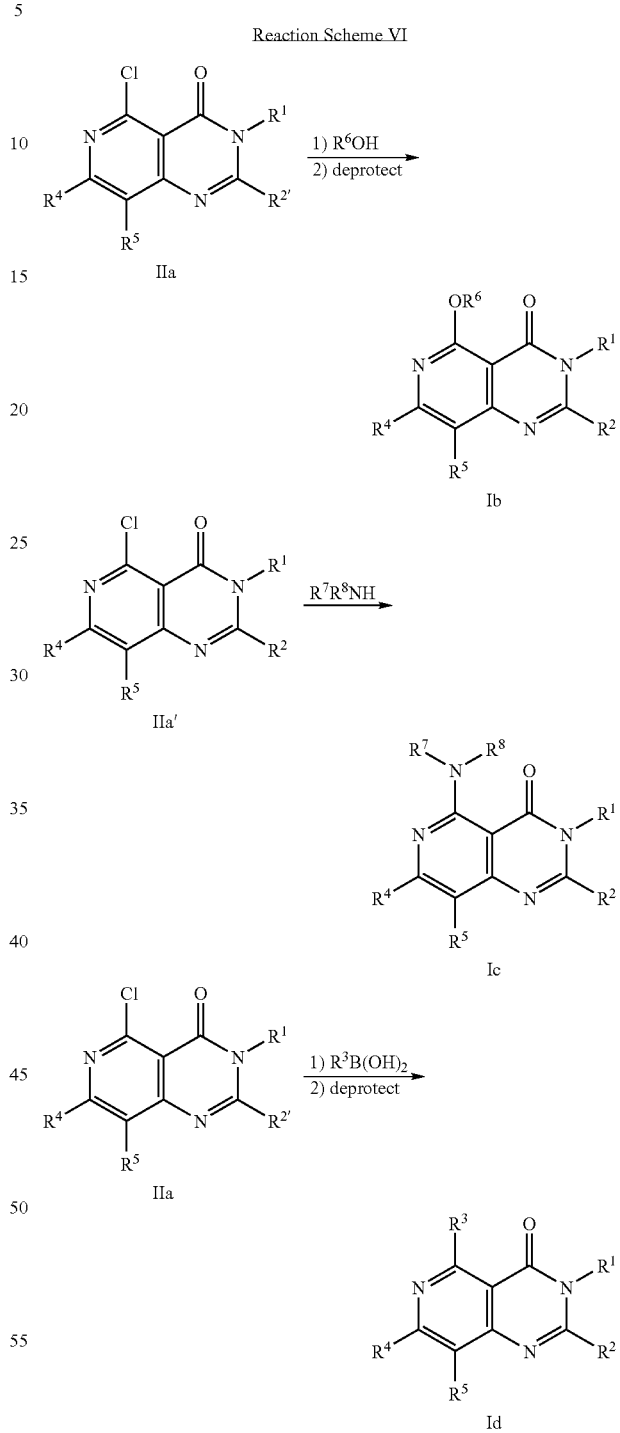

Reaction Scheme V depicts the conversion of a methyl ether moiety in certain intermediates of formulae VI or VI' wherein $R^2$ is 2-methoxyphenyl, to a free phenolic hydroxy moiety in compounds of Formula Ia or Ia'. Compounds of Formula VI (or VI' in which $R^3$ is $CF_3$) which contain a methyl ether moiety may be converted to the free phenol by dissolving the compounds of Formula VI or VI' in a suitable solvent such as methylene chloride at a temperature between −78° C. to 10° C. followed by the addition of boron trichloride or boron tribromide. The reaction mixture is stirred at 10° C. to 50° C. for 1 to 24 hours to provide the desired compounds, such as those of Formula Ia or Ia'.

Reaction Scheme VI, below, depicts three reactions showing the conversion of chloro derivative IIa or IIa' to alkoxy (Ib, wherein $R^3$ is $OR^6$), amino (Ic, wherein $R^3$ is $NR^7R^8$) and carbon-linked derivatives (Id, wherein $R^3$ results from an appropriate boronic acid derivative such as an aryl, heteroaryl or ($C_1$-$C_6$)alkyl boronic acid), respectively. Compounds of Formula IIa may be converted to compounds of Formula Ib by treatment of the corresponding alcohol, $R^6OH$, in the presence of a suitable base such as sodium hydride in an inert solvent such as DMF or THF at 20° C. to 80° C. for 6 to 24 hours, followed by deprotection as necessary to provide compounds of Formula Ib.

Compounds of Formula IIa', in which the hydroxy moiety in $R^2$ is in deprotected form, may be reacted with an appropriate amine of formula $R^7R^8NH$ in a solvent such as methanol or ethanol at 20° C. to 80° C. for 1 to 24 hours to provide compounds of Formula Ic. Compounds of Formula IIa may also be treated with an appropriate corresponding boronic acid derivative of formula $R^3B(OH)_2$ in the presence of a catalyst such as palladium tetrakis(triphenylphosphine) in a mixture of aqueous sodium carbonate and a polar solvent such as dioxane in a microwave for 1 to 25 minutes at 50° C. to 150° C., followed by deprotection as necessary to provide compounds of Formula Id.

The term "patient in need of treatment thereof" means humans and other animals who have or are at risk of having a disease or disorder characterized by abnormal bone or mineral homeostasis. The "patient in need of treatment thereof" may have or be at risk of having a disease or disorder characterized by abnormal bone or mineral homeostasis selected from the group consisting of osteoporosis, osteopenia, periodontal disease, Paget's disease, bone fracture, osteoarthritis, rheumatoid arthritis, and humoral hypercalcemia of malignancy. As certain of the conditions being treated have a higher incidence in females a preferred patient is a female, and particularly a postmenopausal female human.

The term "treating", "treat" or "treatment" as used herein includes preventative (e.g., prophylactic), palliative, adjuvant and curative treatment. For example, the treatment of osteoporosis, as used herein means that a patient having osteoporosis or at risk of having osteoporosis can be treated according to the methods described herein. For patients undergoing preventative treatment, a resulting reduction in the incidence of the disease state being preventively treated is the measurable outcome of the preventative treatment.

The present invention provides methods of treating osteopenia and osteoporosis by administering to a patient in need thereof a therapeutically effective amount of a compound of formula I. Osteopenia is a thinning of the bones, but less than is seen with osteoporosis and is the stage before true osteoporosis. The World Health Organization has developed diagnostic categories based on bone mass density (BMD) to indicate if a person has normal bones, has osteopenia or has osteoporosis. Normal bone density is within one standard deviation (+1 or −1) of the young adult mean bone density. Osteopenia (low bone mass) is defined as bone density of 1 to 2.5 standard deviations below the young adult mean (−1 to −2.5), and osteoporosis is defined as a bone density that is 2.5 standard deviations or more below the young adult mean (>−2.5).

The present invention provides methods of treating bone fractures by administering to a patient in need thereof a therapeutically effective amount of a compound of formula I. Bone fractures can be a fracture to any bone in the body, and hip fracture being of particular concern. Hip fracture has a significant impact on medical resources and patient morbidity and mortality. Few patients admitted with a hip fracture are considered for prophylactic measures aimed at the reduction of further fracture risk. Currently, 10-13% of patients will later sustain a second hip fracture. Of patients who suffered a second hip fracture, fewer patients maintained their ability to walk independently after the second fracture than did so after the first (53 and 91% respectively, P<0.0005). Pearse E. O. et al., $Injury$, 2003, 34(7), 518-521. Following second hip fracture, patients' level of mobility determined their future social independence. Older patients and those with a history of multiple falls had a shorter time interval between fractures. Second hip fracture has a significant further impact on patients' mobility and social independence. It is therefore desirable to have new methods for the treatment of bone fractures including hip fracture.

The compounds of Formula I can be administered together with additional agents which are useful for treating a disease or disorder characterized by abnormal bone or mineral homeostasis. Particularly contemplated additional agents include calcium receptor antagonists other than those of Formula I, selective estrogen receptor modulators (SERMs), bisphosphonates, parathyroid hormone (PTH) and fragments and analogues thereof, estrogens, calcitonins, synthetic steroids, synthetic isoflavones, vitamin D analogues, vitamin K analogues, strontium salts, cathepsin K inhibitors, $\alpha_v\beta_3$ integrin (vitronectin) antagonists, prostaglandin (PGE2) receptor agonists and receptor activator of nuclear factor κB ligand (RANKL) inhibitors.

Additional calcium receptor antagonists that can be used together with compounds of Formula I in the methods and compositions of this invention include those described in PCT International Publication Nos. WO 93/04373; WO 94/18959; WO 95/11211; WO 97/37967; WO 98/44925; WO 98/45255; WO 99/51241; WO 99/51569; WO 00/45816; WO 02/14259; WO 02/38106; WO 2004/041755; and WO 2005/030746; Nemeth, E. F.; $Journal\ of\ Molecular\ Endocrinology$ (2002) 29, 15-21; Kessler, A. et al.; $ChemBioChem$ (2004) 5, 1131; Steddon, S. J. et al.; $Lancet$ (2005) 365, 2237-2239; and Shcherbakova, I.; et al.; $Bioorganic\ \&\ Medicinal\ Chemistry\ Letters$ (2005) 15, 1557-1560. Specific calcilytic compounds that can be used together with compounds of Formula I in the methods and compositions of this invention include NPS-2143 and 423562.

SERMs that can be used together with compounds of Formula I in the methods and compositions of this invention include, but are not limited to, lasofoxifene (Oporia®), raloxifene (Evista®), arzoxifene, bazedoxifene, ospemifene, Chiesi's CHF-4227 and Prostrakan's PSK-3471. Bisphosphonates that can be used together with compounds of Formula I in the methods and compositions of this invention include, but are not limited to, tiludronate (Skelid®), clondronate (Bonefos®), etidronate (Didronel®), alendronate (Fosamax®), risedronate (Actonel®), ibandronate (Boniva®), zoledronate (Zometa®), minodronate (Onobis®), neridronate and pamidronate.

In humans, PTH is an 84 amino acid polypeptide produced by the parathyroid gland that controls serum calcium levels through its action on various cells. Several N-terminal amino acids fragments of PTH, including the 1-31, 1-34 and 1-38 fragments (PTH-related proteins; "PTHrP") are considered biologically equivalent to the full length hormone. Parathyroid hormone (PTH) and fragments and analogues thereof that can be used together with compounds of Formula I in the methods and compositions of this invention include, but are not limited to, the full length PTH (such as PTH 1-84, Preos®/Preotact®, Unigene's 768974, Bone Medical's BN-003), the 1-31 (such as Zelos Therapeutics' Ostabolin-C), 1-34 (such as teriparatide, Forteo®, or Ipsen's BIM-44058) or 1-38 fragments.

Estrogens that can be used together with compounds of Formula I in the methods and compositions of this invention include, but are not limited to, estradiol, conjugated equine estrogens (Wyeth's Premarin®) or other estrogens.

Calcitonin is a 32 amino-acid peptide hormone produced by the thyroid gland which inhibits osteoclast activity by binding to calcitonin receptors on the surface of those cells. Calcitonins that can be used together with compounds of Formula I in the methods and compositions of this invention include, but are not limited to, human calcitonin or salmon or eel calcitonins. The calcitonins may be used as injectable or intranasal formulations such as Miacalcin®, Miacalcic®, Calcitonia®, Fortical® or Elcitonin® or as oral formulations such as Novartis' SMC-021, Bone Medical's BN-002 (Capsitonin®) or Nobex's NCT-025 (Oratonin®).

Synthetic steroids that can be used together with compounds of Formula I in the methods and compositions of this invention include, but are not limited to, mixed estrogen and progesterone agonists such as tibolone which is marketed as Livial®. Synthetic isoflavones are chemically synthesized derivatives of plant isoflavones, such as phytoestrogens extracted from soy products. A synthetic isoflavone that can be used together with compounds of Formula I in the methods and compositions of this invention includes, but is not limited to, ipraflavone which is marketed by Takeda as Iprosten® and Osten®.

Vitamin D analogues are compounds that act by binding to the nuclear vitamin D receptor in osteoblasts. Vitamin D analogues that can be used together with compounds of Formula I in the methods and compositions of this invention include, but are not limited to, Chugai's ED-71 and Deltanoid's 2MD.

A strontium salt that can be used together with compounds of Formula I in the methods and compositions of this invention includes, but is not limited to, strontium ranelate (Servier's Protelos®). Cathepsin K inhibitors that can be used together with compounds of Formula I in the methods and compositions of this invention include, but are not limited to, Novartis's AAE-581, balicatib, GlaxoSmithKline's SB-462795 and Merck's c-3578. An $\alpha_v\beta_3$ integrin (vitronectin) antagonist that can be used together with compounds of Formula I in the methods and compositions of this invention includes, but is not limited to, Merck's MRL-123.

Prostaglandin E2 (PGE2) receptor agonists that can be used together with compounds of Formula I in the methods and compositions of this invention include, but are not limited to, PGE2 subtype 2 (EP2) receptor agonists, such as (3-{[4-Tert-butyl-benzyl)-(pyridine-3-sulfonyl)-amino]-methyl}-phenoxy)-acetic acid, or a pharmaceutically acceptable salt thereof or PGE2 subtype 4 (EP4) receptor agonists, such as ONO-4819. A receptor activator of nuclear factor κB ligand (RANKL) inhibitor that can be used together with compounds of Formula I in the methods and compositions of this invention includes, but is not limited to, Amgen's RANKL antibody AMG-162.

Specific combinations of particular interest include compounds of Formula I and lasofoxifene or compounds of Formula I and (3-{[4-Tert-butyl-benzyl)-(pyridine-3-sulfonyl)-amino]-methyl}-phenoxy)-acetic acid, or a pharmaceutically acceptable salt thereof.

Compounds of the invention intended for pharmaceutical use may be administered as crystalline or amorphous products. The compounds may be obtained, for example, as solid plugs, powders, or films by methods such as precipitation, crystallization, freeze drying, spray drying, or evaporative drying. Microwave or radio frequency drying may be used for this purpose.

For the above-mentioned therapeutic uses, the dosage administered will, of course, vary with the compound employed, the mode of administration, the treatment desired and the disorder indicated. The total daily dosage of the compound of formula II/salt/solvate (active ingredient) will, generally, be in the range from 1 mg to 1 gram, preferably 1 mg to 250 mg, more preferably 10 mg to 100 mg. The total daily dose may be administered in single or divided doses. The present invention also encompasses sustained release compositions.

The pharmaceutical composition may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a compound according to the invention as an active ingredient. In addition, it may include other medicinal or pharmaceutical agents, carriers, adjuvants, etc. The dissolution rate of poorly water-soluble compounds may be enhanced by the use of a spray-dried dispersion, such as those described by Takeuchi, H., et al. in "Enhancement of the dissolution rate of a poorly water-soluble drug (tolbutamide) by a spray-drying solvent depostion method and disintegrants" *J. Pharm. Pharmacol.*, 39, 769-773 (1987).

Exemplary parenteral administration forms include solutions or suspensions of active compounds in sterile aqueous solutions, for example, aqueous propylene glycol or dextrose solutions. Such dosage forms can be suitably buffered, if desired.

Suitable pharmaceutical carriers include inert diluents or fillers, water and various organic solvents. The pharmaceutical compositions may, if desired, contain additional ingredients such as flavorings, binders, excipients and the like. Thus for oral administration, tablets containing various excipients, such as citric acid may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Preferred materials, therefor, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof. Methods of preparing various pharmaceutical compositions with a specific amount of active compound are known, or will be apparent, to those skilled in this art. For examples, see *Remington's Pharmaceutical Sciences*, Mack Publishing Company, Easter, Pa., 15th Edition (1975).

Dosage regimens may be adjusted to provide the optimum desired response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form, as used herein, refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the chemotherapeutic agent and the particular therapeutic or prophylactic effect to be achieved, and (b) the limitations inherent in the art of compounding such an active compound for the treatment of sensitivity in individuals. Thus, the skilled artisan would appreciate, based upon the disclosure provided herein, that the dose and dosing regimen is adjusted in accordance with methods well-known in the therapeutic arts. That is, the maximum tolerable dose can be readily established, and the effective amount providing a detectable therapeutic benefit to a patient may also be determined, as can the temporal requirements for administering each agent to provide a detectable therapeutic benefit to the patient. Accordingly, while certain dose and administration regimens are exemplified herein, these examples in no way limit the dose and administration regimen that may be provided to a patient in practicing the present invention.

It is to be noted that dosage values may vary with the type and severity of the condition to be alleviated, and may include single or multiple doses. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition. For example, doses may be adjusted based on pharmacokinetic or pharmacodynamic parameters, which may include clinical effects such as toxic effects and/or laboratory values. Thus, the present invention encompasses intra-patient dose-escalation as determined by the skilled artisan. Determining appropriate dosages and regiments for administration of the chemotherapeutic agent are well-known in the relevant art and would be understood to be encompassed by the skilled artisan once provided the teachings disclosed herein.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents. Particularly contemplated additional agents include selective estrogen receptor modulators (SERMs), bisphosphonates, parathyroid hormone (PTH) and fragments and analogues thereof, estrogens, calcitonins, synthetic steroids, synthetic isoflavones, vitamin D analogues, vitamin K analogues, strontium salts, cathepsin K inhibitors, $\alpha_v\beta_3$ integrin (vitronectin) antagonists, prostaglandin (PGE2) receptor agonists and receptor activator of nuclear factor κB ligand (RANKL) inhibitors, such as those described hereinabove.

Controlled- or sustained-release formulations of a pharmaceutical composition of the invention may be made using conventional technology.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations as discussed below. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition.

A composition of the present invention can be administered by a variety of methods known in the art. The route and/or mode of administration vary depending upon the desired results. The active compounds can be prepared with carriers that protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are described by e.g., Sustained and Controlled Release Drug Delivery Systems, J. R. Robinson, ed., Marcel Dekker, Inc., New York, (1978). Pharmaceutical compositions are preferably manufactured under GMP conditions.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

While the precise dosage administered of each active ingredient will vary depending upon any number of factors, including but not limited to, the type of animal and type of disease state being treated, the age of the animal and the route(s) of administration. The amounts of various CaR antagonist compounds of formula I to be administered can be determined by standard procedures taking into account factors such as the compound $IC_{50}$, $EC_{50}$, the biological half-life of the compound, the age, size and weight of the patient, and the type of condition or symptom associated with the patient. The importance of these and other factors to be considered are known to those of ordinary skill in the art.

PTH secretion can be measured using techniques known in the art (see, e.g., U.S. Pat. No. 6,031,003, hereby incorporated by reference). For example, PTH secretion can be measured by first suspending cells in parathyroid cell buffer containing 0.5 mM $CaCl_2$ and 0.1% bovine serum albumin. Incubations can be performed in plastic tubes (Falcon 2058) containing 0.3 mL of the cell suspension with or without small volumes of $CaCl_2$ and/or organic polycations. After incubation at 37° C., typically 30 minutes, the tubes can then be placed on ice and the cells pelleted at 2° C. Samples of the supernatant should then be brought to pH 4.5 with acetic acid and, if needed, stored at −70° C. The amount of PTH in bovine cell supernatants can be determined by a homologous radioimmunoassay using GW-1 antibody or its equivalent at a final dilution of 1/45,000. 125I-PTH (65-84; INCSTAR, Stillwater, Minn.) can be used as tracer and fractions separated by dextran-activated charcoal. Counting of samples and data reduction can be performed on a Packard Cobra 5005 gamma counter. For testing PTH levels in human cell supernatants, a commercially available radioimmunoassay kit (INS-PTH; Nichols Institute, Los Angeles, Calif.) which recognizes intact and N-terminal human PTH is preferable because GW-1 antibody recognizes human PTH poorly.

In addition, specific assays useful for evaluating the compounds of Formula I include the FLIPR Assay for Evaluating the Potency and Selectivity of Test Compounds; Assay for Evaluating the Effects of Test Compounds on Endogenous PTH Secretion; Evaluation of Effects of Test Compounds on PTH Secretion In Vivo; Effect of Calcium Receptor Antagonist Compound of Formula I on Body Weight, Body Composition and Bone Density in the Aged Intact and Ovariectomized Female Rat; and Fracture Healing Assays as described below.

FLIPR Assay for Evaluating the Potency and Selectivity of Test Compounds

Human kidney cell (HEK 293) expressing the calcium receptor (CasR) are used to detect antagonists of the receptor using Fluorometric imaging plate reader (FLIPR, Molecular Devices, Sunnyvale Calif.). Receptor activation by extracellular calcium results in the release of calcium from intracellular stores into the cytosol. A fluorescent indicator (Fluo-4) is internalized by the cells from growth media and interacts with calcium released into the cytosol to provide a means of quantifying intracellular $Ca^{2+}$ levels and receptor agonism/antagonism. Fluorescence intensity is detected by the FLIPR CCD camera and traced as a function of time. Potential antagonists are identified by their ability to decrease this fluorescent response.

To determine the $IC_{50}$ values cells are loaded with Fluo4 (2.05 mM Fluo-4, 0.04% pluronic acid, 2.6 mM probenecid in 90% DMEM high glucose, 10% dialyzed Fetal Bovine Serum, 1× Pen Strep, 1×L-Glutamine, 3 ug/ml Puromycin, 27.5 nM Methotrexate) for 1 hour at 37° C. Prior to the addition of test compound cells are washed with a 10 mM HEPES buffer solution. The test compound, for example the compound of Example 1, is added at various doses (from 1 □M to 3 nM) and pre-incubated with cells for 30 minutes followed by stimulation of the CasR by the addition of 1.7 mM $Ca^{2+}$. $IC_{50}$ values are based on the ability of the cells to inhibit the $Ca^{2+}$ induced increase in intracellular $Ca^{2+}$. Fluorescence signal is read 42 seconds after the stimulation of the CasR by the addition of 1.7 mM $Ca^{2+}$.

Assay for Evaluating the Effects of Test Compounds on Endogenous PTH Secretion

Adult male or female Sprague-Dawley rats (Charles River Laboratories, Wilmington, Mass.) with jugular vein catheter are used in this assay. The test compounds at various doses are given to the animals by various routes of administration including subcutaneous injection, or intraveneous injection. Serum or plasma PTH concentrations are examined before and after dosing at various times using a commercially available rat intact PTH ELISA kit (Immutopics, Inc. San Clemente, Calif. Cat. #60-2500).

Evaluation of Effects of Test Compounds on PTH Secretion In Vivo

Overnight fasted male Sprague-Dawley rats (250 g) with jugular vein catheter are used in this study. Whole blood sample is collected from each animal prior to compound treatment for measuring baseline PTH concentrations. The test animals are then given a single dose of the tested compound at 1 mg/kg in glycerol formal: 2% DMSO by intravenous administration via jugular vein. Whole blood samples are collected at 2, 5, 15, 30 and 45 minutes, and 1, 2, 3, 4, 6 and 8 hours after dosing. Plasma samples are obtained by centrifugation and PTH concentrations are determined using a commercially available rat intact PTH ELISA kit (Immutopics, Inc. San Clemente, Calif. Cat. #60-2500). A significant burst of PTH was seen following the treatment with the tested compound. The elevated PTH secretion induced by the tested compound was peak at 2 minutes and returned to baseline level at 30 minutes after dosing (FIG. 1).

Effect of Calcium Receptor Antagonist Compound of Formula I on Body Weight, Body Composition and Bone Density in the Aged Intact and Ovariectomized Female Rat The purpose of this study is to test the effects of test compositions comprising compounds of Formula I in aged intact or ovariectomized (OVX) female rat model. In the following protocol the compound of Formula I can be administered as a pharmaceutically acceptable salt or prodrug thereof.

Study Protocol

Sprague-Dawley female rats are sham-operated or OVX at 18 months of age, while a group of rats is necropsied at day 0 to serve as baseline controls. One day post-surgery, the rats are treated with either vehicle or test compound of Formula I, or a combination of test compound of Formula I and other active agent test compound for 59 days. The vehicle or test compound of Formula I is administered either orally, by oral gavage, or by subcutaneous injection (s.c.), with the test compound being administered at a therapeutically effective dose.

All rats are given s.c. injection of 10 mg/kg of calcein (Sigma, St. Louis, Mo.) for fluorescent bone label 2 and 12 days before necropsy. On the day of necropsy, all rats under ketamine/xylazine anesthesia are weighed and undergoe dual-energy X-ray absorptiometry (DXA, QDR-4500/W, Hologic Inc., Waltham, Mass.) equipped with Rat Whole Body Scan software for lean and fat body mass determination. The rats are necropsied, then autopsied and blood is obtained by cardiac puncture. The distal femoral metaphysis and femoral shafts from each rat are analyzed by peripheral quantitative computerized tomography (pQCT), and volumetric total, trabecular and cortical bone mineral content and density are determined.

Peripheral Quantitative Computerized Tomography (PQCT) Analysis: Excised femurs are scanned by a PQCT X-ray machine (Stratec XCT Research M, Norland Medical Systems, Fort Atkinson, Wis.) with software version 5.40. A 1 millimeter (mm) thick cross section of the femur metaphysis is taken at 5.0 mm (proximal femoral metaphysis, a primary cancellous bone site) and 13 mm (femoral shafts, a cortical bone site) proximal from the distal end with a voxel size of 0.10 mm. Cortical bone is defined and analyzed using contour mode 2 and cortical mode 4. An outer threshold setting of 340 mg/cm$^3$ is used to distinguish the cortical shell from soft tissue and an inner threshold of 529 mg/cm$^3$ to distinguish cortical bone along the endocortical surface. Trabecular bone is determined using peel mode 4 with a threshold of 655 mg/cm$^3$ to distinguish (sub)cortical from cancellous bone. An additional concentric peel of 1% of the defined cancellous bone is used to ensure that (sub)cortical bone was eliminated from the analysis. Volumetric content, density, and area are determined for both trabecular and cortical bone (Jamsa T. et al., Bone 23:155-161, 1998; Ke, H. Z. et al., Journal of Bone and Mineral Research, 16:765-773, 2001).

The experimental groups for the protocol are as follows:
Group I: Baseline controls
Group II: Sham+Vehicle
Group III: OVX+Vehicle
Group IV: OVX+Test Compound of Formula I (in Vehicle)
Group V: OVX+Test Compound of Formula I and Additional Active Agent
Note: Group V only employed when it is desired to test a combination of a compound of Formula I and an additional active agent.

Fracture Healing Assays

Assay for Effects on Fracture Healing After Systemic Administration

Fracture Technique: Sprague-Dawley rats at 3 months of age are anesthetized with Ketamine. A 1 cm incision is made on the anteromedial aspect of the proximal part of the right tibia or femur. The following describes the tibial surgical technique. The incision is carried through to the bone, and a 1 mm hole is drilled 4 mm proximal to the distal aspect of the tibial tuberosity 2 mm medial to the anterior ridge. Intramedullary nailing is performed with a 0.8 mm stainless steel tube (maximum load 36.3 N, maximum stiffness 61.8 N/mm, tested under the same conditions as the bones). No reaming of the medullary canal is performed. A standardized closed fracture is produced 2 mm above the tibiofibular junction by three-point bending using specially designed adjustable forceps with blunt jaws. To minimize soft tissue damage, care is taken not to displace the fracture. The skin is closed with monofilament nylon sutures. The operation is performed under sterile conditions. Radiographs of all fractures are taken immediately after nailing, and rats with fractures outside the specified diaphyseal area or with displaced nails are excluded. The remaining animals are divided randomly into the following groups with 10-12 animals per each subgroup per time point for testing the fracture healing. The first group receives daily gavage of vehicle (water: 100% Ethanol=95:5) at 1 ml/rat, while the others receive daily gavage from 0.01 to 100 mg/kg/day of the compound of Formula I to be tested (1 ml/rat) for 10, 20, 40 and 80 days.

At 10, 20, 40 and 80 days, 10-12 rats from each group are anesthetized with Ketamine and sacrificed by exsanguination. Both tibiofibular bones are removed by dissection and all soft tissue is stripped. Bones from 5-6 rats for each group are stored in 70% ethanol for histological analysis, and bones from another 5-6 rats for each group are stored in a buffered Ringer's solution (+4° C., pH 7.4) for radiographs and biomechanical testing which is performed.

Histological Analysis: The methods for histologic analysis of fractured bone have been previously published by Mosekilde and Bak (The Effects of Growth Hormone on Fracture Healing in Rats: A Histological Description. Bone, 14:19-27, 1993). Briefly, the fracture site is sawed 8 mm to each side of the fracture line, embedded undecalcified in methymethacrylate, and cut frontals sections on a Reichert-Jung Polycut microtome in 8 µm thick. Masson-Trichrome stained mid-frontal sections (including both tibia and fibula) are used for visualization of the cellullar and tissue response to fracture healing with and without treatment. Sirius red stained sections are used to demonstrate the characteristics of the callus structure and to differentiate between woven bone and lamellar bone at the fracture site. The following measurements are performed: (1) fracture gap—measured as the shortest distance between the cortical bone ends in the fracture, (2) callus length and callus diameter, (3) total bone volume area of callus, (4) bony tissue per tissue area inside the callus area, (5) fibrous tissue in the callus, and (6) cartilage area in the callus.

Biomechanical Analysis: The methods for biomechanical analysis have been previously published by Bak and Andreassen (The Effects of Aging on Fracture Healing in Rats. Calcif Tissue mnt 45:292-297, 1989). Briefly, radiographs of all fractures are taken prior to the biomechanical test. The mechanical properties of the healing fractures are analyzed by a destructive three- or four-point bending procedure. Maximum load, stiffness, energy at maximum load, deflection at maximum load, and maximum stress are determined.

A calcium receptor antagonist may be usefully combined with another pharmacologically active compound, or with two or more other pharmacologically active compounds, particularly in the treatment of osteoporosis. For example, a calcium receptor antagonist, particularly a compound of the formula I, or a pharmaceutically acceptable salt or solvate thereof, as defined above, may be administered simultaneously, sequentially or separately in combination with one or more agents selected from: selective estrogen receptor modulators (SERMs), bisphosphonates, parathyroid hormone (PTH) and fragments and analogues thereof, estrogens, calcitonins, synthetic steroids, synthetic isoflavones, vitamin D analogues, vitamin K analogues, strontium salts, cathepsin K inhibitors, $\alpha_v\beta_3$ integrin (vitronectin) antagonists, prostaglandin (PGE2) receptor agonists and receptor activator of nuclear factor κB ligand (RANKL) inhibitors as described hereinabove.

The following non-limiting Preparations and Examples illustrate the preparation of compounds of the present invention.

$^1$H Nuclear magnetic resonance (NMR) spectra were in all cases consistent with the proposed structures. Characteristic chemical shifts (δ) are given in parts-per-million downfield from tetramethylsilane using conventional abbreviations for designation of major peaks: e.g. s, singlet; d, doublet; t, triplet; q, quartet; m, multiplet; br, broad. The mass spectra (m/z) were recorded using either electrospray ionisation (ESI) or atmospheric pressure chemical ionisation (APCI). The following abbreviations have been used for common solvents and various reagents: $CDCl_3$, deuterochloroform; DIEA, diisopropylethylamine; DMF, dimethylformamide; $CD_3OD$, deuteromethanol; $D_6$-DMSO, deuterodimethylsulfoxide; HBTU, O-(Benzotriazol-1-yl)-N,N,N',N'-tetramethyluronium hexafluorophosphate; HCl, hydrochloric acid; HI, hydroiodic acid; HMPA, hexamethylphosphoramide; $KMnO_4$, potassium permanganate; $MgSO_4$, magnesium sulfate; $NaHCO_3$, sodium bicarbonate; $NaHSO_3$, sodium bisulfite; NaOH, sodium hydroxide; $Na_2SO_4$, sodium sulfate; $NH_4Cl$, ammonium chloride; TEA, triethylamine; THF, tetrahydrofuran. 'Ammonia' refers to a concentrated solution of ammonia in water possessing a specific gravity of 0.88. Where thin layer chromatography (TLC) has been used it refers to silica gel TLC using silica gel 60 $F_{254}$ plates, $R^f$ is the distance traveled by a compound divided by the distance traveled by the solvent front on a TLC plate. HPLC refers to high performance liquid chromatography.

The following specific examples are included for illustrative purposes and are not to be construed as a limitation to this disclosure.

Preparation of Intermediates

Preparation of 2,4-Dichloronicotinic acid

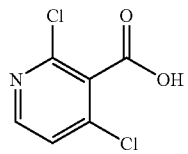

To a stirring solution of diisopropyl ethyl amine (11.1 ml, 81.08 mmol) in THF (50 ml) was added dropwise a solution of BuLi (1.46 M, 43.3 ml, 73.65 mmol) in hexane below −65° C. and the mixture was stirred for 40 minutes. To this solution was added dropwise 2,4-dichloropyridine (10 g, 67.57 mmol) in THF (15 mL) at −78° C. and stirred for 30 minutes. Carbon dioxide generated from freshly crushed dry ice was passed through $CaCl_2$ guard tube and then charged into the reaction mixture for 10 minutes and the reaction mixture was slowly allowed to come to room temperature. The solvent was evaporated under reduced pressure and dissolved in a minimum volume of water. The aqueous layer was washed with water and acidified to pH 4 with conc. HCl. It was then extracted with ethyl acetate, the organic layer was washed with brine and dried over sodium sulfate. The organic solvent was removed under reduced pressure to provide 2,4-dichloronicotinic acid (10.6 g, 82%) as off white solid.

$^1$H NMR (400 MHz, DMSO-$d_6$): δ 14.88-14.54 (br s, 1H), 8.46 (d, J=5.3 Hz, 1H), 7.74 (d, J=5.5 Hz, 1H). FIA MS [M+H]: 191.8

Preparation of Methyl 2,4-dichloronicotinate

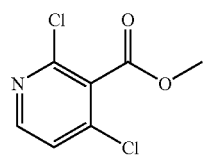

Nitrosomethyl urea (8 g, 78.16 mmol), taken in diethyl ether (30 ml) was cooled to 0° C. and 25% aqueous KOH solution was added slowly under cooling. The ether layer was collected, dried over KOH and added dropwise to a stirring solution of 2,4-Dichloronicotinic acid (3 g, 15.62 mmol) in methanol (5 mL) at 0° C. The reaction mixture was allowed to come to room temperature within 1 hour. The organic solvent was removed under reduced pressure and the crude residue was purified by column chromatography (5-10% EtOAc in hexane) to obtain the pure methyl 2,4-dichloronicotinate (3.00 g, 99%) as colorless oil. $^1$H NMR (400 MHz, $CDCl_3$): δ 8.34 (d, J=5.3 Hz, 1H), 7.33 (d, J=5.4 Hz, 1H), 3.99 (s, 3H).

Preparation of Methyl 4-azido-2-chloronicotinate

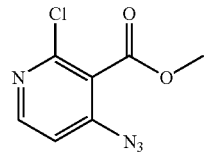

Methyl 2,4-dichloronicotinate (20 g, 96.67 mmol) afforded methyl 4-azido-2-chloronicotinate (15 g, 73%) as cream colored solid following the literature procedure, *J. Prakt.Chem*, 2000; 342, 33-39 (reaction of Methyl 2,4-dichloronicotinate with $NaN_3$ in DMF at 50° C. followed by aqueous workup). $^1$H NMR (400 MHz, DMSO-$d_6$): δ 8.37 (d, J=5.52 Hz, 1H), 7.06 (d, J=5.6 Hz, 1H), 3.96 (s, 3H). FIA MS [M+H]: 213.1 (small peak). IR (KBr): 2126, 1741 $cm^{-1}$ Preparation of Methyl 4-amino-2-chloronicotinate

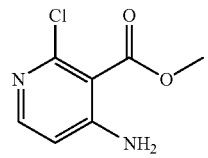

Methyl 4-azido-2-chloronicotinate (15 g, 70.75 mmol) produced methyl 4-amino-2-chloronicotinate (11.2 g, 85%) as light yellow solid following the literature procedure, *Tetrahedron letters,* 2002; 43, 6629-6631 (reduction of the azido group in methyl 4-azido-2-chloronicotinate to the corresponding amine by stirring methyl 4-azido-2-chloronicotinate in aqueous HI at room temperature). $^1$H NMR (400 MHz, DMSO-$d_6$): δ 7.81 (d, J=5.79 Hz, 1H), 6.76 (br s, 2H), 6.62 (d, J=5.81 Hz, 1H), 3.82 (s, 3H). FIA MS [M+H]: 186.9

Preparation of 4-amino-2-chloronicotinic acid

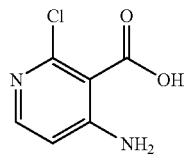

Methyl 4-amino-2-chloronicotinate (21.0 g, 112.9 mmol) and LiOH (10.3 g, 247.5 mmol) was taken in a mixture of dioxane:MeOH:water (3:2:1, ml) and the reaction mixture was heated to 85° C. for 2 hours. The solvent was evaporated under reduced pressure, the residue was dissolved in minimum volume of water and acidified (up to pH 4) with saturated citric acid. The aqueous solution was concentrated until precipitation just started. The mixture was allowed to stand overnight at 10° C. for complete precipitation. The resultant white solid was collected by filtration and recrystallized from isopropyl alcohol-hexane to afford 4-amino-2-chloronicotinic acid (13 g, 66% yield). $^1$H NMR (400 MHz, DMSO-$d_6$): δ 7.59 (d, 1H), 6.47 (d, 1H), 6.37 (brs, 2H).

Preparation of 4-Chloro-2-(trifluoromethyl)nicotinic acid

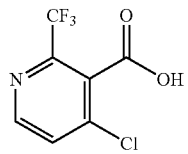

To a stirred solution of 2,2,6,6-tetramethylpiperidine (21.0 mL, 124 mmol) in dry THF (200 mL) in a −78° C. bath is added n-Butyl lithium (66.2 mL of a 2.5M solution in hexanes, 166 mmol). The solution is stirred at −78° C. for 30 minutes, followed by the addition of a solution of 2-(trifluoromethyl)nicotinic acid (7.90 g, 41.4 mmol) in THF (35 mL) via canula. The solution is stirred at −78° C. for 20 minutes, followed by warming to −50° C. for 1 hour (to provide the corresponding lithiated pyridine). In a separate flask, hexachloroethane (29.4 g, 124 mmol) is dissolved in THF (200 mL) and cooled to −15° C. and stirred rapidly. The solution containing the lithiated pyridine is added to the hexachloroethane solution via canula. After complete addition, the mixture is allowed to ward to room temperature. Water (ca 200 mL) is added, followed by removal of the tetrathydrofuran in vacuo. The remaining aqueous residue is extracted with ether-pentane (1:1, 100 mL). The organic layer was discarded. The aqueous layer is acidified with hydrochloric acid (ca. 50 mL of a 1.0 M solution). The aqueous layer is extracted with ethyl acetate. The organic layer is dried over anhydrous magnesium sulfate, filtered and concentrated in vacuo to afford 8.75 g (94%) of the title compound as a tan solid: $^1$H NMR (400 MHz, CD$_3$OD), 8.63 (d, 1H), 7.79 (d, 1H). LC/MS (M+1)=226.1; [see: Schlosser et al., *Eur. J. Org. Chem.* 2003, 1559].

Preparation of Methyl 4-chloro-2-(trifluoromethyl)nicotinate

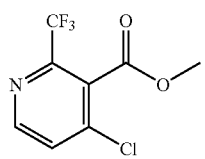

To a stirred solution of 4-chloro-2-(trifluoromethyl)nicotinic acid (8.75 g, 38.8 mmol) in ethyl acetate (100 mL) in an ice bath is added a solution of diazomethane [generated from 12 g (116 mmol) of N-nitroso-N-methylurea] in diethyl ether (200 mL). The solution is stirred for 15 minutes, followed by the addition of acetic acid (until effervescence stops). The solution is concentrated in vacuo to afford 9.75 g (99%) of the title compound as a brown oil: $^1$H NMR (400 MHz, CD$_3$OD), 8.686 (d, 1H), 7.828 (d, 1H), 3.937 (s, 3H). LC/MS (M+1)= 240.1

Preparation of Methyl 4-azido-2-(trifluoromethyl)nicotinate

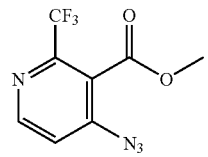

To a stirred solution of methyl 4-chloro-2-(trifluoromethyl)nicotinate (9.75 g, 40.7 mmol) in DMF (300 mL) is added sodium azide (21.2 g, 326 mmol). The solution is warmed to 45° C. for 3 hours and then to 50° C. for 1 hour. The reaction is diluted with water (300 mL) and extracted with ether-pentane (1:1, ca. 1 L). The organic layer is back extracted with water (3×). The organic layer is dried over anhydrous magnesium sulfate, filtered and concentrated in vacuo to afford 9.50 g (95%) of the title compound as a brown oil: $^1$H NMR (400 MHz, CD$_3$OD), 8.651 (d, 1H), 7.603 (d, 1H), 3.878 (s, 3H).

Preparation of Methyl 4-amino-2-(trifluoromethyl)nicotinate and 4-amino-2-(trifluoromethyl)nicotinic acid

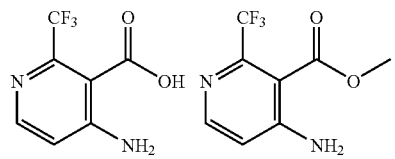

Cold (0° C. ice bath) concentrated hydriodic acid (182 mL of a 57% aqueous solution) is added to methyl 4-azido-2-(trifluoromethyl)nicotinate (7.50 g, 30.5 mmol) in a flask. The mixture is stirred at 0° C. until TLC (ethyl acetate-hexanes, 75:25) shows complete consumption of starting material. The mixture is poured over an ice cold solution of potassium hydroxide (95 g of solid KOH dissolved in 300 mL of water). The mixture is extracted with diethyl ether. The ethereal layer is washed with water, dried over anhydrous magnesium sulfate, filtered and concentrated in vacuo to afford a yellow solid. The solid is dissolved in a minimal amount of dichloromethane and passed through a silica gel plug, eluting with ethyl acetate-hexanes (10:90). The eluant is concentrated to afford 3.42 g (51%) of methyl 4-amino-2-(trifluoromethyl)nicotinate as an off-white solid. $^1$HNMR (400 MHz, CD$_3$OD), 8.11 (d, 1H), 6.93 (d, 1H), 3.878 (s, 3H). LC/MS (M+1)=221.2

The remaining aqueous layer from above is acidified with concentrated hydrochloric acid to pH 2. The aqueous layer is extracted with ethyl acetate (16×). The organic layer is washed with water, dried over anhydrous magnesium sulfate, filtered and concentrated in vacuo to provide an orange solid. The orange solid is triturated in diethyl ether to afford 2.5 g (40%) of 4-amino-2-(trifluoromethyl)nicotinic acid as a yellow solid. $^1$H NMR (400 MHz, CD$_3$OD), 8.09 (d, 1H), 6.93 (d, 1H), LC/MS (M+1)=207.1.

Preparation of 4-Amino-2-(trifluoromethyl)nicotinic acid

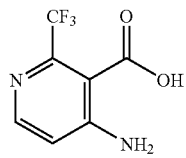

To a stirred solution of methyl 4-amino-2-(trifluoromethyl)nicotinate (1.97 g, 8.97 mmol) in dioxane/methanol/water (3:2:1 ratio by volume) is added lithium hydroxide (0.365 g, 15.2 mmol). The mixture was heated at 85° C. for 8 hours. The reaction mixture was cooled to room temperature and conc. HCl was added dropwise to adjust the pH to 2-3. Saturated NaCl solution was added. The aqueous layer is extracted with ethyl acetate (12x). The organic layer is washed with water, dried over anhydrous magnesium sulfate, filtered and concentrated in vacuo to afford 1.75 g (95%) of 4-amino-2-(trifluoromethyl)nicotinic acid as a yellow solid. $^1$H NMR (400 MHz, CD$_3$OD), 8.09 (d, 1H), 6.93 (d, 1H), LC/MS (M+1)=207.1.

Preparation of ethyl 2-amino-2-cyanoacetate

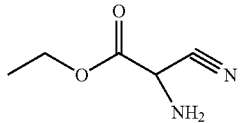

To a stirred solution of the ethyl (hydroxyimino)cyanoacetate (10 g, 70.4 mmol) in water and sodium bicarbonate saturated solution (80 mL) was added sodium dithionite (34.3 g, 197 mmol). The reaction was heated up to 35° C. for 3 h. The solution was then saturated with sodium chloride and extracted with ethyl acetate (3×200 mL). The combined organic phases were dried over sodium sulfate and concentrated, giving an oil of ethyl 2-amino-2-cyanoacetate (1.6 g). $^1$H NMR (400 MHz, CDCl$_3$) δ 4.42 (s, 1H), 4.32 (q, 2H), 1.33 (t, 3H).

Preparation of ethyl 2-cyano-2-formamidoacetate

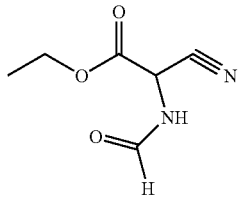

To ethyl 2-amino-2-cyanoacetate (800 mg, 6.24 mmol) in dichloromethane (5 mL) was added cyanomethyl formate (531 mg, 6.24 mmol) in dichloromethane (5 mL) dropwise at 0° C. The reaction was warmed up to room temperature for twelve hours. The reaction was concentrated and purified by silica gel chromatography to give an oil of ethyl 2-cyano-2-formamidoacetate (500 mg). NMR spectrum shows a mixture of starting material and desired product in a 1:1 ratio. The product was dissolved in methylene chloride (10 mL). To this solution was added cyanomethyl formate (797 mg, 9.37 mmol) and the reaction was stirred for twelve more hours. The reaction was concentrated and purified with silica gel chromatography to give an oil of ethyl 2-cyano-2-formamidoacetate (460 mg). $^1$H NMR (400 MHz, CDCl$_3$) δ 8.30 (s, 1H), 6.61 (s, 1H), 5.55 (d, 2H), 4.36 (q, 2H), 1.35 (t, 3H).

Preparation of ethyl 5-aminothiazole-4-carboxylate

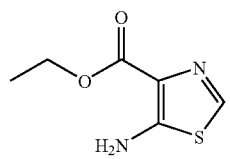

A solution of ethyl 2-cyano-2-formamidoacetate (480 mg, 3.07 mmol) and Lawesson's reagent (746 mg, 1.84 mmol) in toluene (5 mL) was heated up to 80° C. for overnight. The reaction was then diluted with sodium carbonate aqueous solution (20 mL) and methylene chloride (50 mL). Organic phase was washed with brine (20 mL), dried over sodium sulfate and concentrated. Purified with silica gel chromatography to give a solid material of ethyl 5-aminothiazole-4-carboxylate (120 mg). $^1$H NMR (400 MHz, CDCl$_3$) δ 7.86 (s, 1H), 5.98 (s, br, 2H), 4.38 (q, 2H), 1.41 (t, 3H). MS m/z 173.2 (M+H)$^+$.

Preparation of ethyl 5-(2,5-dimethyl-1H-pyrrol-1-yl)thiazole-4-carboxylate

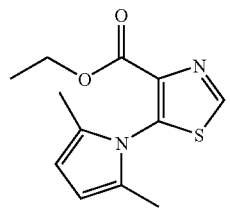

A mixture of ethyl 5-aminothiazole-4-carboxylate (91.3 mg, 0.53 mmol), scandium (III) triflate (2.61 mg, 0.005 mmol) and 2,5-hexanedione (1.5 mL) was heated up to 180° C. for 1 h by microwave. The reaction was then concentrated and purified with silica gel chromatography to give a tan solid of ethyl 5-(2,5-dimethyl-1H-pyrrol-1-yl)thiazole-4-carboxylate (104 mg). $^1$H NMR (400 MHz, CDCl$_3$) δ 8.82 (s, 1H), 5.92 (s, 2H), 4.25 (q, 2H), 2.01 (s, 6H), 1.20 (t, 3H). MS m/z 251.3 (M+H)$^+$.

Preparation of ethyl 5-(2,5-dimethyl-1H-pyrrol-1-yl)thiazole-4-carboxylate

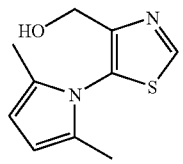

To ethyl 5-(2,5-dimethyl-1H-pyrrol-1-yl)thiazole-4-carboxylate (104 mg, 0.415 mmol) in THF was added 1M DIBAL/THF (1.24 mL, 1.24 mmol) dropwise slowly at −78° C. and stirred for 1 h. The reaction mixture was warmed up to room temperature slowly and stirred for twelve hours. The reaction was then quenched with ice water (5 mL) and diluted with ethyl acetate (100 mL) and 2N NaOH (20 mL). The organic phase was then washed with brine (10 mL), dried over sodium sulfate and concentrated, giving a semi-solid of ethyl 5-(2,5-dimethyl-1H-pyrrol-1-yl)thiazole-4-carboxylate (86 mg). $^1$H NMR (400 MHz, CDCl$_3$) δ 8.81 (s, 1H), 5.90 (s, 2H), 4.43 (s, 2H), 2.00 (s, 6H). MS m/z 209.3 (M+H)$^+$.

Preparation of 5-(2,5-dimethyl-1H-pyrrol-1-yl)thiazole-4-carbaldehyde

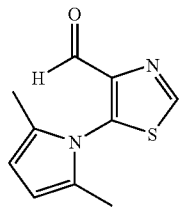

To a solution of (5-(2,5-dimethyl-1H-pyrrol-1-yl)thiazol-4-yl)methanol (86 mg, 0.41 mmol) in methylene chloride was added manganese dioxide (359 mg, 4.13 mmol). The reaction was warmed up to reflux for 3 h. The crude mixture was purified with silica gel chromatography to give an oil of 5-(2,5-dimethyl-1H-pyrrol-1-yl)thiazole-4-carbaldehyde (17 mg). $^1$H NMR (400 MHz, CDCl$_3$) δ 9.72 (s, 1H), 8.87 (s, 1H), 5.98 (s, 2H), 2.05 (s, 6H). MS m/z 207.2 (M+H)$^+$.

2-(5-(2,5-dimethyl-1H-pyrrol-1-yl)thiazol-4-yl)-3-phenethyl-5-(trifluoromethyl)pyrido[4,3-d]pyrimidin-4(3H)-one

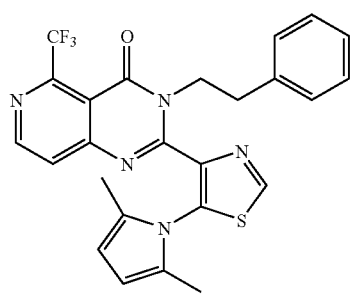

A solution of 4-amino-N-phenethyl-2-(trifluoromethyl)nicotinamide (25.5 mg, 0.082 mmol), 5-(2,5-dimethyl-1H-pyrrol-1-yl)thiazole-4-carbaldehyde (17 mg, 0.082 mmol) and TsOH (1.4 mg, 0.008 mmol) in toluene was heated at reflux overnight. The reaction was then filtered and to the crude mixture was added manganese oxide. The reaction was heated at 110° C. for 4 h. The reaction mixture was filtered, concentrated and purified with silica gel chromatography providing a solid, 2-(5-(2,5-dimethyl-1H-pyrrol-1-yl)thiazol-4-yl)-3-phenethyl-5-(trifluoromethyl)pyrido[4,3-d]pyrimidin-4(3H)-one (7 mg). $^1$H NMR (400 MHz, CDCl$_3$) δ 9.02 (s, 1H), 8.76 (d, 1H), 7.69 (m, 1H), 7.51 (m, 1H), 7.48 (d, 1H), 7.32 (m, 5H), 4.20 (m, 2H), 3.32 (m, 2H), 2.07 (s, 6H). MS m/z 496.5 (M+H)$^+$.

Preparation of methyl 2-(difluoromethyl)benzoate

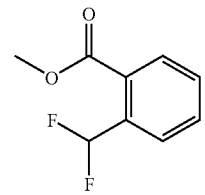

A solution of methyl 2-formylbenzoate (1.0 g, 6.09 mmol) and bis(2-methoxyethyl)amino-sulfur trifluoride (4.04 g, 18.3 mmol) in methylene chloride (10 mL) was heated at reflux for twelve hours. The reaction was concentrated, diluted with ethyl acetate (200 mL) and water (100 mL). Sodium bicarbonate solid was used to neutralize the mixture slowly to pH of 8. The organic phase was then separated and washed with brine (50 mL), dried over sodium sulfate and concentrated. The residue was purified with silica gel chromatography to give methyl 2-(difluoromethyl)benzoate as an oil (700 mg). $^1$H NMR (400 MHz, CDCl$_3$) δ 8.02 (d, 1H), 7.82 (d, 1H), 7.64 (t, 1H), 7.52 (m, 1H). 7.39 (t, 1H), 3.93 (s, 3H).

Preparation of (2-(difluoromethyl)phenyl)methanol

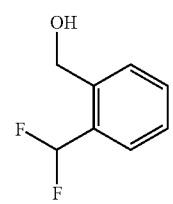

To a solution of methyl 2-(difluoromethyl)benzoate (700 mg, 3.76 mmol) in THF was added 1M lithium aluminum hydride in THF (5.64 mL, 11.3 mmol) dropwise at room temperature for 1 h. The reaction was then poured into ice water (100 mL) and diluted with ethyl acetate (200 mL) and 2N sodium hydroxide aqueous solution (100 mL). The organic phase was then separated and washed with brine (50 mL), dried over sodium sulfate and concentrated, to give (2-(difluoromethyl)phenyl)methanol as an oil (480 mg). ¹H NMR (400 MHz, CDCl₃) δ 7.56 (d, 1H), 7.41 (m, 3H), 6.93 (t, 1H), 4.82 (s, 2H).

Preparation of 2-(difluoromethyl)benzaldehyde

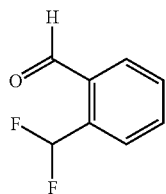

A mixture of (2-(difluoromethyl)phenyl)methanol (100 mg, 0.632 mmol) and manganese oxide (275 mg, 3.16 mmol) in dichloromethane was stirred at room temperature for twelve hours and then at 45° C. for 1 h. The reaction was filtered through celite and concentrated, to give 2-(difluoromethyl)benzaldehyde as an oil (99 mg). ¹H NMR (400 MHz, CDCl₃) δ 10.2 (s, 1H), 7.94 (d, 1H), 7.81 (d, 1H), 7.70 (m, 2H), 6.93 (t, 1H).

Preparation of 2-methylnicotinaldehyde

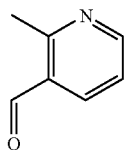

A mixture of (2-methylpyridin-3-yl)methanol (1.0 g, 8.12 mmol) in dichloromethane (10 mL) and manganese oxide (7.06 g, 81.2 mmol) was stirred at room temperature for sixty hours and then heated at 45° C. for 4 h. The reaction was filtered through celite and a plug of silica gel (5×7 cm) using ethyl acetate as eluent. The filtrate was then concentrated to give 2-methyl nicotinaldehyde as an oil (680 mg). ¹H NMR (400 MHz, CDCl₃) δ 10.32 (s, 1H), 8.67 (dd, 1H), 8.09 (dd, 1H), 7.31 (dd, 1H), 2.88 (s, 3H).

Preparation of 3-(difluoromethyl)-2-methylpyridine

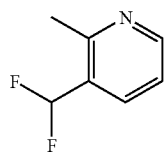

A solution of 2-methylnicotinaldehyde (680 mg, 5.61 mmol) and bis(2-methoxyethyl)amino-sulfur trifluoride (3.72 g, 16.8 mmol) in dichloroethane (10 mL) was warmed at reflux overnight. The reaction was concentrated, diluted with ethyl acetate (200 mL) and water (100 mL). Sodium bicarbonate solid was used to neutralize the mixture slowly to pH of 8. The organic phase was then separated and washed with brine (50 mL), dried over sodium sulfate and concentrated. The residue was purified with flash chromatography (25+S Biotage, heptane/ethyl acetate=100:0 to 80:20), to give 3-(difluoromethyl)-2-methylpyridine as an oil (110 mg). ¹H NMR (400 MHz, CDCl₃) δ 7.58 (d, 1H), 7.81 (d, 1H), 7.22 (m, 1H), 6.77 (t, 1H), 2.64 (s, 3H).

Preparation of 3-(difluoromethyl)picolinaldehyde

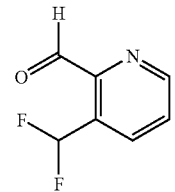

A mixture of 3-(difluoromethyl)-2-methylpyridine (110 mg, 0.768 mmol) and selenium oxide (102 mg, 0.922 mmol) in 1,4-dioxane (3 mL) was warmed at reflux for twelve hours. The reaction mixture was then concentrated and purified with flash chromatography (12+S Biotage, heptane/ethyl acetate=1:0 to 1:1), to give 3-(difluoromethyl)picolinaldehyde as an oil (11 mg). ¹H NMR (400 MHz, CDCl₃) δ 10.1 (s, 1H), 8.90 (d, 1H), 8.22 (d, 1H), 7.64 (m, 1H), 7.59 (t, 1H).

Preparation of 1,2-difluoro-4-(2-nitroprop-1-enyl)benzene

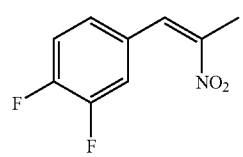

3,4-difluorobenzaldehyde (54 g, 380 mmol), ammonium acetate (19 g, 247 mmol), and 4 Å molecular sieves (54 g) were combined in nitroethane (810 mL) and heated at reflux for 24 hours. The reaction was filtered, and concentrated in vacuo. The resultant mixture was partitioned between ethyl acetate (500 mL) and water (300 mL). The organic phase was separated, washed with brine, dried over sodium sulfate, filtered and concentrated in vacuo. The residue was cooled to 4° C. for 2 hours then ethanol (100 mL) was added to give yellow crystals which were collected by filtration. (57.2 g 75.6% yield). ¹H NMR (400 MHz, CDCl₃) δ 8.0 (s, 1H), 7.15-7.25 (m, 2H), 3.7 (t, 1H), 2.4 (s, 3H).

Preparation of 1-(3,4-difluorophenyl)propan-2-amine hydrochloride

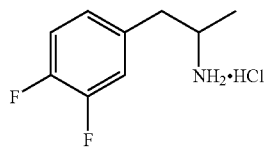

(E,Z)-1,2-difluoro-4-(2-nitroprop-1-enyl)benzene (2.52 g, 12.65 mmol) was dissolved in anhydrous THF (30 mL) and cooled in an ice bath. To this was added a 1.0M THF solution of lithium aluminum hydride (38 mL, 38 mmol). The reaction was stirred at room temperature for 15 minutes then heated at reflux for 2 hours. The reaction mixture was cooled to room temperature, and worked up by the successive addition of water (1.5 mL), 15% NaOH (1.5 mL), and water (4.5 mL). The reaction mixture was stirred to granulate a white precipitate which was filtered. The filtrate was diluted with water (50 mL), extracted with ethyl acetate (2×100 mL). The organic phase was dried over sodium sulfate, filtered, and concentrated in vacuo. The residue was redissolved in ethyl acetate (25 mL), to which was added 4N HCl/dioxane solution (7 mL), and the resulting mixture was stirred at room temperature for 10 minutes. This mixture was concentrated in vacuo and triturated with hexanes to afford the product as a colorless solid (2.32 g, 88% yield). $^1$H NMR (400 MHz, CD$_3$OD) δ 7.2 (m, 2H), 7.05 (m, 1H), 3.5 (m, 1H), 2.8-3.0 (dd, 2H), 1.25 (d, 3H). MS m/z 172.2 (M+H)$^+$.

Preparation of 4-amino-N-(1-(3,4-difluorophenyl)propan-2-yl)-2-(trifluoromethyl)nicotinamide

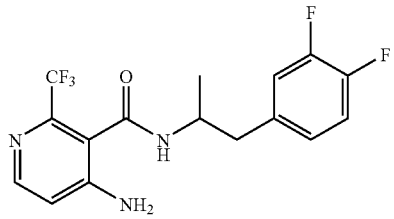

4-amino-2-(trifluoromethyl)nicotinic acid (4.4 g, 18.14 mmol) was suspended in a mixture of anhydrous DMF (100 mL) and anhydrous dichloromethane (200 mL). To this was added triethylamine (6 g, 60 mmol), followed by 1-(3,4-difluorophenyl)propan-2-amine (3.75 g, 21.90 mmol). HBTU (9.63 g, 25.4 mmol) was added and the mixture was allowed to stir at room temperature overnight. The reaction mixture was concentrated in vacuo to remove dichloromethane. The resultant DMF solution was poured into water and extracted twice with ethyl acetate. The organic layer was washed successively with 1N NaOH and water, then dried over magnesium sulfate, filtered and concentrated in vacuo to give an oil. This oil was purified by silica gel column chromatography using 20-40% acetone/hexanes as eluant to provide the product as a colorless solid (6.57 g, 55% yield). $^1$H NMR (400 MHz, CDCl$_3$) δ 8.2 (d, 1H), 7.1 (m, 2H), 6.95 (m, 1H), 6.7 (d, 1H), 4.07 (m, 1H), 4.9 (bd, 2H), 4.4 (m, 1H), 2.7-2.9 (dd, 2H), 1.2 (d, 2H). MS m/z 360.2 (M+H)$^+$.

Preparation of (3-(benzyloxy)pyridin-2-yl)methanol

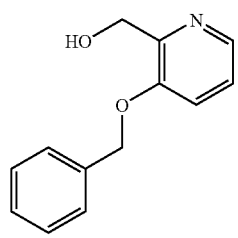

2-hydroxymethyl-3-hydroxypyridine (100.3 g, 620.7 mmol) was dissolved in acetone (1 L). Potassium carbonate (180 g, 1.3 mol) was added followed by benzyl bromide (127 g, 745 mmol). The mixture was heated at reflux for 48 hours. The resultant mixture was cooled to room temperature and filtered through celite. The filter cake was washed with acetone (1 L). The combined filtrate was concentrated in vacuo to provide an orange oil. This oil was purified by silica gel column chromatography using 10-40% ethyl acetate/hexanes as eluant. The resultant tan solid was recrystallized from hexanes to provide the product (88.2 g, 66% yield). $^1$H NMR (400 MHz, CDCl$_3$) δ 8.2 (t, 1H), 7.4 (m, 5H), 7.15 (d, 2H), 5.1 (s, 2H), 4.8 (d, 2H), 4.3 (t, 1H).

Preparation of 3-(benzyloxy)picolinaldehyde

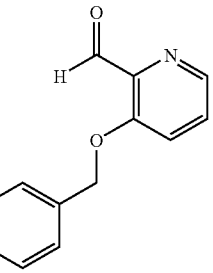

(3-(benzyloxy)pyridin-2-yl)methanol (87 g, 400 mmol) was dissolved in anhydrous dioxane (80 mL). Manganese dioxide (351 g) was added and the mixture was heated for 2 hours at 80° C.

The reaction mixture was filtered through celite and the filter cake was washed with ethyl acetate (300 mL). The filtrate was concentrated in vacuo to yield a brown oil which solidified upon standing. (84.12 g, 98% yield). $^1$H NMR (400 MHz, CDCl$_3$) δ 8.4 (d, 1H), 7.25-7.45 (m, 8H), 5.25 (s, 2H).

Preparation of 2-(3-(benzyloxy)pyridin-2-yl)-3-(1-(3,4-difluorophenyl)propan-2-yl)-5-(trifluoromethyl)-2,3-dihydropyrido[4,3-d]pyrimidin-4(1H)-one

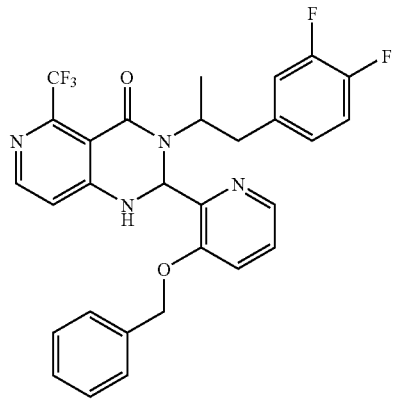

4-amino-N-(1-(3,4-difluorophenyl)propan-2-yl)-2-(trifluoromethyl)nicotinamide (3.61 g, 10.05 mmol) and 3-(benzyloxy)picolinaldehyde (2.57 g, 12.1 mmol) were combined along with a catalytic amount of 4-toluenesulfonic acid (0.03 g, 0.20 mmol) in anhydrous toluene (150 mL). This was heated at reflux overnight in a round bottom flask fitted with a Dean-Stark trap. The resultant dark solution was cooled to room temperature, concentrated in vacuo to a dark brown oil. This oil was purified by silica gel column chromatography using 30% acetone/hexanes as eluant to provide the product diastereomers as an oil (4.61 g, 82% yield). $^1$H NMR (400 MHz, CDCl$_3$) δ 8.2 (m, 1H), 8.0 (m, 1H), 7.3-7.6 (m, 7H), 5.15 (d, 2H), 3.0 (dd, 1H), 2.8 (m, 1H), 1.25 (d, 3H). MS m/z 555.2 (M+H)$^+$.

Preparation of 3-(1-(3,4-difluorophenyl)propan-2-yl)-2-(3-hydroxypyridin-2-yl)-5-(trifluoromethyl)-2,3-dihydropyrido[4,3-d]pyrimidin-4(1H)-one

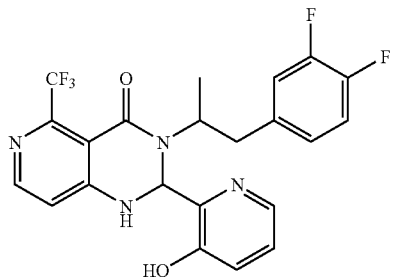

2-(3-(benzyloxy)pyridin-2-yl)-3-(1-(3,4-difluorophenyl)propan-2-yl)-5-(trifluoromethyl)-2,3-dihydropyrido[4,3-d]pyrimidin-4(1H)-one (4.61 g, 8.31 mmol) was dissolved in absolute ethanol (150 mL). To this was added 10% palladium on carbon (0.50 g) and the mixture was hydrogenated on a Parr shaker at 45 PSI for 2.5 hours. The reaction was filtered through celite, and the filter cake washed with ethanol. The combined filtrates were concentrated in vacuo to an oil. This oil was purified by silica gel column chromatography using 20%-40% acetone/hexanes as eluant to yield the product diastereomers as a pale yellow foam (3.86 g, 77% yield).

$^1$H NMR (400 MHz, CD$_3$OD) δ 8.0 (t, 1H), 7.8 (t, 1H), 7-7.2 (m, 5H), 4.8 (m, 1H), 4.5 (m, 1H), 2.8-3.1 (dd, 2H), 1.3 (d, 3H), 1.0 (d, 3H). MS m/z 465.3 (M+H)$^+$.

Preparation of 3-(1-(3,4-difluorophenyl)propan-2-yl)-2-(3-hydroxypyridin-2-yl)-5-(trifluoromethyl)pyrido[4,3-d]pyrimidin-4(3H)-one

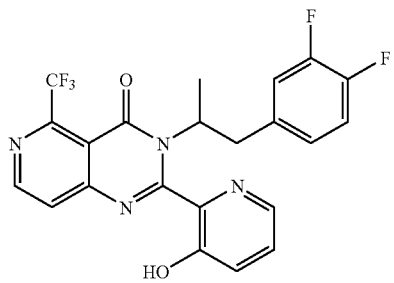

3-(1-(3,4-difluorophenyl)propan-2-yl)-2-(3-hydroxypyridin-2-yl)-5-(trifluoromethyl)-2,3-dihydropyrido[4,3-d]pyrimidin-4(1H)-one (27.3 g, 58.8 mmol) was dissolved in 4-methyl-2-pentanone (500 mL). To this was added manganese dioxide (76.7 g, 882 mmol) and the mixture was heated to 90° C. for 1 hour. The reaction mixture was cooled and filtered through celite. The filter cake was washed with ethyl acetate. Combined filtrates were concentrated in vacuo to a pale yellow solid (8.35 g). The solid was slurried in hexanes and the resultant colorless solid was collected. The filtrate was concentrated and purified by silica gel column chromatography using 20-30% acetone/hexanes as eluant to yield additional product (3.47 g, 43.5% total yield).

Preparation of (R)-4-amino-N-(1-phenylpropan-2-yl)-2-(trifluoromethyl)nicotinamide

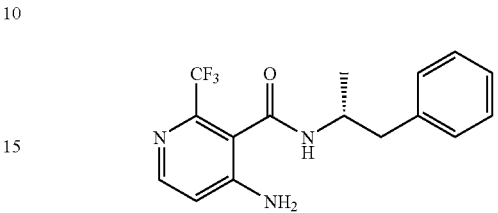

4-amino-2-(trifluoromethyl)nicotinic acid (15 g, 61.83 mmol) was suspended in a mixture of anhydrous DMF (300 mL) and anhydrous dichloromethane (500 mL). To this was added triethylamine (30.4 mL, 216 mmol), followed by L-amphetamine hydrochloride (12.7 g, 74.2 mmol). HBTU (30.5 g, 80.4 mmol) was added and the mixture was allowed to stir at room temperature overnight. The reaction mixture was concentrated in vacuo to remove dichloromethane. The resultant DMF solution was poured into water, extracted with ethyl acetate (1 L). The organic layer was washed successively with 1N NaOH, saturated sodium bicarbonate, water, dried over sodium sulfate, filtered and concentrated in vacuo to give an oil. This oil was purified by silica gel column chromatography using 40-70% ethyl acetate/heptanes as eluant to provide the product as a colorless foam (18.3 g, 92% yield). $^1$H NMR (400 MHz, CDCl$_3$) δ 8.2 (d, 1H), 7.2-7.4 (m, 5H), 6.6 (d, 1H), 5.8 (d, 1H), 4.7 (bs, 2H), 4.5 (m, 1H), 2.9 (m, 2H), 1.25 (d, 3H). MS m/z 324.3 (M+H)$^+$.

Preparation of 2-(2-methoxyphenyl)-3-((R)-1-phenylpropan-2-yl)-5-(trifluoromethyl)-2,3-dihydropyrido[4,3-d]pyrimidin-4(1H)-one

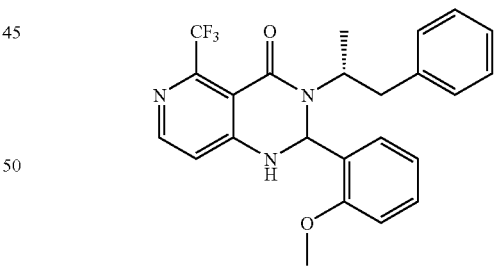

(R)-4-amino-N-(1-phenylpropan-2-yl)-2-(trifluoromethyl)nicotinamide (16.23 g, 50.2 mmol) and ortho-anisaldehyde (8.2 g, 60.2 mmol) were combined along with a catalytic amount of 4-toluenesulfonic acid (0.174 g, 1.0 mmol) in anhydrous toluene (550 mL). This mixture was heated at reflux overnight in a round bottom flask fitted with a Dean-Stark trap. The resultant dark solution was cooled to room temperature, then concentrated in vacuo to a dark brown paste. This paste was suspended in ethyl acetate, and the resultant solids were collected by filtration to provide the product (6.94 g). The filtrate was concentrated in vacuo then purified by silica gel column chromatography using 40-60% ethyl acetate/hexanes as eluant to give 12.1 g of additional product diastereomers (84% total yield). $^1$H NMR (400 MHz, CDCl$_3$) δ 8.19 (d, 1H), 7.1-7.3 (m, 7H), 6.9 (d, 1H), 6.8 (t, 1H), 6.5 (d, 1H), 5.95 (d, 1H), 5.7 (d, 1H), 4.8 (m, 1H), 3.95 (s, 3H), 3.0 (dd, 1H), 2.4 (dd, 1H), 1.3 (d, 3H). MS m/z 442.4 (M+H)$^+$.

Preparation of (R)-2-(2-methoxyphenyl)-3-(1-phenylpropan-2-yl)-5-(trifluoromethyl)pyrido[4,3-d]pyrimidin-4(3H)-one

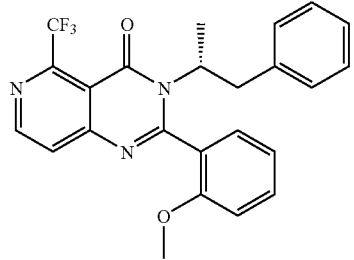

2-(2-methoxyphenyl)-3-((R)-1-phenylpropan-2-yl)-5-(trifluoromethyl)-2,3-dihydropyrido[4,3-d]pyrimidin-4(1H)-one (19.04 g, 43.13 mmol) was dissolved in acetone (800 mL). To this was added a 5% aqueous solution of potassium permanganate (34.1 g KMnO$_4$ in 700 mL water). The resultant mixture was stirred at room temperature overnight. The reaction was quenched by pouring it into a 10% aqueous solution of sodium bisulfite (3 L). The resulting aqueous solution was extracted with ethyl acetate (3×700 mL). The organic phase was washed with brine, dried over magnesium sulfate, filtered and concentrated in vacuo to provide an oil. This oil was purified by flash chromatography using 25-50% ethyl acetate/heptanes as eluant to provide the product as a solid. This solid was recrystallized from ethyl acetate/hexanes to yield a colorless solid (12.5 g). $^1$H NMR (400 MHz, CDCl$_3$) δ 8.8 (d, 1H), 7.65 (d, 1H), 7.4 (t, 1H), 7.15 (m, 7H), 6.95 (t, 1H), 6.8 (d, 1H), 6.35 (d, 1H), 4.2 (m, 1H), 3.8 (s, 3H), 3.6 (dd, 1H), 2.9 (dd, 1H), 1.75 (d, 3H). MS m/z 440.3 (M+H)$^+$.

EXAMPLE 1

Preparation of 2-(2-Hydroxy-phenyl)-3-phenethyl-5-trifluoromethyl-3H-pyrido[4,3-d]pyri-midin-4-one)

Preparation 1a: 4-Amino-2-chloro-N-phenethyl-nicotinamide

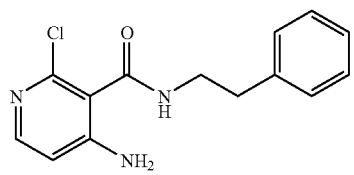

4-Amino-2-chloro-nicotinic acid (1 g, 5.795 mmol) was dissolved in DMF (30 mL) and dichloromethane (50 mL). Phenethylamine (0.87 mL, 6.954 mmol, 1.2 equiv.) was added followed by TEA (1.21 mL, 8.693 mmol, 1.5 equiv.) and HBTU (2.64 g, 6.954 mmol, 1.2 equiv.) and the reaction stirred at 20° C. for 12 hours. The reaction mixture was then diluted with dichloromethane and the aqueous layer was extracted with 20% isopropyl alcohol/dichloromethane. The combined organic portions were washed with 0.5N NaOH solution, NH$_4$Cl solution, water, brine, dried over anhydrous MgSO$_4$, filtered and concentrated. The crude material was purified by column chromatography using 2:1 ethyl acetate: hexane to provide 1.23 g (77%) of product.

Preparation 1b: 5-Chloro-2-(2-methoxy-phenyl)-3-phenethyl-2,3-dihydro-1H-pyrido[4,3-d]pyrimidin-4-one

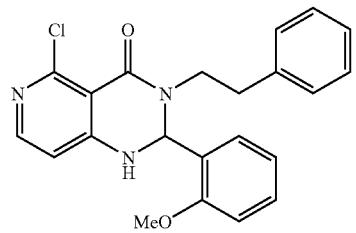

To a solution of 4-amino-2-chloro-N-phenethyl-nicotinamide (808 mg, 2.93 mmol) in 8 mL of acetonitrile at 20° C. was added 0-anisaldehyde (399 mg, 2.93 mmol) and a catalytic amount of p-toluenesulfonic acid (10 mg, 0.059 mmol). The resulting solution was then heated to reflux under Dean-Stark trap for 12 hours. The reaction mixture was cooled to 20° C. and diluted with ethyl acetate. The mixture was then partitioned between ethyl acetate and aqueous sodium bicarbonate. The organic phase was washed 3× with NaHCO$_3$, 1× with water, 1× with brine and then dried over anhydrous Na$_2$SO$_4$, filtered and evaporated to dryness. 1.08 g of pale yellow sticky solid was obtained. The resulting crude material was used without further purification.

Preparation 1c: 5-Chloro-2-(2-methoxy-phenyl)-3-phenethyl-3H-pyrido[4,3-d]pyrimidin-4-one

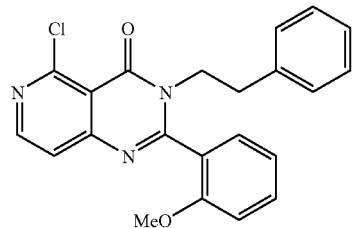

5-Chloro-2-(2-methoxy-phenyl)-3-phenethyl-2,3-dihydro-1H-pyrido[4,3-d]pyrimidin-4-one (1.0 g, 2.54 mmol) was placed in a flask, acetone (10 mL) was added and the mixture stirred vigorously at 20° C. A 5% aqueous solution of potassium permanganate (KMnO$_4$) was added (50.8 mmol, 2 equiv.). The reaction progress was monitored by HPLC. The reaction was stirred for 12 hours. Another 2 equiv. of KMnO$_4$ was added and reaction stirred at ambient temperature for 4 hours until reaction was complete according to HPLC. The reaction was then quenched with 10% aqueous NaHSO$_3$, filtered by gravity filtration and partitioned between ethyl acetate and water. The aqueous layer was extracted 3× with ethyl acetate, the combined organic layers washed 1× with water, 1× brine and then dried over anhydrous Na₂SO₄. Filtration and evaporation of the solvent gave 398 mg of tan solid. The original filter cake was suspended in dichloromethane and sonicated for 5 minutes, then repeated two more times. The suspensions were filtered through a nylon filter, combined and evaporated to dryness to give additional 282 mg of product for combined total crude yield of 680 mg (68%) of a tan solid. The product was used further without purification.

Preparation 1d: 5-Iodo-2-(2-methoxy-phenyl)-3-phenethyl-3H-pyrido[4,3-d]pyrimidin-4-one

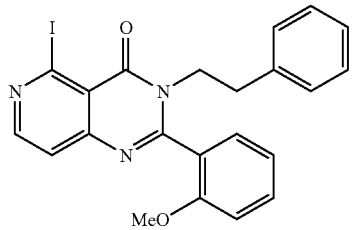

A mixture of 5-chloro-2-(2-methoxy-phenyl)-3-phenethyl-3H-pyrido[4,3-d]pyrimidin-4-one (300 mg, 0.766 mmol), trimethylsilyl chloride (0.097 mL, 0.766 mmol) and sodium iodide (344 mg, 2.297 mmol, 3 equiv.) in propionitrile (7.66 mL) was heated to reflux under nitrogen in the dark for 4 hours. TLC showed no starting material remaining. The reaction mixture was cooled to ambient temperature and poured into 1N NaOH (30 mL). The resulting suspension was extracted with ethyl acetate (3×20 mL), the combined extracts were washed with water, brine and dried, filtered and concentrated in vacuo to give a brown oil. The crude product was purified by column chromatography using 10% ethyl acetate in dichloromethane to provide 235 mg (64%) of product.

Preparation 1e: 2-(2-Methoxy-phenyl)-3-phenethyl-5-trifluoromethyl-3H-pyrido[4,3-d]pyrimidin-4-one

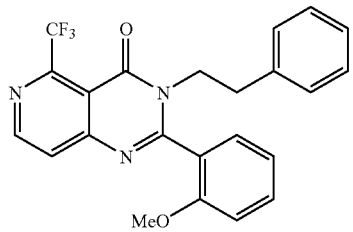

In a flame dried 2-dram vial, a mixture of 5-iodo-2-(2-methoxy-phenyl)-3-phenethyl-3H-pyrido[4,3-d]pyrimidin-4-one (67 mg, 0.138 mmol), methyl 2,2-difluoro-2-(fluorosulfonyl)acetate (0.035 mL, 0.277 mmol, 2 equiv.), copper iodide (32 mg, 0.167 mmol, 1.2 equiv), HMPA (0.048 mL, 0.277 mmol, 2 equiv) in DMF (2 mL) was stirred under nitrogen at 80° C. for 12 hrs. The reaction mixture was then cooled to ambient temperature, diluted with dichloromethane and washed 3× with water. The organic phase was then dried over anhydrous MgSO₄, filtered and concentrated. The crude material was purified on preparative TLC in 50:50 ethyl acetate:hexane to provide 16.8 mg of product (29%). 2-(2-Hydroxy-phenyl)-3-phenethyl-5-trifluoromethyl-3H-pyrido[4,3-d]pyri-midin-4-one)

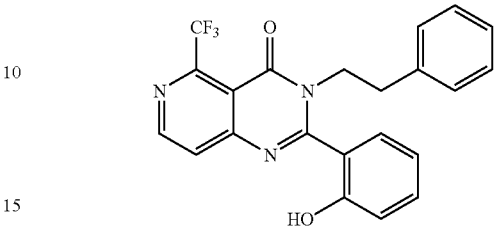

2-(2-Methoxy-phenyl)-3-phenethyl-5-trifluoromethyl-3H-pyrido[4,3-d]pyrimidin-4-one (8.4 mg, 0.0197 mmol) was dissolved in dichloromethane (0.5 mL), the mixture cooled to 0° C. and a solution of boron trichloride was added (1M in hexane, 0.16 mL, 8 equiv.). The reaction mixture was then heated at 40° C. overnight. The reaction mixture was then cooled to ambient temperature, diluted with methanol (2 mL) and then heated to 70° C. for 1 hour. The solvent was evaporated and the residue partitioned between methylene chloride and saturated NaHCO₃ solution. The aqueous layer was extracted 3× with dichloromethane. The pooled organic extracts were washed with water, brine, dried, filtered and concentrated. The crude product was purified using preparative TLC in 50:50 ethyl acetate:hexane to provide 5 mg (62%) of final product.

¹H NMR (400 MHz, CDCl₃) δ 8.82 (d, 1H), 7.67 (d, 1H), 7.41 (t, 1H), 7.27 (m, 1H), 7.15 (m, 3H), 7.05 (m, 2H), 6.86 (m, 2H), 4.38 (t, 2H), 2.94 (t, 2H). MS m/z 412.3 (M+H)⁺.

Alternatively, 2-(2-Hydroxy-phenyl)-3-phenethyl-5-trifluoromethyl-3H-pyrido[4,3-d]pyri-midin-4-one) can be prepared using 4-amino-2-(trifluoromethyl)nicotinic acid as the starting material.

Preparation 1f: 4-Amino-N-phenethyl-2-(trifluoromethyl)nicotinamide

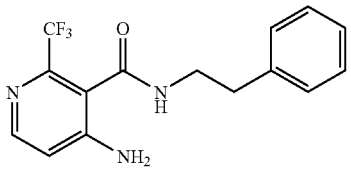

4-Amino-2-(trifluoromethyl)nicotinic acid (150 mg, 0.78 mmol) was dissolved in DMF (4 mL) and dichloromethane (6 mL). Phenethylamine (106 mg, 0.87 mmol, 1.2 equiv.) was added followed by TEA (0.15 mL, 1.1 mmol, 1.5 equiv.) and HBTU (331 mg, 0.87 mmol, 1.2 equiv.) and the reaction stirred at 20° C. for 12 hours. The reaction mixture was then diluted with dichloromethane and the aqueous layer was extracted with dichloromethane. The combined organic portions were washed with 0.5N NaOH solution, NH₄Cl solution, water, brine, dried over anhydrous MgSO₄, filtered and concentrated. The crude material was purified by column chromatography using 2:1 ethyl acetate:hexane to provide 79 mg (36%) of product. The product can be converted to 2-(2-Hydroxy-phenyl)-3-phenethyl-5-trifluoromethyl-3H-pyrido[4,3-d]pyri-midin-4-one) by using the title compound above, Preparation 1f, and following the procedures described in Preparation 1b (condensation with an appropriate aldehyde R2'CHO), Preparation 1c (oxidation with KMnO4) and the deprotection step using BCl3 (when converting a methoxy moiety in R2 to the hydroxy in R2) as described above.

The following title compounds may be prepared in a manner analogous to Example 1 using Preparation 1a, 4-Amino-2-chloro-N-phenethyl-nicotinamide or 4-amino-2-chloro-6-methylnicotinic acid or Preparation 1f, 4-Amino-N-phenethyl-2-(trifluoromethyl)nicotinamide, or other appropriate nicotinamide derivative with the corresponding aldehyde of formula R2'CHO (it is to be understood that a methoxy group or benzyloxy group in the R2' moiety can be deprotected to the corresponding hydroxy group to provide the R2 moiety in the compound of formula I).

EXAMPLE 2

2-(3-Fluoro-2-hydroxy-phenyl)-3-phenethyl-5-trifluoromethyl-3H-pyrido[4,3-d]pyrimidin-4-one

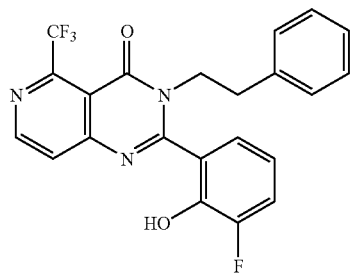

$^1$H NMR (400 MHz, CDCl$_3$) δ 8.90 (d, 1H), 7.75 (d, 1H), 7.25 (t, 3H), 7.05 (m, 3H), 6.90 (m, 2H), 4.39 (m, 2H), 2.94 (m, 2H). MS m/z 430.3 (M+H)$^+$.

EXAMPLE 3

2-(3-Hydroxy-pyridin-2-yl)-3-phenethyl-5-trifluoromethyl-3H-pyrido[4,3-d]pyrimidin-4-one

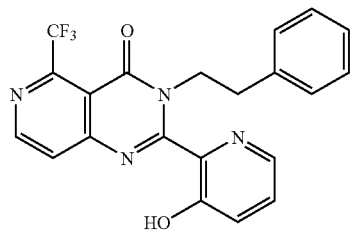

$^1$H NMR (400 MHz, CDCl$_3$) δ 8.95 (d, 1H), 8.30 (d, 1H), 7.75 (d, 1H), 7.45 (m, 3H), 7.25 (m, 5H), 4.99 (m, 2H), 3.33 (m, 2H). MS m/z 413.2 (M+H)$^+$.

EXAMPLE 4a (R)-2-(2-Hydroxy-phenyl)-3-(1-methyl-2-phenylethyl)-5-trifluoromethyl-3H-pyrido[4,3-d]pyrimidin-4-one

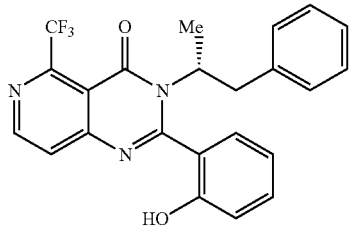

(R)-2-(2-methoxyphenyl)-3-(1-phenylpropan-2-yl)-5-(trifluoromethyl)pyrido[4,3-d]pyrimidin-4(3H)-one (6.6 g, 15.02 mmol) was dissolved in anhydrous dichloromethane (75 mL) and cooled to 0° C. in an ice bath. To this was added a 1M dichloromethane solution of boron trichloride (31.5 mL, 31.5 mmol) slowly to maintain temperature. After addition, the reaction mixture was stirred for 2-5 minutes. The reaction mixture was transferred via canulla to a 0° C. aqueous solution of diethanolamine (10.3 g, 97.6 mmol in 150 mL water) with stirring. The reaction mixture was allowed to come to room temperature and stir for 1 hour. The reaction mixture was diluted with dichloromethane, and the layers separated. The organic layer was washed with brine, dried over magnesium sulfate, filtered, and concentrated in vacuo to provide a foam. This foam was purified by silica gel column chromatography using 20-40% ethyl acetate/hexanes as eluant to give a colorless foam which was then crystallized from ethyl acetate/hexanes to provide the product (4.2 g). $^1$H NMR (400 MHz, CDCl$_3$) δ 8.79 (d, 1H), 7.6 (d, 1H), 7.45 (m, 1H), 7.00 (m, 6H), 6.90 (m, 2H), 3.60 (m, 2H), 3.10 (m, 2H), 1.99 (t, 3H). MS m/z 426.3 (M+H)$^+$.

EXAMPLE 4b (S)-2-(2-Hydroxy-phenyl)-3-(1-methyl-2-phenylethyl)-5-trifluoromethyl-3H-pyrido[4,3-d]pyrimidin-4-one

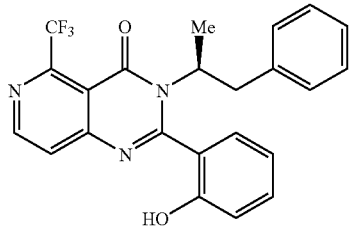

Prepared analogous to Example 4a starting from (S)-2-(2-methoxyphenyl)-3-(1-phenylpropan-2-yl)-5-(trifluoromethyl)pyrido[4,3-d]pyrimidin-4(3H)-one. $^1$H NMR (400

MHz, CDCl₃) δ 8.79 (d, 1H), 7.6 (d, 1H), 7.45 (m, 1H), 7.00 (m, 6H), 6.90 (m, 2H), 3.60 (m, 2H), 3.10 (m, 2H), 1.99 (t, 3H). MS m/z 426.3 (M+H)⁺.

EXAMPLE 5

(R)-2-(3-Hydroxy-pyridin-2-yl)-3-(1-methyl-2-phenyl-ethyl)-5-trifluoromethyl-3H-pyrido[4,3-d]pyrimidin-4-one

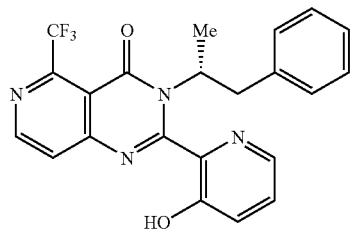

¹H NMR (400 MHz, CDCl₃) δ 8.78 (d, 1H), 8.31 (dd, 1H), 7.49 (d, 1H), 7.41 (m, 2H), 7.02 (m, 2H), 6.88 (m, 3H), 5.31 (m, 1H), 3.62 (dd, 1H), 3.18 (dd, 1H), 1.89 (d, 3H). MS m/z 427.4 (M+1).

EXAMPLE 6

(R, S)-2-(3-Hydroxy-pyridin-2-yl)-3-(1-methyl-2-(2-fluorophenyl)ethyl)-5-trifluoromethyl-3H-pyrido[4,3-d]pyrimidin-4-one

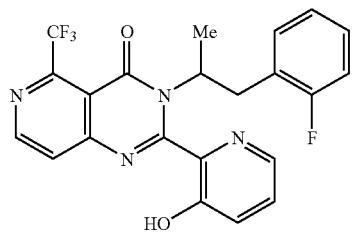

¹H NMR (400 MHz, CD₃OD), 8.784 (d, 1H), 8.10 (dd, 1H), 7.701 (d, 1H), 7.40 (m, 2H), 7.14 (m, 1H), 6.97 (t, 1H), 6.890 (m 2H), 4.23 (m, 1H), 3.42 (dd, 2H), 3.29 (dd, 2H), 1.59 (d, 3H) MS m/z (M+1) 445.4

The racemic compound of Example 6 can be separated into its single enantiomer components (Examples 6a and 6b) by preparative chromatography on a Chiralpak™ AS (10 cm×50 cm) column (Daicel (U.S.A.) Chemical Industries, Ltd, Fort Lee, N.J. 07024 U.S.A.) using Heptane/EtOH (90/10) as mobile phase at a flow rate of 475 mL/min.

EXAMPLE 6a

Enantiomer 1: 2-(3-Hydroxy-pyridin-2-yl)-3-(1-methyl-2-(2-fluorophenyl)ethyl)-5-trifluoromethyl-3H-pyrido[4,3-d]pyrimidin-4-one

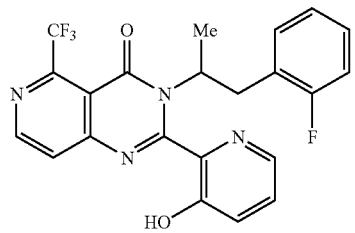

¹H NMR (400 MHz, CD₃OD), 8.78 (d, 1H), 8.10 (dd, 1H), 7.70 (d, 1H), 7.40 (m, 2H), 7.12 (m, 1H), 6.96 (dt, 1H), 6.87 (m, 2H), 4.28 (m, 1H), 3.34 (m, 1H), 3.30 (m, 1H), 1.59 (d, 2H) LC/MS (M+1)=445.3

EXAMPLE 6b

Enantiomer 2: 2-(3-Hydroxy-pyridin-2-yl)-3-(1-methyl-2-(2-fluorophenyl)ethyl)-5-trifluoromethyl-3H-pyrido[4,3-d]pyrimidin-4-one

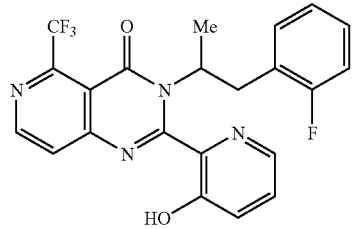

¹H NMR (400 MHz, CD₃OD), 8.78 (d, 1H), 8.10 (dd, 1H), 7.70 (d, 1H), 7.40 (m, 2H), 7.12 (m, 1H), 6.96 (dt, 1H), 6.87 (m, 2H), 4.28 (m, 1H), 3.34 (m, 1H), 3.30 (m, 1H), 1.59 (d, 2H) LC/MS (M+1)=445.3.

EXAMPLE 7

2-(2-Hydroxyphenyl)-3-(2-fluorophenyl)ethyl)-5-trifluoromethyl-3H-pyrido[4,3-d]pyrimidin-4-one

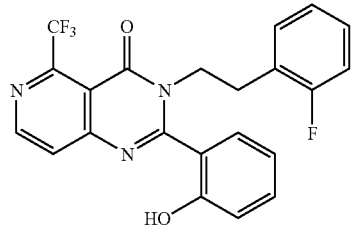

¹H NMR (400 MHz, CD₃OD) δ 8.8 (d, 1H), 7.75 (d, 1H), 7.4 (m, 1H), 7.2 (m, 1H), 6.8-7 (m, 6H), 4.2 (t, 2H), 2.95 (t, 2H). MS m/z 430.1 (M+H)⁺.

EXAMPLE 8

2-(2-Hydroxyphenyl)-3-(3-fluorophenyl)ethyl)-5-trifluoromethyl-3H-pyrido[4,3-d]pyrimidin-4-one

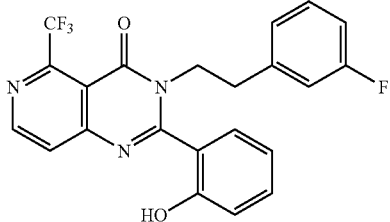

$^1$H NMR (400 MHz, CD$_3$OD) δ 8.8 (d, 1H), 7.75 (d, 1H), 7.45 (t, 1H), 7.15 (m, 2H), 7 (m, 2H), 6.9 (m, 1H), 6.65 (d, 1H), 6.55 (d, 1H), 4.15 (t, 2H), 2.9 (t, 2H). MS m/z 430.1 (M+H)$^+$.

EXAMPLE 9

2-(3-Fluoro-2-hydroxy-phenyl)-3-[2-(2-fluoro-phenyl)-ethyl]-5-trifluoromethyl-3H-pyrido[4,3-d]pyrimidin-4-one

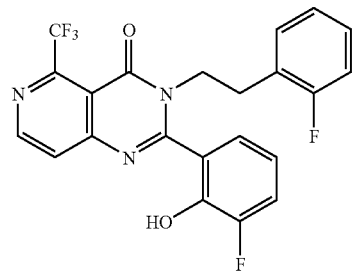

$^1$H NMR (400 MHz, CD$_3$OD) δ 8.85 (d, 1H), 7.8 (d, 1H), 7.35 (m, 1H), 7.2 (m, 1H), 7 (m, 2H), 6.9 (m, 1H), 6.65 (d, 1H), 6.6 (d, 1H), 4.15 (t, 2H), 2.9 (t, 2H). MS m/z 448.2 (M+H)$^+$.

EXAMPLE 10

2-(2-Hydroxy-phenyl)-7-methyl-3-(phenyl-ethyl)-5-trifluoromethyl-3H-pyrido[4,3-d]pyrimidin-4-one

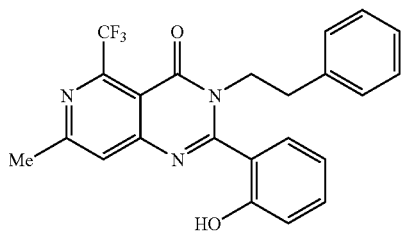

$^1$H NMR (400 MHz, CDCl$_3$) δ 7.6 (s, 1H), 7.45 (m, 1H), 7.30 (m, 1H), 7.12 (m, 5H), 6.90 (m, 2H), 4.44 (m, 2H), 2.99 (m, 2H), 2.80 (s, 3H). MS m/z 426.3 (M+H)$^+$.

EXAMPLE 11

2-(3-Fluoro-2-hydroxy-phenyl)-3-[2-(3-fluoro-phenyl)-ethyl]-5-trifluoromethyl-3H-pyrido[4,3-d]pyrimidin-4-one

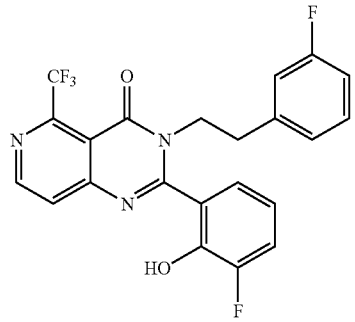

$^1$H NMR (400 MHz, CD$_3$OD) δ 8.8 (d, 1H), 7.75 (d, 1H), 7.25 (m, 1H), 7.2 (m, 1H), 6.8-7 (m, 4H), 6.75 (d, 1H), 4.2 (t, 2H), 2.95 (t, 2H). MS m/z 448.2 (M+H)$^+$.

EXAMPLE 12

3-[2-(2-Fluoro-phenyl)-ethyl]-2-(3-hydroxy-pyridin-2-yl)-5-trifluoromethyl-3H-pyrido[4,3-d]pyrimidin-4-one

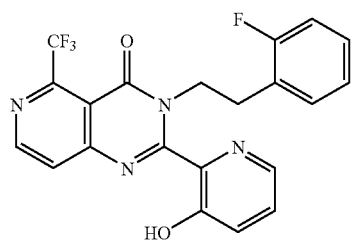

$^1$H NMR (400 MHz, (CD$_3$)$_2$SO) δ 9.89 (s, 1H), 8.95 (d, 1H), 8.25 (d, 1H), 7.95 (d, 1H), 7.50 (m, 2H), 7.25 (m, 1H), 7.00 (m, 3H), 4.11 (m, 2H), 2.99 (m, 2H). MS m/z 431.1 (M+H)$^+$.

EXAMPLE 13

3-[2-(3,4-Difluoro-phenyl)-ethyl]-2-(3-hydroxy-pyridin-2-yl)-5-trifluoromethyl-3H-pyrido[4,3-d]pyrimidin-4-one

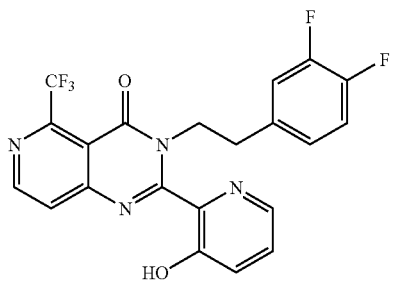

$^1$H NMR (400 MHz, CDCl$_3$) δ 12.66 (brs, 1H), 8.86 (d, 1H), 8.30 (d, 1H), 7.66 (d, 1H), 7.44 (m, 2H), 7.10-6.95 (m, 3H), 4.84 (t, 2H), 3.24 (t, 2H). MS (LC-MS) 449.2 (M+H)$^+$.

EXAMPLE 14

3-[2-(2,4-Difluoro-phenyl)-ethyl]-2-(3-hydroxy-pyridin-2-yl)-5-trifluoromethyl-3H-pyrido[4,3-d]pyrimidin-4-one

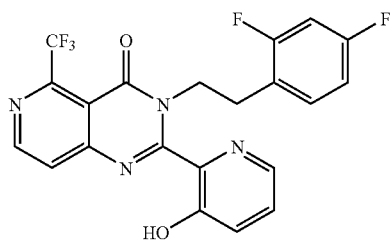

$^1$H NMR (400 MHz, CDCl$_3$) rotomeric mixture δ 12.40 (brs), 8.85 (d), 8.82 (d), 8.25 (m), 7.68 (d), 7.65 (d), 7.37 (m), 7.15 (q), 7.06 (m), 6.71 (m), 4.98 (t), 4.20 (t), 3.23 (t), 3.13 (t). MS (LC-MS) 449.2 (M+H)$^+$.

EXAMPLE 15

3-[2-(3,4-Difluoro-phenyl)-ethyl]-2-(3-hydroxy-pyridin-2-yl)-5-trifluoromethyl-3H-pyrido[4,3-d]pyrimidin-4-one

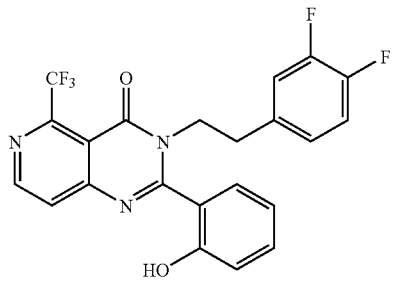

$^1$H NMR (400 MHz, CDCl$_3$) δ 8.83 (d, 1H), 7.84 (brs, 1H), 7.67 (d, 1H), 7.44 (dt, 1H), 7.28 (dd, 1H), 7.04 (t, 1H), 7.02 (d, 1H), 6.91 (q, 1H), 6.59 (m, 2H), 4.34 (t, 2H), 2.88 (t, 2H). MS (LC-MS) 448.2 (M+H)$^+$.

EXAMPLE 16

2-(2-Hydroxy-phenyl)-5-methylamino-3-phenethyl-3H-pyrido[4,3-d]pyrimidin-4-one

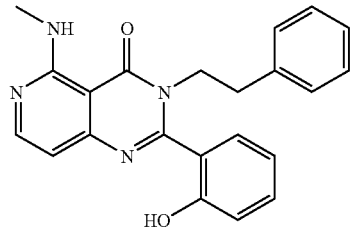

5-Chloro-2-(2-hydroxy-phenyl)-3-phenethyl-3H-pyrido[4,3-d]pyrimidin-4-one, (obtained from Example 1, Preparation 1c and deprotection 1f), (0.0048 mmol, 1 equiv.) was dissolved in methanol (0.5 mL) then 500 uL of methylamine (2M solution in methanol) was added. The reaction mixture was then heated to 50° C. for 48 hour. The solvent was removed and crude products purified by preparative HPLC or preparative TLC (80% ethyl acetate in hexane).

$^1$H NMR (400 MHz, CD$_3$OD) δ 8.17 (d, 1H), 7.40 (t, 1H), 7.15 (m, 3H), 7.05 (d, 1H), 6.94 (m, 2H), 6.80 (m, 2H), 6.59 (d, 1H), 4.10 (t, 2H), 3.08 (s, 3H), 2.85 (t, 2H). MS m/z 373.2 (M+H)$^+$.

The following title compounds (Examples 17-23) may be prepared in a manner analogous to Example 16 using procedures from Example 16 with the corresponding amine followed by deprotection conditions employing BCl$_3$ found in the final step of Example 1.

EXAMPLE 17

2-(2-Hydroxy-phenyl)-5-isopropylamino-3-phenethyl-3H-pyrido[4,3-d]pyrimidin-4-one

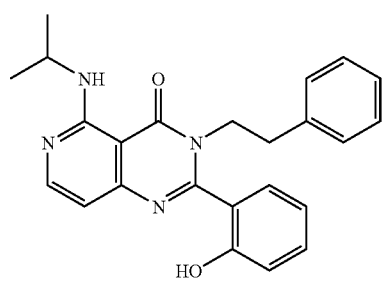

$^1$H NMR (400 MHz, CD$_3$OD) δ 9.00 (m, 1H), 8.17 (d, 1H), 7.40 (t, 1H), 7.15 (m, 3H), 7.05 (d, 1H), 6.94 (m, 2H), 6.80 (m, 2H), 6.59 (d, 1H), 4.30 (m, 1H), 4.09 (t, 2H), 2.85 (t, 2H), 1.32 (d, 6H). MS m/z 401.3 (M+H)$^+$.

EXAMPLE 18

2-(2-Hydroxy-phenyl)-3-phenethyl-5-pyrrolidin-1-yl-3H-pyrido[4,3-d]pyrimidin-4-one

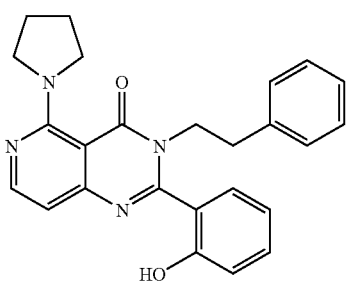

$^1$H NMR (400 MHz, CD$_3$OD) δ 8.12 (d, 1H), 7.41 (t, 1H), 7.14 (m, 4H), 6.95 (m, 2H), 6.85 (m, 2H), 6.70 (d, 1H), 4.12 (t, 2H), 3.51 (t, 4H), 2.81 (t, 2H), 1.97 (m, 4H). MS m/z 413.2 (M+H)$^+$.

EXAMPLE 19

2-(2-Hydroxy-phenyl)-5-(4-methyl-piperazin-1-yl)-3-phenethyl-3H-pyrido[4,3-d]pyrimidin-4-one

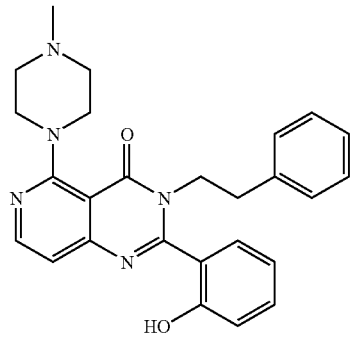

$^1$H NMR (400 MHz, CD$_3$OD) δ 8.27 (d, 1H), 7.4 (m, 1H), 7.11-7.15 (m, 4H), 6.94 (m, 2H), 6.88 (d, 1H), 6.82 (m, 2H), 4.15 (t, 2H), 3.46 (bs, 4H), 2.80 (t, 2H), 2.65 (t, 4H), 2.36 (S, 3H). MS m/z 440.1 (M+H)$^+$.

EXAMPLE 20

2-(2-Hydroxy-phenyl)-3-phenethyl-5-piperazin-1-yl-3H-pyrido[4,3-d]pyrimidin-4-one

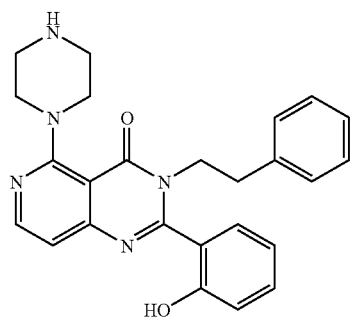

$^1$H NMR (400 MHz, CD$_3$OD) δ 8.26 (d, 1H), 7.41 (t, 1H), 7.14-7.10 (m, 4H), 6.92-6.96 (m, 2H), 6.89 (d, 1H), 6.83-6.81 (m, 2H), 4.16 (t, 2H), 3.42 (t, 4H), 3.04 (t, 4H), 2.79-2.83 (m, 2H). MS m/z 428.2 (M+H)$^+$.

EXAMPLE 21

5-Dimethylamino-2-(2-hydroxy-phenyl)-3-phenethyl-3H-pyrido[4,3-d]pyrimidin-4-one

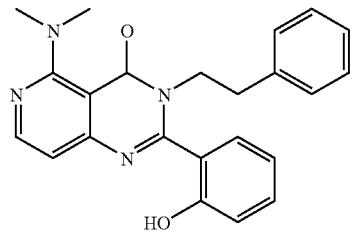

$^1$H NMR (400 MHz, CD$_3$OD) δ 8.19 (d, 1H), 7.39-7.43 (m, 1H), 7.15-7.09 (m, 4H), 6.98-6.94 (m, 2H), 6.83-6.80 (m, 2H), 6.75 (d, 1H), 4.11 (t, 2H), 3.07 (s, 6H), 2.82 (t, 2H). MS m/z 387.1 (M+H)$^+$.

EXAMPLE 22

2-(2-Hydroxy-phenyl)-5-morpholin-4-yl-3-phenethyl-3H-pyrido[4,3-d]pyrimidin-4-one

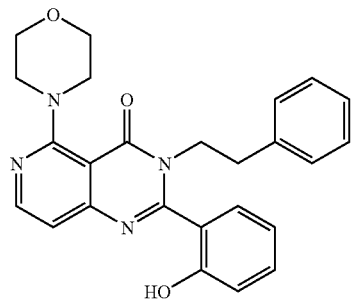

$^1$H NMR (400 MHz, CD$_3$OD) δ 8.28 (d, 1H), 7.44-7.39 (m, 1H), 7.15-7.11 (m, 4H), 6.99-6.95 (m, 2H), 6.89 (d, 1H), 6.83-6.81 (m, 2H), 4.14 (t, 2H), 3.86 (t, 4H), 3.41 (t, 4H), 2.81 (t, 2H). MS m/z 429.2 (M+H)$^+$.

EXAMPLE 23

5-Azetidin-1-yl-2-(2-hydroxy-phenyl)-3-phenethyl-3H-pyrido[4,3-]d-pyrimidin-4-one

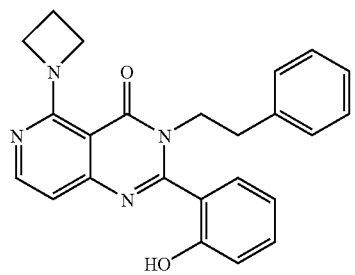

$^1$H NMR (400 MHz, CD$_3$OD) δ 8.19 (d, 1H), 7.4 (t, 1H), 7.15-7.13 (m, 3H), 7.07-7.04 (m, 1H), 6.95-6.93 (m, 2H), 6.82-6.8 (m, 2H), 6.71 (d, 1H), 4.26 (t, 4H), 4.09 (t, 2H), 2.82 (t, 2H), 2.37 (q, 2H). MS m/z 399.1 (M+H)$^+$.

EXAMPLE 24

Preparation of 2-(2-Hydroxy-phenyl)-3-phenethyl-5-phenyl-3H-pyrido[4,3-d]pyrimidin-4-one

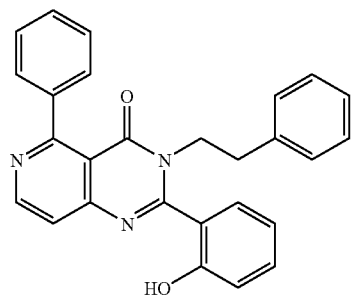

5-Chloro-2-(2-methoxy-phenyl)-3-phenethyl-3H-pyrido [4,3-d]pyrimidin-4-one, phenylboronic acid (1.1 equiv.), palladium tetrakis(triphenylphosphine) (7 mol %) and 2N aqueous Na$_2$CO$_3$ (4 equiv.) were combined in dioxane (0.5 mL)

and heated in a microwave for 15 minutes to 140° C. The reaction mixture was cooled to room temperature, diluted with water and extracted (3×) with ethyl acetate. The combined organic extracts were washed with brine, dried over anhydrous MgSO$_4$ and filtered. The crude products were purified on preparative TLC using 1:1 ethyl acetate:hexane. The desired product can be obtained by using the methyl ether deprotection conditions employing BCl$_3$ and isolation conditions found in the final step of Example 1. $^1$H NMR (400 MHz, CDCl$_3$) δ 8.90 (s, 1H), 8.78 (d, 1H), 7.53 (m, 2H), 7.46 (m, 3H), 7.37 (t, 1H), 7.29 (d, 1H), 7.13 (m, 3H), 6.97 (m, 2H), 6.77 (m, 2H), 4.30 (t, 2H), 2.79 (t, 2H). MS m/z 420.4 (M+H)$^+$.

The following title compounds (Examples 25-29) may be prepared in a manner analogous to Example 24 using procedures from Example 24 with the corresponding boronic acid followed by deprotection conditions employing BCl$_3$ and isolation conditions found in the final step of Example 1.

EXAMPLE 25

5-Benzyl-2-(2-hydroxy-phenyl)-3-phenethyl-3H-pyrido[4,3-d]pyrimidin-4-one

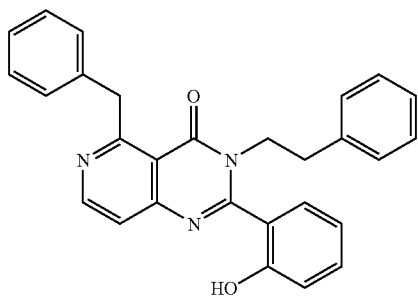

$^1$H NMR (400 MHz, CDCl$_3$) δ 9.40 (s, 1H), 7.58 (d, 1H), 7.40-7.26 (m, 4H), 7.24 (m, 2H), 7.12 (m, 5H), 6.96 (m, 2H), 6.74 (m, 2H), 4.87 (s, 2H), 4.29 (t, 2H), 2.81 (t, 2H). MS m/z 434.3 (M+H)$^+$.

EXAMPLE 26

2-(2-Hydroxy-phenyl)-5-methyl-3-phenethyl-3H-pyrido[4,3-d]pyrimidi-4-one

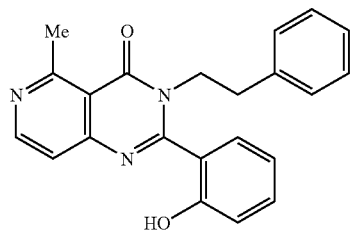

$^1$H NMR (400 MHz, CDCl$_3$) δ 8.44 (d, 1H), 7.42 (m, 2H), 7.30-7.10 (m, 5H), 7.00 (m, 1H); 6.82 (m, 2H), 4.30 (t, 2H), 3.16 (s, 3H), 2.89 (t, 2H). MS m/z 358.3 (M+H)$^+$.

EXAMPLE 27

5-(6-Dimethylamino-pyridin-3-yl)-2-(2-hydroxy-phenyl)-3-phenethyl-3H-pyrido[4,3-d]pyrimidin-4-one

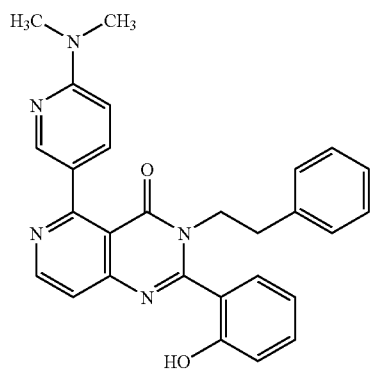

$^1$H NMR (400 MHz, CD$_3$OD) δ 8.72 (d, 1H), 8.30 (s, 1H), 7.72 (d, 1H), 7.46 (m, 2H), 7.15 (m, 4H), 7.00 (m, 2H), 6.80 (m, 2H), 6.73 (d, 1H), 4.08 (t, 2H), 3.19 (s, 6H), 2.80 (t, 2H). MS m/z 464.4 (M+H)$^+$.

EXAMPLE 28

5-(6-Dimethylamino-5-methyl-pyridin-3-yl)-2-(2-hydroxy-phenyl)-3-phenethyl-3H-pyrido[4,3-d]pyrimidin-4-one

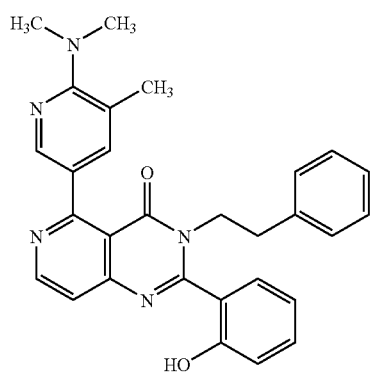

$^1$H NMR (400 MHz, CD$_3$OD) δ 8.77 (d, 1H), 8.20 (s, 1H), 7.66 (s, 1H), 7.54 (d, 1H), 7.45 (m, 1H), 7.19 (d, 1H), 7.12 (m, 3H), 6.99 (m, 2H), 6.78 (m, 2H), 4.09 (t, 2H), 2.87 (s, 6H), 2.80 (t, 2H), 2.40 (s, 3H). MS m/z 478.4 (M+H)$^+$.

EXAMPLE 29

5-(6-pyrrolidine-5-pyridin-3-yl)-2-(2-hydroxy-phenyl)-3-phenethyl-3H-pyrido[4,3-d]pyrimidin-4-one

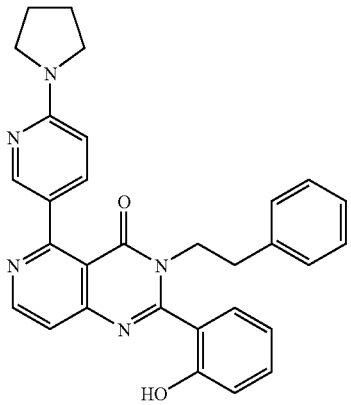

¹H NMR (400 MHz, CD₃OD) δ 8.72 (d, 1H), 8.28 (s, 1H), 7.72 (d, 1H), 7.45 (m, 2H), 7.19 (d, 1H), 7.15 (m, 3H), 6.99 (m, 2H), 6.79 (m, 2H), 6.58 (d, 1H), 4.09 (t, 2H), 3.55 (t, 4H), 2.80 (t, 2H), 2.07 (m, 4H). MS m/z 490.4 (M+H)⁺.

EXAMPLE 30

Preparation of 2-(2-Hydroxy-phenyl)-5-methoxy-3-phenethyl-3H-pyrido[4,3-d]pyrimidin-4-one Preparation of 2-(2-Benzyloxy-phenyl)-5-chloro-3-phenethyl-3H-pyrido[4,3-d]pyrimidin-4-one

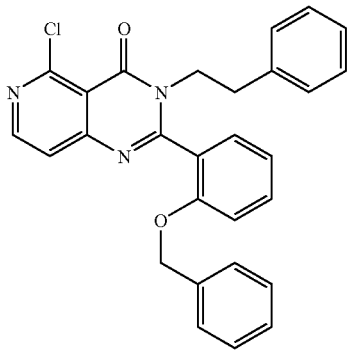

5-Chloro-2-(2-methoxy-phenyl)-3-phenethyl-3H-pyrido[4,3-d]pyrimidin-4-one was subjected to the same deprotection conditions found in the final step of Example 1 to provide the desired 5-chloro-2-(2-hydroxy-phenyl)-3-phenethyl-3H-pyrido[4,3-d]pyrimidin-4-one. A mixture of 5-chloro-2-(2-hydroxy-phenyl)-3-phenethyl-3H-pyrido[4,3-d]pyrimidin-4-one (88 mg, 0.233 mmol), potassium carbonate (64 mg, 0.466 mmol, 2 equiv.) and benzyl bromide (0.029 mL, 0.245 mmol, 1.05 equiv.) in 2 mL of acetone was heated to reflux overnight. The reaction mixture was cooled to RT, filtered through celite, concentrated and the residue purified on preparative TLC plate using 1:1 ethyl acetate:heptane to give 95 mg (87%) of the desired product.

Preparation of 2-(2-Benzyloxy-phenyl)-5-methoxy-3-phenethyl-3H-pyrido[4,3-d]pyrimidin-4-one

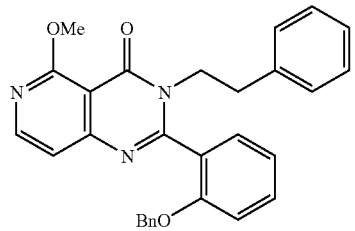

A mixture of 2-(2-benzyloxy-phenyl)-5-chloro-3-phenethyl-3H-pyrido[4,3-d]pyrimidin-4-one, sodium hydride (60% suspension in mineral oil) (1.5 equiv.), and corresponding alcohol (1.5 equiv.) in THF was heated at 70° C. overnight. The reaction was cooled to RT, solvent removed, water and ethyl acetate were added and phases separated. The aqueous phase was washed with ethyl acetate (2×), organic portions combined, washed with water, brine, dried over anhydrous MgSO₄, filtered and concentrated. The residue was purified on preparative TLC plate using 1:1 ethyl acetate: heptane.

2-(2-Hydroxy-phenyl)-5-methoxy-3-phenethyl-3H-pyrido[4,3-d]pyrimidin-4-one

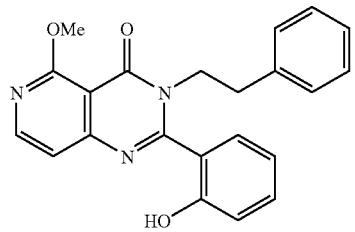

2-(2-Benzyloxy-phenyl)-5-methoxy-3-phenethyl-3H-pyrido[4,3-d]pyrimidin-4-one dissolved in methanol (0.05M) was subjected to H-cube hydrogenation (room temperature, Pd/C cartridge). Solvent was then removed and product purified on preparative TLC plate to afford the desired 2-(2-Hydroxy-phenyl)-5-methoxy-3-phenethyl-3H-pyrido[4,3-d]pyrimidin-4-one.

¹H NMR (400 MHz, CD₃OD) δ 8.33 (d, 1H), 7.42 (t, 1H), 7.16 (m, 3H), 7.05 (m, 2H), 6.95 (m, 2H), 6.80 (m, 2H), 4.10 (m, 5H), 2.86 (t, 2H). MS m/z 374.2 (M+H)⁺.

The following title compounds (Examples 31-36) may be prepared in a manner analogous to Example 30 using procedures from Example 30 with the corresponding alcohol followed by H-cube hydrogenation.

EXAMPLE 31

2-(2-Hydroxy-phenyl)-5-(1-methyl-cyclopropyl-methoxy)-3-phenethyl-3H-pyrido[4,3-d]pyrimidin-4-one

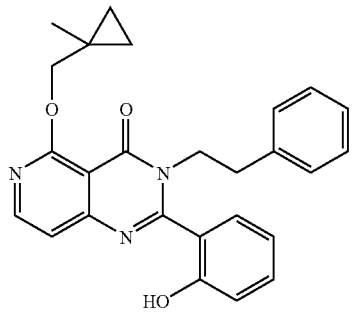

$^1$H NMR (400 MHz, CD$_3$OD) δ 8.33 (d, 1H), 7.45 (t, 1H), 7.19 (m, 3H), 7.12 (d, 1H), 7.05 (d, 1H), 7.00 (m, 2H), 6.83 (m, 2H), 4.39 (s, 2H), 4.12 (t, 2H), 2.91 (t, 2H), 1.32 (s, 3H), 0.70 (t, 2H), 0.47 (t, 2H). MS m/z 428.2 (M+H)$^+$.

EXAMPLE 32

2-(2-Hydroxy-phenyl)-3-phenethyl-5-propoxy-3H-pyrido[4,3-d]pyrimidin-4-one

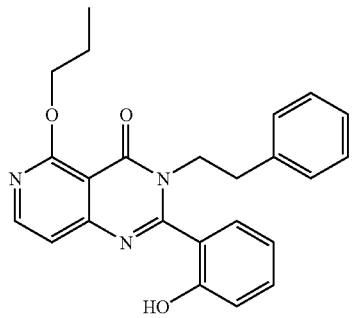

$^1$H NMR (400 MHz, CD$_3$OD) δ 8.33 (d, 1H), 7.45 (t, 1H), 7.19 (m, 3H), 7.12 (d, 1H), 7.05 (d, 1H), 7.00 (m, 2H), 6.83 (m, 2H), 4.52 (t, 2H), 4.12 (t, 2H), 2.91 (t, 2H), 1.93 (m, 2H), 1.12 (t, 3H). MS m/z 402.2 (M+H)$^+$.

EXAMPLE 33

5-Cyclobutyloxy-2-(2-hydroxy-phenyl)-3-phenethyl-3H-pyrido[4,3-d]pyrimidin-4-one

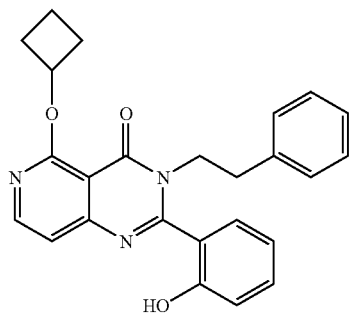

$^1$H NMR (400 MHz, CD$_3$OD) δ 8.33 (d, 1H), 7.45 (t, 1H), 7.19 (m, 3H), 7.12 (d, 1H), 7.05 (d, 1H), 7.00 (m, 2H), 6.83 (m, 2H), 5.41 (m, 1H), 4.12 (t, 2H), 2.91 (t, 2H), 2.55 (m, 2H), 2.36 (m, 2H), 1.93 (m, 1H), 1.76 (m, 1H). MS m/z 414.2 (M+H)$^+$.

EXAMPLE 34

2-(2-Hydroxy-phenyl)-5-isobutoxy-3-phenethyl-3H-pyrido[4,3-d]pyrimidin-4-one

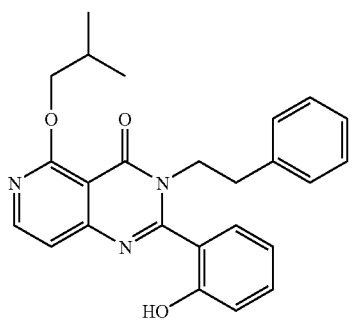

$^1$H NMR (400 MHz, CD$_3$OD) δ 8.33 (d, 1H), 7.45 (t, 1H), 7.19 (m, 3H), 7.12 (d, 1H), 7.05 (d, 1H), 7.00 (m, 2H), 6.83 (m, 2H), 4.33 (d, 2H), 4.12 (t, 2H), 2.91 (t, 2H), 2.28 (m, 1H), 1.12 (d, 6H). MS m/z 416.3 (M+H)$^+$.

EXAMPLE 35

2-(2-Hydroxy-phenyl)-5-isopropoxy-3-phenethyl-3H-pyrido[4,3-d]pyrimidin-4-one

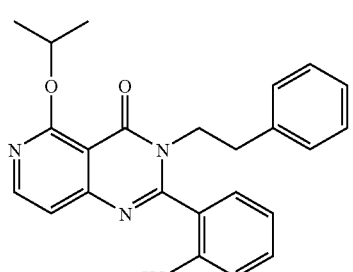

$^1$H NMR (400 MHz, CD$_3$OD) δ 8.34 (d, 1H), 7.46 (t, 1H), 7.19 (m, 3H), 7.10 (d, 1H), 7.04 (d, 1H), 7.00 (m, 2H), 6.82 (m, 2H), 5.61 (m, 1H), 4.12 (t, 2H), 2.90 (t, 2H), 1.50 (d, 6H). MS m/z 402.3 (M+H)$^+$.

EXAMPLE 36

2-(2-Hydroxy-phenyl)-3-phenethyl-5-(2,2,2-trifluoro-ethoxy)-3H-pyrido[4,3-d]pyrimidin-4-one

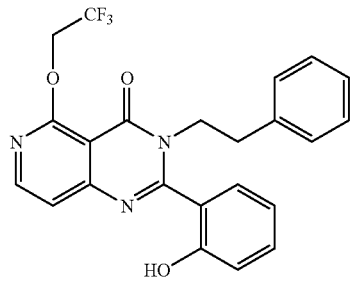

$^1$H NMR (400 MHz, CD$_3$OD) δ 8.36 (d, 1H), 7.45 (t, 1H), 7.15 (m, 5H), 7.00 (m, 2H), 6.83 (m, 2H), 5.10 (q, 2H), 4.15 (m, 2H), 2.90 (t, 2H). MS m/z 442.2 (M+H)$^+$.

EXAMPLE 37

Preparation of 3-(1-(3,4-difluorophenyl)propan-2-yl)-2-(3-hydroxypyridin-2-yl) 5-(trifluoromethyl) pyrido[4,3-d]pyrimidin-4(3H)-one

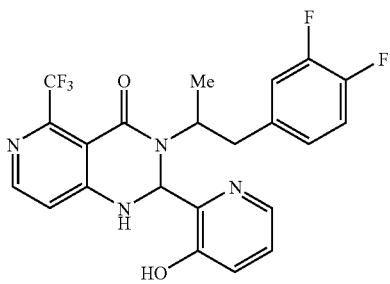

2-(3-(benzyloxy)pyridin-2-yl)-3-(1-(3,4-difluorophenyl)propan-2-yl)-5-(trifluoromethyl)-2,3-dihydropyrido[4,3-d]pyrimidin-4(1H)-one (12.1 grams, 21.8 mmol) prepared by the same reactions conditions described above was dissolved in 300 mL of ethanol and added to a parr bottle that contained 10% Pd(C). The mixture was subjected to hydrogenation condition (45 psi) for two hours. At this time, the reaction mixture was filtered through Celite and washed with ethanol. The fitrate was concentrated in vacuo and purified by silica gel chromatography to afford a pale yellow foam of 3-(1-(3,4-difluorophenyl)propan-2-yl)-2-(3-hydroxypyridin-2-yl)-5-(trifluoromethyl)-2,3-dihydropyrido[4,3-d]pyrimidin-4(1H)-one.

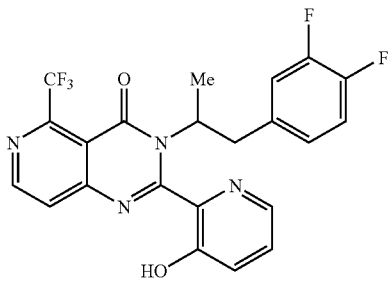

3-(1-(3,4-difluorophenyl)propan-2-yl)-2-(3-hydroxypyridin-2-yl)-5-(trifluoromethyl)-2,3-dihydropyrido[4,3-d]pyrimidin-4(1H)-one (5.90 g, 12.7 mmol) was dissolved in 500 mL of 4-methyl-2-pentanone. To this solution, manganese dioxide was added (16.6 g, 191 mmol) and the mixture was heated to 90° C. for 1 hour. The reaction was cooled, filtered through Celite and washed with CH$_2$CL$_2$. The filtrate was collected and concentrated in vacuo as a yellow solid which was purified by silica gel chromatography to afford the racemic mixture 3-(1-(3,4-difluorophenyl)propan-2-yl)-2-(3-hydroxypyridin-2-yl)-5-(trifluoromethyl)pyrido[4,3-d]pyrimidin-4(3H)-one.

The racemic compound of Example 37 can be separated into its single enantiomer components (Examples 37a and 37b) by preparative chromatography on a Chiralcel OD-H (2.1 cm×25 cm) column (Daicel (U.S.A.) Chemical Industries, Ltd, Fort Lee, N.J. 07024, U.S.A.) using MeOH/CHCL$_3$ (3/1) as mobile phase at a flow rate of 65 g/min.

EXAMPLE 37a (R)-3-(1-(3,4-difluorophenyl)propan-2-yl)-2-(3-hydroxypyridin-2-yl) 5-(trifluoromethyl)pyrido[4,3-d] pyrimidin-4(3H)-one

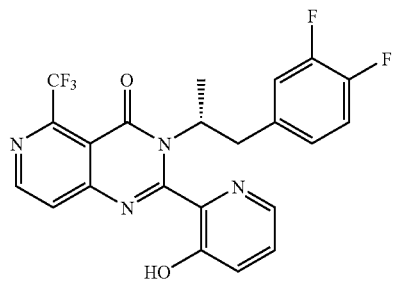

$^1$H NMR (400 MHz, CDCl$_3$) δ 11.4 (s, 1H), 8.85 (d, 1H), 8.39 (d, 1H), 7.60 (d, 1H), 7.42 (m 2H), 6.99 (m, 2H), 6.67 (brs, 1H), 5.24 (m, 1H), 3.63 (m, 1H), 3.24 (m, 1H), 1.90 (d, 3H). MS m/z 463.3 (M+H)$^+$.

EXAMPLE 37b (S)-3-(1-(3,4-difluorophenyl)propan-2-yl)-2-(3-hydroxypyridin-2-yl) 5-(trifluoromethyl)pyrido[4,3-d] pyrimidin-4(3H)-one

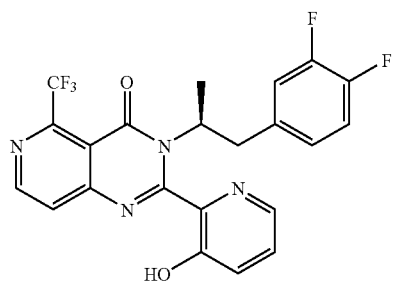

$^1$H NMR (400 MHz, CDCl$_3$) δ 11.4 (s, 1H), 8.85 (d, 1H), 8.39 (d, 1H), 7.60 (d, 1H), 7.42 (m, 2H), 6.99 (m, 2H), 6.67 (brs, 1H), 5.24 (m, 1H), 3.63 (m, 1H), 3.24 (m, 1H), 1.90 (d, 3H). MS m/z 463.3 (M+H)$^+$.

EXAMPLE 38a 3-(1-(2,4-difluorophenyl)propan-2-yl)-2-(3-hydroxy-pyridin-2-yl)-5-(trifluoromethyl)pyrido[4,3-d]pyrimidin-4(3H)-one

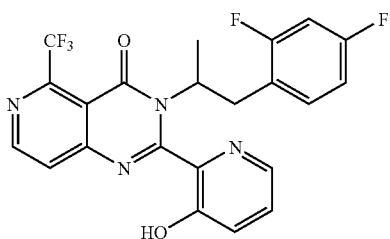

$^1$H NMR (400 MHz, CDCl$_3$) δ 8.90 (d, 1H), 8.30 (d, 1H), 7.60 (d, 1H), 7.42 (m, 2H), 6.99 (m, 1H), 6.66 (m, 2H), 5.65 (m, 1H), 3.63 (m, 1H), 3.20 (m, 1H), 1.90 (d, 3H). MS m/z 463.2 (M+H)$^+$.

EXAMPLE 38b 3-(1-(2,4-difluorophenyl)propan-2-yl)-2-(3-hydroxy-pyridin-2-yl)-5-(trifluoromethyl)pyrido[4,3-d]pyrimidin-4(3H)-one

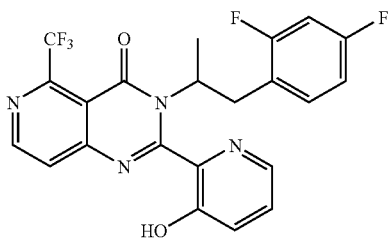

$^1$H NMR (400 MHz, CDCl$_3$) δ 8.90 (d, 1H), 8.30 (d, 1H), 7.60 (d, 1H), 7.42 (m, 2H), 6.99 (m, 1H), 6.66 (m, 2H), 5.65 (m, 1H), 3.63 (m, 1H), 3.20 (m, 1H), 1.90 (d, 3H). MS m/z 463.2 (M+H)$^+$.

EXAMPLE 39

3-(2-methoxyphenethyl)-2-(3-hydroxypyridin-2-yl)-5-(trifluoromethyl)pyrido[4,3-d]pyrimidin-4(3H)-one

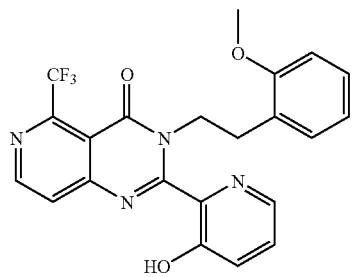

$^1$H NMR (400 MHz, CDCl$_3$) δ 10.64 (s, 1H), 8.87 (d, 1H), 8.17 (dd, 1H), 7.87 (d, 1H), 7.46 (dq, 2H), 7.10 (dt, 1H), 6.81 (t, 1H), 6.79 (t, 1H), 6.721 (t, 1H), 3.97 (t, 2H), 3.45 (s, 3H), 2.75 (t, 2H). MS m/z 443.1 (M+H)$^+$.

EXAMPLE 40

3-(2,3-difluorophenethyl)-2-(3-hydroxypyridin-2-yl)-5-(trifluoromethyl)pyrido[4,3-d]pyrimidin-4(3H)-one

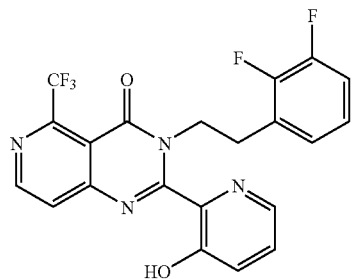

$^1$H NMR (400 MHz, CDCl$_3$) δ 8.85 (d, 1H), 8.28 (m, 1H), 7.65 (d, 1H), 7.37 (m, 2H), 6.95 (m, 4H), 5.01 (t, 2H), 3.31 (t, 2H). MS m/z 449.1 (M+H)$^+$.

EXAMPLE 41

3-(5-fluoro-2-methoxyphenethyl)-2-(3-hydroxypyridin-2-yl)-5-(trifluoromethyl)pyrido[4,3-d]pyrimidin-4(3H)-one

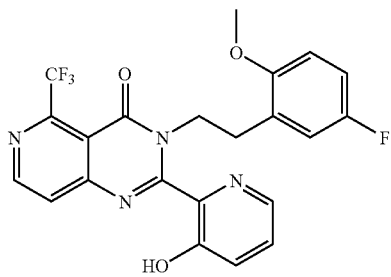

$^1$H NMR (400 MHz, CDCl$_3$) δ 8.90 (d, 1H), 8.20 (d, 1H), 7.70 (d, 1H), 7.38 (m, 2H), 6.80 (m, 1H), 6.56 (m, 2H), 3.40 (s, 3H), 3.01 (m, 2H). MS m/z 461.2 (M+H)$^+$.

EXAMPLE 42

3-(2-fluoro-6-methoxyphenethyl)-2-(3-hydroxypyridin-2-yl)-5-(trifluoromethyl)pyrido[4,3-d]pyrimidin-4(3H)-one

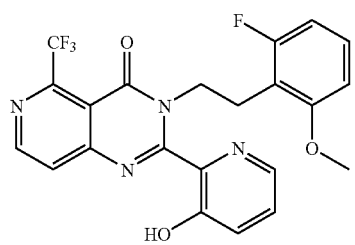

MS m/z 461 (M+H)$^+$.

EXAMPLE 43

2-(3-hydroxypyridin-2-yl)-3-(1-(2-methoxyphenyl)propan-2-yl)-5-(trifluoromethyl)pyrido[4,3-d]pyrimidin-4(3H)-one

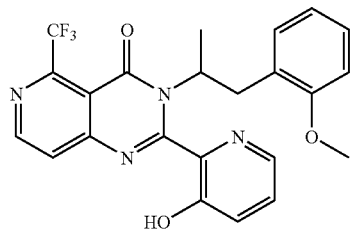

$^1$H NMR (400 MHz, CD$_3$OD) δ 8.90 (d, 1H), 8.10 (m, 1H), 7.70 (d, 1H), 7.40 (m, 2H), 7.10 (t, 1H), 6.90 (d, 1H), 6.70 (d, 1H), 6.61 (t, 1H), 4.45 (m, 1H), 3.40 (s, 3H), 3.39 (m, 1H) 3.01 (m, 2H), 1.75 (d, 3H). MS m/z 457.3 (M+H)$^+$.

EXAMPLE 43a 2-(3-hydroxypyridin-2-yl)-3-(1-(2-methoxyphenyl)propan-2-yl)-5-(trifluoromethyl)pyrido[4,3-d]pyrimidin-4(3H)-one

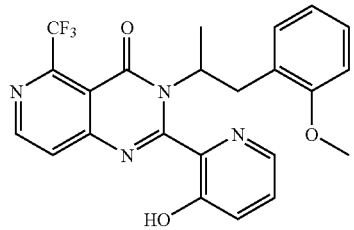

$^1$H NMR (400 MHz, CD$_3$OD) δ 8.90 (d, 1H), 8.10 (m, 1H), 7.70 (d, 1H), 7.40 (m, 2H), 7.10 (t, 1H), 6.90 (d, 1H), 6.70 (d, 1H), 6.61 (t, 1H), 4.45 (m, 1H), 3.40 (s, 3H), 3.39 (m, 1H) 3.01 (m, 2H), 1.75 (d, 3H). MS m/z 457.3 (M+H)$^+$.

EXAMPLE 43b 2-(3-hydroxypyridin-2-yl)-3-(1-(2-methoxyphenyl)propan-2-yl)-5-(trifluoromethyl)pyrido[4,3-d]pyrimidin-4(3H)-one

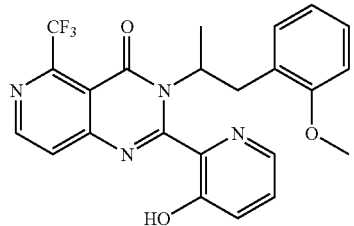

$^1$H NMR (400 MHz, CD$_3$OD) δ 8.90 (d, 1H), 8.10 (m, 1H), 7.70 (d, 1H), 7.40 (m, 2H), 7.10 (t, 1H), 6.90 (d, 1H), 6.70 (d, 1H), 6.61 (t, 1H), 4.45 (m, 1H), 3.40 (s, 3H), 3.39 (m, 1H) 3.01 (m, 2H), 1.75 (d, 3H). MS m/z 457.3 (M+H)$^+$.

EXAMPLE 44

3-(1-(2-fluorophenyl)butan-2-yl)-2-(3-hydroxypyridin-2-yl)-5-(trifluoromethyl)pyrido[4,3-d]pyrimidin-4(3H)-one

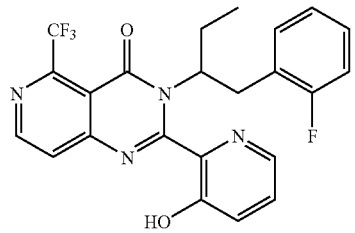

$^1$H NMR (400 MHz, CDCl$_3$) δ 8.75 (d, 1H), 8.07 (brs, 1H), 7.51 (d, 1H), 7.36 (t, 2H), 7.07 (m, 2H), 6.95 (m, 2H), 6.84 (m, 2H), 6.76 (t, 1H), 4.48 (m, 1H), 3.48 (dd, 1H), 3.24 (dd, 1H), 2.41 (m, 1H), 2.29 (m, 1H), 0.91 (t, 3H). MS m/z 458.3 (M+H)$^+$.

EXAMPLE 45

3-(3-fluoro-2-methoxyphenethyl)-2-(3-hydroxypyridin-2-yl)-5-(trifluoromethyl)pyrido[4,3-d]pyrimidin-4(3H)-one

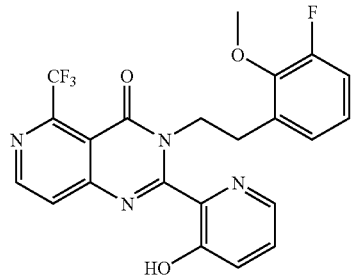

$^1$H NMR (400 MHz, CD$_3$OD) δ 8.90 (d, 1H), 8.18 (d, 1H), 7.80 (d, 1H), 7.45 (m, 2H), 6.99 (m, 1H), 6.85 (m, 1H), 6.79 (d, 1H), 4.25 (m, 2H), 3.60 (s, 3H), 2.99 (m, 2H). MS m/z 461.2 (M+H)$^+$.

EXAMPLE 46

3-(2-cyclopentylethyl)-2-(3-hydroxypyridin-2-yl)-5-(trifluoromethyl)pyrido[4,3-d]pyrimidin-4(3H)-one

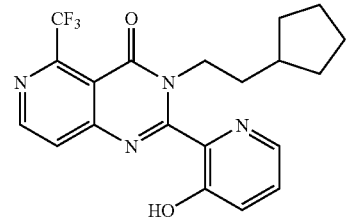

$^1$H NMR (400 MHz, dmso-d$_6$) δ 10.64 (s, 1H), 8.87 (d, 1H), 8.15 (dd, 1H), 7.86 (d, 1H), 7.43 (m, 2H), 3.77 (brm, 2H), 1.48 (brm, 5H), 1.34 (brm, 4H), 0.69 (brm, 2H). MS m/z 405.2 (M+H)$^+$.

EXAMPLE 47

3-(2-cyclohexylethyl)-2-(3-hydroxypyridin-2-yl)-5-(trifluoromethyl)pyrido[4,3-d]pyrimidin-4(3H)-one

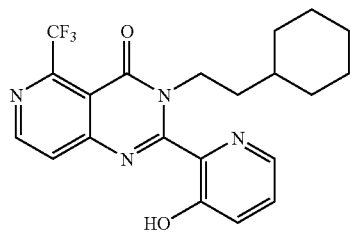

$^1$H NMR (400 MHz, dmso-d$_6$) δ 10.62 (s, 1H), 8.87 (d, 1H), 8.15 (dd, 1H), 7.86 (d, 1H), 7.43 (m, 2H), 3.81 (m, 2H), 1.48 (brm, 5H), 1.50-1.25 (m, 7H), 1.00 (m, 4H), 0.58 (m, 2H). MS m/z 419.2 (M+H)$^+$.

EXAMPLE 48a (R)-3-(1-cyclohexylpropan-2-yl)-2-(3-hydroxypyridin-2-yl)-5-(trifluoromethyl)pyrido[4,3-d]pyrimidin-4(3H)-one

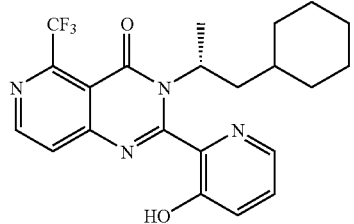

$^1$H NMR (400 MHz, dmso-d$_6$) δ 10.61 (s, 1H), 8.85 (d, 1H), 8.12 (dd, 1H), 7.83 (d, 1H), 7.39 (m, 2H), 3.97 (brs, 1H), 1.82 (m, 1H), 1.72 (m, 1H), 1.46 (m, 2H), 1.42 (d, 3H), 1.35 (m, 2H), 1.17-0.93 (m, 5H), 0.66 (m, 1H), 0.56 (m, 1H). MS m/z 433.3 (M+H)$^+$.

EXAMPLE 48b (S)-3-(1-cyclohexylpropan-2-yl)-2-(3-hydroxypyridin-2-yl)-5-(trifluoromethyl)pyrido[4,3-d]pyrimidin-4(3H)-one

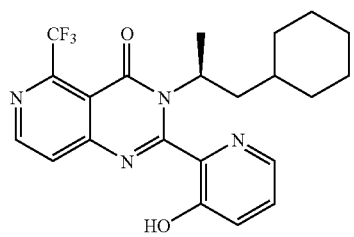

$^1$H NMR (400 MHz, dmso-d$_6$) δ 10.61 (s, 1H), 8.85 (d, 1H), 8.12 (dd, 1H), 7.83 (d, 1H), 7.39 (m, 2H), 3.97 (brs, 1H), 1.82 (m, 1H), 1.72 (m, 1H), 1.46 (m, 2H), 1.42 (d, 3H), 1.35 (m, 2H), 1.17-0.93 (m, 5H), 0.66 (m, 1H), 0.56 (m, 1H). MS m/z 433.3 (M+H)$^+$.

EXAMPLE 49

(R, S)-2-(3-hydroxypyridin-2-yl)-3-(2-(tetrahydro-2H-pyran-2-yl)ethyl)-5-(trifluoromethyl)pyrido[4,3-d]pyrimidin-4(3H)-one

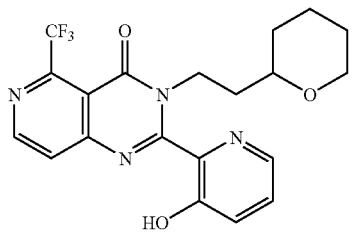

$^1$H NMR (400 MHz, dmso-d$_6$) δ 10.61 (s, 1H), 8.86 (d, 1H), 8.15 (dd, 1H), 7.85 (d, 1H), 7.41 (m, 2H), 3.94 (m, 1H), 3.79 (m, 1H), 3.56 (d, 1H), 3.10 (t, 1H), 3.02 (m, 1H), 1.57 (m, 3H), 1.27 (m, 3H), 1.07 (m, 4H), 0.93 (m, 1H). MS m/z 421.3 (M+H)$^+$.

EXAMPLE 50

(R)-2-(3-fluoro-2-hydroxyphenyl)-3-(1-phenylpropan-2-yl)-5-(trifluoromethyl)pyrido[4,3-d]pyrimidin-4(3H)-one

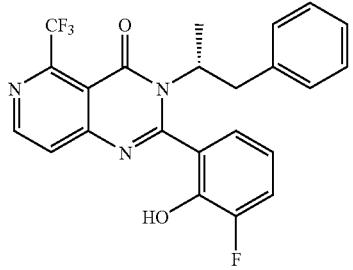

$^1$H NMR (400 MHz, CDCl$_3$) δ 8.80 (d, 1H), 7.60 (d, 1H), 7.2 (m, 5H), 6.90 (m, 1H), 6.80 (m, 1H), 6.67 (brs, 1H), 4.44 (m, 1H), 3.63 (m, 1H), 3.10 (m, 1H), 1.90 (d, 3H). MS m/z 444.3 (M+H)$^+$.

EXAMPLE 51

(R)-2-(1H-imidazol-2-yl)-3-(1-phenylpropan-2-yl)-5-(trifluoromethyl)pyrido[4,3-d]pyrimidin-4(3H)-one

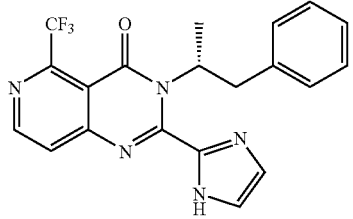

$^1$H NMR (400 MHz, CDCl$_3$) δ 8.79 (d, 1H), 7.58 (d, 1H), 7.4 (s, 1H), 7.30 (d, 1H), 7.10 (m, 4H), 6.98 (m, 1H), 3.70 (m, 1H), 3.30 (m, 1H), 1.90 (d, 3H). MS m/z 400.2 (M+H)$^+$.

EXAMPLE 52

N-(2-(3-(2-fluorophenethyl)-4-oxo-5-(trifluoromethyl)-3,4-dihydropyrido[4,3-d]pyrimidin-2-yl)pyridin-3-yl)acetamide

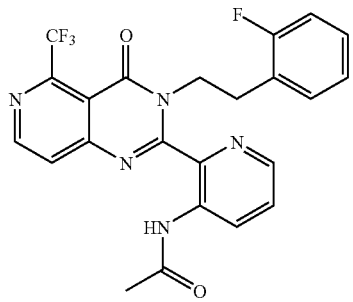

$^1$H NMR (400 MHz, CDCl$_3$) δ 9.40 (brs, 1H), 8.98 (d, 1H), 8.80 (d, 1H), 8.45 (m, 1H), 7.67 (d, 1H), 7.44 (m, 1H), 7.10 (m, 1H), 7.00 (m, 1H), 6.99 (m, 1H), 6.85 (m, 1H), 4.60 (m, 2H), 3.05 (m, 2H), 2.10 (s, 3H). MS m/z 472.1 (M+H)$^+$.

EXAMPLE 53

(R)-3-(1-phenylpropan-2-yl)-2-(thiazol-4-yl)-5-(trifluoromethyl)pyrido[4,3-d]pyrimidin-4(3H)-one

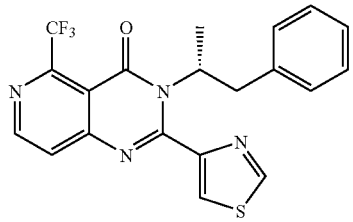

$^1$H NMR (400 MHz, CDCl$_3$) δ 8.99 (s, 1H), 8.89 (d, 1H), 7.60 (d, 1H), 7.59 (s, 1H), 7.10 (m, 3H), 6.98 (m, 2H), 4.61 (m, 1H), 3.61 (m, 2H), 3.10 (m, 2H), 1.90 (d, 3H). MS m/z 417.2 (M+H)$^+$.

EXAMPLE 54

3-phenethyl-2-(thiazol-4-yl)-5-(trifluoromethyl)pyrido[4,3-d]pyrimidin-4(3H)-one

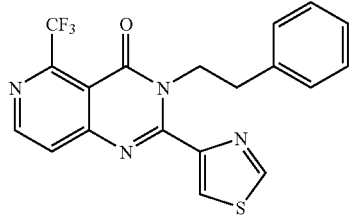

$^1$H NMR (400 MHz, CDCl$_3$) δ 8.99 (s, 1H), 8.89 (d, 1H), 8.01 (s, 1H), 7.70 (d, 1H), 7.22 (m, 5H), 4.60 (m, 2H), 3.15 (m, 2H), 3.24 (m, 1H).

EXAMPLE 55

3-(2-methoxyphenethyl)-2-(2-hydroxyphenyl)-5-(trifluoromethyl)pyrido[4,3-d]pyrimidin-4(3H)-one

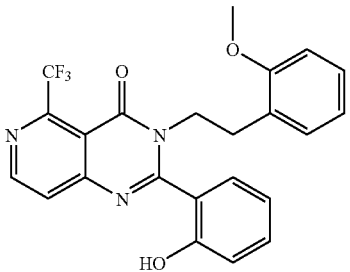

$^1$H NMR (400 MHz, CDCl$_3$) δ 8.82 (d, 1H), 7.65 (d, 1H), 7.40 (m, 1H), 7.20 (m, 2H), 6.90 (m, 2H), 6.79 (d, 1H), 6.65 (m, 2H), 4.60 (t, 2H), 3.40 (s, 3H), 3.01 (t, 2H). MS m/z 442.3 (M+H)$^+$.

EXAMPLE 56

3-(2-fluorophenethyl)-2-(thiazol-4-yl)-5-(trifluoromethyl)pyrido[4,3-d]pyrimidin-4(3H)-one

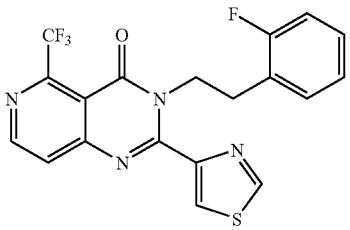

$^1$H NMR (400 MHz, CDCl$_3$) δ 8.99 (s, 1H), 8.89 (d, 1H), 7.90 (s, 1H), 7.79 (d, 1H), 7.22 (m, 5H), 4.68 (m, 2H), 3.15 (m, 2H). MS m/z 421.3 (M+H)$^+$.

EXAMPLE 57

(R)-2-cyclopentyl-3-(1-phenylpropan-2-yl)-5-(trifluoromethyl)pyrido[4,3-d]pyrimidin-4(3H)-one

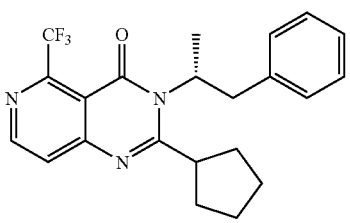

$^1$H NMR (400 MHz, CDCl$_3$) δ 8.79 (d, 1H), 7.59 (d, 1H), 7.2 (m, 5H), 4.67 (brd, 1H), 3.69 (m, 1H), 3.30 (m, 1H), 3.0 (brm, 1H), 1.90 (m, 8H), 1.89 (d, 3H). MS m/z 402.3 (M+H)$^+$.

EXAMPLE 58

2-isopropyl-3-phenethyl-5-(trifluoromethyl)pyrido[4,3-d]pyrimidin-4(3H)-one

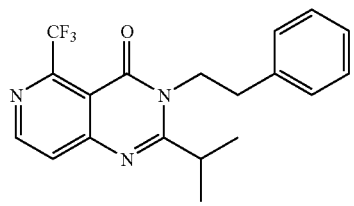

$^1$H NMR (400 MHz, CDCl$_3$) δ 8.80 (d, 1H), 8.65 (d, 1H), 7.35 (m, 5H), 4.42 (m, 2H), 3.13 (m, 2H), 2.99 (m, 1H), 1.90 (d, 6H). MS m/z 362.3 (M+H)$^+$.

EXAMPLE 59

2-cyclopentyl-3-phenethyl-5-(trifluoromethyl)pyrido[4,3-d]pyrimidin-4(3H)-one

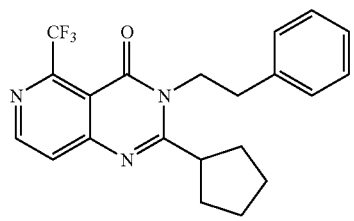

$^1$H NMR (400 MHz, CDCl$_3$) δ 8.79 (d, 1H), 8.65 (d, 1H), 7.35 (m, 5H), 4.40 (m, 2H), 3.10 (m, 2H), 2.00-1.6 (m, 8H). MS m/z 388.3 (M+H)$^+$.

EXAMPLE 60

3-(2-methoxyphenethyl)-2-(thiazol-4-yl)-5-(trifluoromethyl)pyrido[4,3-d]pyrimidin-4(3H)-one

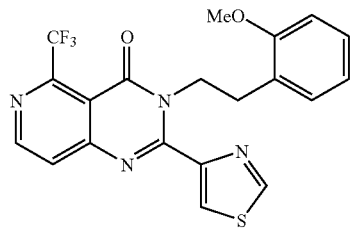

$^1$H NMR (400 MHz, CDCl$_3$) δ 8.89 (t, 2H), 8.70 (d, 1H), 7.45 (s, 1H), 7.10 (m, 1H), 6.79 (m, 1H), 6.70 (m, 1H), 6.60 (d, 1H), 4.80 (m, 2H), 3.40 (s, 3H), 3.0 (t, 2H), MS m/z 433.4 (M+H)$^+$.

EXAMPLE 61

3-(2-cyclohexylethyl)-2-(thiazol-4-yl)-5-(trifluoromethyl)pyrido[4,3-d]pyrimidin-4(3H)-one

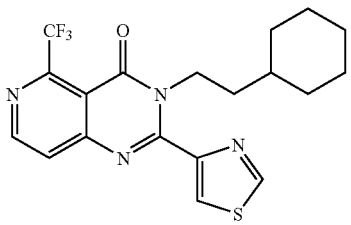

$^1$H NMR (500 MHz, CDCl$_3$) ☐ ppm 0.78-0.95 (m, 2H), 1.07-1.25 (m, 3H), 1.24-1.34 (m, 1H), 1.56-1.74 (m, 7H), 4.35-4.52 (m, 2H), 7.75 (d, 1H), 8.22 (d, 1H), 8.86 (d, 1H), 8.98 (d, 1H). MS m/z 409.5 (M+H)$^+$.

EXAMPLE 62

2-(3-(2-cyclohexylethyl)-4-oxo-5-(trifluoromethyl)-3,4-dihydropyrido[4,3-d]pyrimidin-2-yl)benzonitrile

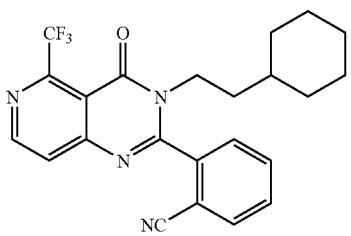

$^1$H NMR (500 MHz, CDCl$_3$) ☐ (ppm) 0.67-0.80 (m, 2H), 1.03-1.20 (m, 4H), 1.44 (d, 2H), 1.50-1.57 (m, 2H), 1.57-1.65 (m, 3H), 3.87-4.02 (m, 2H), 7.64 (d, 1H), 7.70-7.81 (m, 2H), 7.85 (t, 1H), 7.93 (d, 1H), 8.91 (d, 1H). MS m/z 427.5 (M+H)$^+$.

EXAMPLE 63

2-(3-aminopyridin-2-yl)-3-phenethyl-5-(trifluoromethyl)pyrido[4,3-d]pyrimidin-4(3H)-one

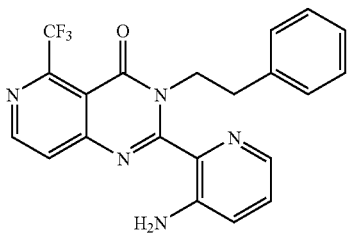

$^1$H NMR (400 MHz, CDCl$_3$) δ 8.84 (d, 1H), 8.17 (q, 1H), 7.69 (d, 1H), 7.27 (m, 1H), 7.18 (m, 4H), 7.06 (m, 2H), 4.68 (s, br, 2H), 4.38 (m, 2H), 3.11 (m, 2H). MS m/z 412.4 (M+H)$^+$.

EXAMPLE 64

N-(2-(4-oxo-3-phenethyl-5-(trifluoromethyl)-3,4-dihydropyrido[4,3-d]pyrimidin-2-yl)pyridin-3-yl)methanesulfonamide

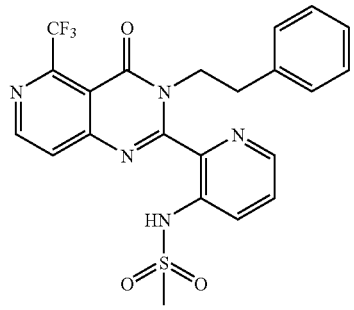

¹H NMR (400 MHz, CDCl₃) δ 8.94 (s, 1H), 8.90 (d, 1H), 8.55 (dd, 1H), 8.12 (dd, 1H), 7.70 (d, 1H), 7.52 (dd, 1H), 7.22 (m, 3H), 7.07 (m, 2H), 4.44 (m, 2H), 3.19 (m, 2H), 3.11 (s, 3H). MS m/z 490.5 (M+H)⁺.

EXAMPLE 65

3-(1-(2-fluorophenyl)propan-2-yl)-2-(thiazol-4-yl)-5-(trifluoromethyl)pyrido[4,3-d]pyrimidin-4(3H)-one

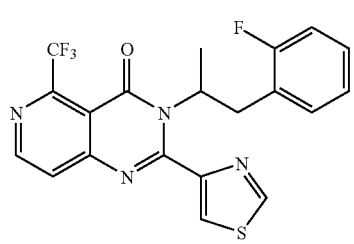

¹H NMR (400 MHz, CDCl₃) δ 8.99 (s, 1H), 8.89 (d, 1H), 7.65 (d, 1H), 7.59 (s, 1H), 7.18 (m, 1H), 6.99 (m, 1H), 6.86 (m, 2H), 4.88 (m, 1H), 3.60 (m, 1H), 3.05 (m, 1H), 1.90 (d, 3H). MS m/z 435.2 (M+H)⁺.

EXAMPLE 66

2-(3-hydroxypyridin-2-yl)-3-isopentyl-5-(trifluoromethyl)pyrido[4,3-d]pyrimidin-4(3H)-one

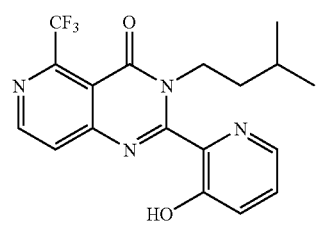

¹H NMR (400 MHz, dmso-d₆) δ 10.63 (s, 1H), 8.87 (d, 1H), 8.16 (m, 1H), 7.86 (d, 1H), 7.42 (m, 2H), 3.79 (t, 2H), 1.40-1.28 (m, 3H), 0.58 (d, 6H). MS m/z 379.2 (M+H)⁺.

EXAMPLE 67

2-(3-hydroxypyridin-2-yl)-3-((tetrahydro-2H-pyran-4-yl)methyl)-5-(trifluoromethyl)pyrido[4,3-d]pyrimidin-4(3H)-one

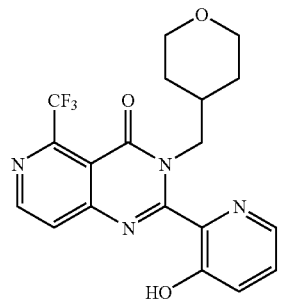

¹H NMR (400 MHz, dmso-d₆) δ 10.66 (s, 1H), 8.87 (d, 1H), 8.16 (dd, 1H), 7.86 (d, 1H), 7.42 (m, 2H), 3.79 (d, 2H), 3.64 (dd, 2H), 3.03 (dt, 2H), 1.76 (m, 1H), 1.24 (d, 2H), 0.94 (dq, 2H). MS m/z 407.3 (M+H)⁺.

EXAMPLE 68

2-(3-hydroxypyridin-2-yl)-3-(2-(tetrahydro-2H-pyran-4-yl)ethyl)-5-(trifluoromethyl)pyrido[4,3-d]pyrimidin-4(3H)-one

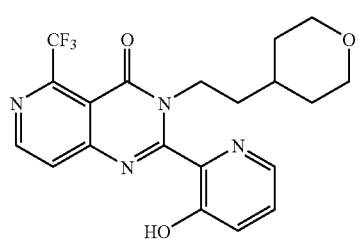

¹H NMR (400 MHz, dmso-d₆) 10.68 (s, 1H), 8.91 (d, 1H), 8.19 (dd, 1H), 7.80 (d, 1H), 7.47 (m, 2H), 3.86 (t, 2H), 3.66 (dd, 2H), 3.12 (t, 2H), 1.46 (q, 2H), 1.26 (m, 3H), 0.86 (dq, 2H). MS m/z 421.2 (M+H)⁺.

EXAMPLE 69

3-(2-fluoro-5-methoxyphenethyl)-2-(3-hydroxypyridin-2-yl)-5-(trifluoromethyl)pyrido[4,3-d]pyrimidin-4(3H)-one

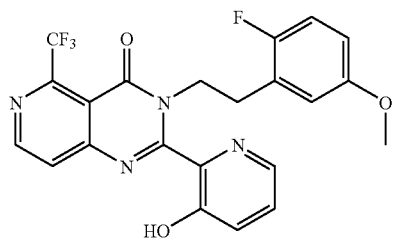

MS m/z 461 (M+H)⁺.

EXAMPLE 70

3-(2-fluoro-3-methoxyphenethyl)-2-(3-hydroxypyridin-2-yl)-5-(trifluoromethyl)pyrido[4,3-d]pyrimidin-4(3H)-one

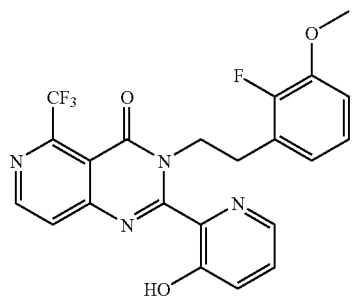

$^1$H NMR (400 MHz, CD$_3$OD) δ 8.90 (d, 1H), 8.20 (d, 1H), 7.89 (d, 1H), 7.56 (m, 2H), 6.90 (t, 1H), 6.76 (m, 1H), 6.56 (d, 1H), 4.30 (m, 2H), 3.64 (s, 3H), 2.99 (m, 2H). MS m/z 461.2 (M+H)$^+$.

EXAMPLE 71

2-(3-(2-fluorophenethyl)-4-oxo-5-(trifluoromethyl)-3,4-dihydroquinazolin-2-yl)benzonitrile

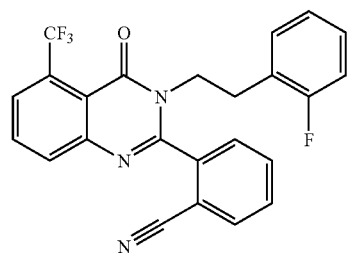

$^1$H NMR (400 MHz, CDCl$_3$) δ 7.68 (t, 1H), 7.64 (t, 1H), 7.25 (m, 6H), 7.14 (m, 1H), 7.01 (t, 1H), 6.96 (t, 1H), 4.32 (t, 2H), 3.06 (t, 2H). MS m/z 438.0 (M+H)$^+$.

EXAMPLE 72

N-(2-(3-(2-fluorophenethyl)-4-oxo-5-(trifluoromethyl)-3,4-dihydropyrido[4,3-d]pyrimidin-2-yl)pyridin-3-yl)-2,2,2-trifluoroacetamide

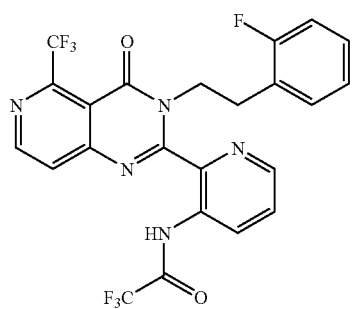

$^1$H NMR (400 MHz, CDCl$_3$) δ 11.45 (s, 1H), 9.99 (d, 1H), 8.79 (d, 1H), 8.55 (d, 1H), 7.76 (d, 1H), 7.50 (m, 1H), 7.15 (m, 1H), 6.90 (m, 1H), 6.70 (m, 1H), 4.99 (m, 2H), 3.05 (m, 2H). MS m/z 526.3 (M+H)$^+$.

EXAMPLE 73

(R)-2,2,2-trifluoro-N-(2-(4-oxo-3-(1-phenylpropan-2-yl)-5-(trifluoromethyl)-3,4-dihydropyrido[4,3-d]pyrimidin-2-VI)pyridin-3-VI)acetamide

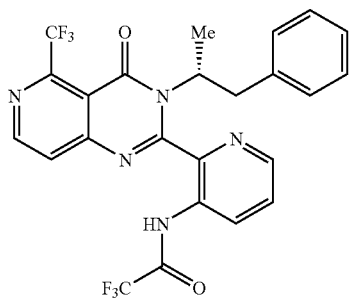

$^1$H NMR (400 MHz, CDCl$_3$) δ 10.65 (s, 1H), 9.99 (d, 1H), 8.79 (d, 1H), 8.60 (d, 1H), 7.66 (m, 1H), 7.44 (d, 1H), 7.00 (m, 2H), 6.79 (m, 2H), 4.69 (m, 1H), 3.70 (m, 1H), 2.95 (m, 1H), 2.01 (d, 3H). MS m/z 520.3 (M+H)$^+$.

EXAMPLE 74

3-cyclohexyl-2-(3-hydroxypyridin-2-yl)-5-(trifluoromethyl)pyrido[4,3-d]pyrimidin-4(3H)-one

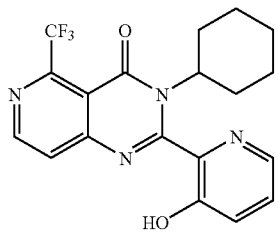

$^1$H NMR (400 MHz, CDCl$_3$) δ 8.99 (d, 1H), 8.25 (d, 1H), 7.77 (d, 1H), 7.43 (m, 2H), 4.80 (m, 1H), 2.65 (m, 2H), 1.50-1.25 (m, 8H). MS m/z 391.3 (M+H)$^+$.

EXAMPLE 75

3-(cyclohexylmethyl)-2-(3-hydroxypyridin-2-yl)-5-(trifluoromethyl)pyrido[4,3-d]pyrimidin-4(3H)-one

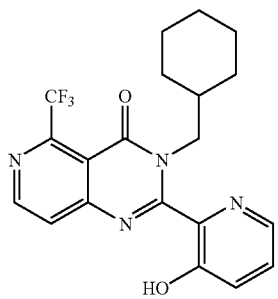

$^1$H NMR (400 MHz, CDCl$_3$) δ 12.39 (brs, 1H), 8.99 (d, 1H), 8.30 (d, 1H), 7.70 (d, 1H), 7.43 (m, 2H), 5.0 (brs, 2H), 1.50-1.25 (m, 10H). MS m/z 405.4 (M+H)$^+$.

EXAMPLE 76

3-Phenethyl-5-trifluoromethyl-2-(3-trifluoromethyl-pyridin-2-yl)-3H-pyrido[4,3-d]pyrimidin-4-one

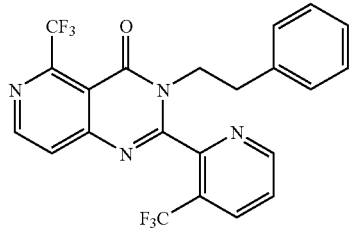

$^1$H NMR (400 MHz, CD$_3$OD) ☐ 9.02 (d, 1H); 8.91-8.92 (d, 1H); 8.25-8.27 (d, 1H); 7.78-7.79, (m, 2H); 7.22-7.23 (m, 3H); 7.0-7.02 (d, 2H); 3.95 (br, 2H), 3.10-3.14 (t, 2H). MS m/z 465.5 (M+H)$^+$.

EXAMPLE 77

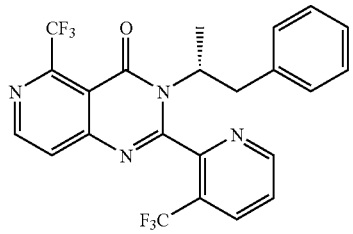

$^1$H NMR (400 MHz, CD$_3$OD) ☐ 8.88 (d, 1H); 8.87 (s, 1H); 8.22-8.24 (d, 1H); 7.73, 7.72, 7.69 (t, 2H); 7.20, 7.19 (d, 3H); 6.98, 6.96 (d, 2H); 3.88 (m, 1H); 3.64 (br, 1H); 3.36 (br, 1H); 1.59 (s, 3H); 1.55 (br, 1H). LC/MS 479.5 (M+H)$^+$.

EXAMPLE 78

2-(5-aminothiazol-4-yl)-3-phenethyl-5-(trifluoromethyl)pyrido[4,3-d]pyrimidin-4(3H)-one

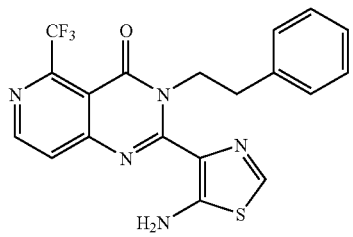

To a solution of 2-(5-(2,5-dimethyl-1H-pyrrol-1-yl)thiazol-4-yl)-3-phenethyl-5-(trifluoromethyl)pyrido[4,3-d]pyrimidin-4(3H)-one (7 mg, 0.014 mmol) in ethanol was added hydroxylamine hydrochloride (9.82 mg, 0.14 mmol) and the mixture was heated up to 80° C. for 60 hours. The reaction was then concentrated and purified with flash chromatography providing an off-white solid (1.5 mg). $^1$H NMR (400 MHz, CDCl$_3$) δ 8.72 (d, 1H), 8.02 (s, 1H), 7.52 (d, 1H), 7.30 (m, 5H), 6.93 (s, br, 2H), 4.89 (t, 2H), 3.17 (t, 2H). MS m/z 418.3 (M+H)$^+$.

EXAMPLE 79

2-(2-(difluoromethyl)phenyl)-3-phenethyl-5-(trifluoromethyl)pyrido[4,3-d]pyrimidin-4(3H)-one

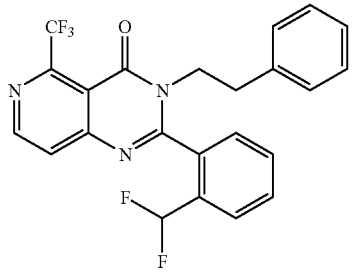

Prepared analogous to Example 1 starting from 2-(difluoromethyl)benzaldehyde and 4-Amino-N-phenethyl-2-(trifluoromethyl)nicotinamide. $^1$H NMR (400 MHz, CDCl$_3$) δ 8.88 (d, 1H), 7.77 (d, 1H), 7.72 (d, 1H), 7.69 (t, 1H), 7.61 (t, 1H), 7.19 (m, 4H), 6.89 (m, 2H), 6.77 (t, 1H), 4.28 (m, 1H), 3.78 (m, 1H), 2.95 (m, 2H). MS m/z 446.4 (M+H)$^+$.

EXAMPLE 80

2-(3-(difluoromethyl)pyridin-2-yl)-3-phenethyl-5-(trifluoromethyl)pyrido[4,3-d]pyrimidin-4(3H)-one

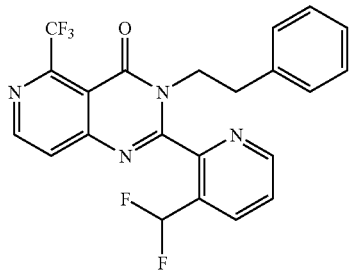

Prepared analogous to Example 1 starting from 2-(difluoromethyl)picolinaldehyde and 4-Amino-N-phenethyl-2-(trifluoromethyl)nicotinamide. $^1$H NMR (400 MHz, CDCl$_3$) δ 8.88 (d, 1H), 8.19 (d, 1H), 7.72 (d, 1H), 7.67 (m, 1H), 7.19 (m, 4H), 7.02 (m, 2H), 4.13 (m, 2H), 3.12 (m, 2H). MS m/z 447.5 (M+H)$^+$.

EXAMPLE 81

3-(2-cyclohexylethyl)-5-(trifluoromethyl)-2-(2-(trifluoromethyl)phenyl)pyrido[4,3-d]pyrimidin-

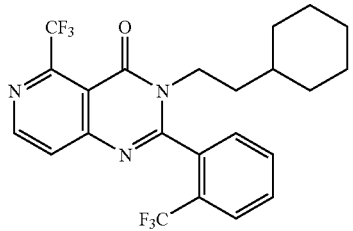

$^1$H NMR (500 MHz, CDCl$_3$) ☐ ppm 0.55-0.71 (m, 1H) 0.73-0.86 (m, 1H) 1.03-1.19 (m, 3H) 1.24-1.41 (m, 2H) 1.46-

1.67 (m, 5H) 1.68-1.83 (m, 1H) 3.38-3.52 (m, 1H) 4.07 –4.25 (m, 1H) 7.69-7.84 (m, 3H) 7.90 (d, 1H) 8.89 (d, 1H). MS m/z 470.5 (M+H)+.

EXAMPLE 82

3-(2-cyclohexylethyl)-5-(trifluoromethyl)-2-(3-(trifluoromethyl)pyridin-2-yl)pyrido[4,3-d]pyrimidin-4(3H)-one

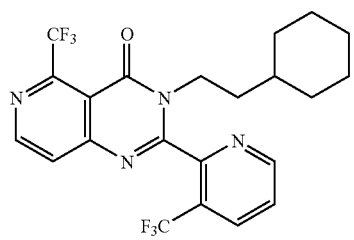

$^1$H NMR (500 MHz, CDCl$_3$) □ ppm 0.66-0.82 (m, 2H), 1.02-1.20 (m, 4H), 1.46 (d, 2H), (br. s., 2H), 7.72 (dd, 1H), 7.76 (d, 1H), 8.25 (d, 1H), 8.89 (d, 1H), 71.5 (M+H)+.

The following table provides FLIPR IC$_{50}$ data for the specified Examples. The IC$_{50}$s are reported as micromolar concentration with n being the number of times the particular compound was assayed.

Table of FLIPR assay data

| Example | n= | FLIPR IC$_{50}$ (uM) |
|---|---|---|
| 1 | 6 | 0.05 |
| 2 | 6 | 0.62 |
| 3 | 4 | 0.39 |
| 4a | 11 | 0.06 |
| 4b | 3 | 0.16 |
| 5 | 4 | 0.02 |
| 6 | 4 | 0.05 |
| 6a | 5 | 0.05 |
| 6b | 3 | 1.40 |
| 7 | 6 | 0.13 |
| 8 | 5 | 0.09 |
| 9 | 6 | 0.29 |
| 10 | 6 | 0.12 |
| 11 | 5 | 0.46 |
| 12 | 12 | 0.25 |
| 13 | 8 | 0.07 |
| 14 | 8 | 0.17 |
| 15 | 4 | 0.16 |
| 16 | 3 | 10.8 |
| 17 | 2 | 11.0 |
| 18 | 5 | 12.3 |
| 19 | 1 | >100 |
| 20 | 1 | >100 |
| 21 | 2 | 13.8 |
| 22 | 1 | >100 |
| 23 | 3 | 13.7 |
| 24 | 1 | 2.60 |
| 25 | 1 | 3.01 |
| 26 | 1 | 2.99 |
| 27 | 1 | 2.26 |
| 28 | 1 | 4.83 |
| 29 | 4 | 0.49 |
| 30 | 6 | 1.17 |
| 31 | 3 | 1.93 |
| 32 | 5 | 0.57 |
| 33 | 5 | 0.52 |
| 34 | 3 | 1.47 |
| 35 | 6 | 0.38 |
| 36 | 2 | 0.60 |
| 37a | 11 | .008 |
| 37b | 3 | 2.12 |
| 38a | 3 | 0.02 |
| 38b | 3 | 4.69 |
| 39 | 8 | 0.11 |
| 40 | 3 | 0.46 |
| 41 | 7 | 0.25 |
| 42 | 3 | 1.12 |
| 43 | 2 | 1.12 |
| 43a | 2 | 0.53 |
| 43b | 4 | 61.3 |
| 44 | 4 | 2.44 |
| 45 | 2 | 1.87 |
| 46 | 3 | 0.29 |
| 47 | 6 | 0.06 |
| 48a | 2 | 0.16 |
| 48b | 2 | 1.69 |
| 49 | 2 | 0.48 |
| 50 | 8 | 0.03 |
| 51 | 4 | 0.11 |
| 52 | 2 | 0.23 |
| 53 | 6 | 0.26 |
| 54 | 4 | 0.71 |
| 55 | 5 | 0.72 |
| 56 | 6 | 1.54 |
| 57 | 2 | 1.67 |
| 58 | 4 | 4.68 |
| 59 | 4 | 7.79 |
| 60 | 4 | 23.2 |
| 61 | 2 | 0.50 |
| 62 | 2 | 4.63 |
| 63 | 2 | 0.77 |
| 64 | 2 | 61.8 |
| 65 | 4 | 10.5 |
| 65a | 4 | 0.32 |
| 66 | 2 | 36.2 |
| 67 | 1 | >1.00 |
| 68 | 1 | >1.00 |
| 69 | 2 | 66.9 |
| 70 | 2 | 61.9 |
| 71 | 4 | 0.42 |
| 72 | 4 | 0.94 |
| 73 | 4 | 0.20 |
| 74 | 2 | 47.8 |
| 75 | 2 | 10000 |
| 76 | 3 | 6.30 |
| 77 | 7 | 0.70 |
| 78 | 2 | 9.83 |
| 79 | 3 | 0.39 |
| 80 | 2 | 0.30 |
| 81 | 2 | 7.89 |
| 82 | 2 | 2.53 |

All documents cited in this application, including scientific publications, patents and patent applications, are hereby incorporated by reference in their entirety.

What is claimed is:

1. A compound of formula I

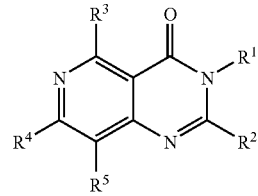

wherein $R^1$ is -Q or (C$_1$-C$_6$)alkyl-Q;

$R^2$ is pyridyl wherein said pyridyl is substituted with hydroxy and additionally is optionally substituted with one to three substituents independently selected from halo, cyano, trifluoromethyl, trifluoromethoxy, $(C_1-C_6)$alkyl, $(C_1-C_6)$alkoxy or hydroxy;

$R^3$ is hydrogen, $(C_1-C_6)$alkyl, $(C_3-C_7)$cycloalkyl, $(C_1-C_6)$alkyl-Q, aryl, heteroaryl, $OR^6$, or $NR^7R^8$; wherein said $(C_1-C_6)$alkyl, $(C_3-C_7)$cycloalkyl, aryl or heteroaryl is optionally substituted with one to three substituents independently selected from halo, cyano, trifluoromethyl, trifluoromethoxy, $(C_1-C_6)$alkyl; $(C_1-C_6)$alkoxy, $NR^7R^8$ or hydroxy;

$R^4$ and $R^5$ are each independently hydrogen, halo, cyano, $(C_1-C_6)$alkyl optionally substituted with one to three fluoro, aryl, heteroaryl, or $OR^6$;

$R^6$ at each occurrence is independently $(C_1-C_6)$alkyl, $(C_3-C_7)$cycloalkyl, $(C_3-C_7)$cycloalkyl-$(C_1-C_6)$alkyl, aryl, heteroaryl, $(C_1-C_6)$alkylaryl, or $(C_1-C_6)$alkylheteroaryl; each of said $(C_1-C_6)$alkyl, $(C_3-C_7)$cycloalkyl, $(C_3-C_7)$cycloalkyl-$(C_1-C_6)$alkyl, aryl, heteroaryl, $(C_1-C_6)$alkylaryl, or $(C_1-C_6)$alkylheteroaryl optionally substituted with one to three substituents independently selected from halo, hydroxy or $(C_1-C_3)$alkyl;

$R^7$ and $R^8$, at each occurrence, are independently hydrogen, $(C_1-C_6)$alkyl, or $(C_3-C_7)$cycloalkyl; or $R^7$ and $R^8$ taken together with the nitrogen to which they are attached form a 3 to 7 membered fully saturated ring optionally containing one to two additional heteroatoms independently selected from $N(R^9)_n$; O or $S(O)_p$;

n is 1;

p is 0, 1 or 2;

$R^9$ is hydrogen or $(C_1-C_6)$alkyl;

Q, at each occurrence, is independently aryl or heteroaryl; wherein said aryl or heteroaryl is optionally substituted with one to three substituents independently selected from halo, cyano, trifluoromethyl, trifluoromethoxy, $(C_1-C_6)$alkyl, $(C_1-C_6)$alkoxy or hydroxy;

or a pharmaceutically acceptable salt thereof.

2. The compound according to claim 1, wherein $R^2$ is pyridyl substituted with hydroxy and optionally substituted with one to three substituents independently selected from $(C_1-C_6)$alkoxy or halo; or a pharmaceutically acceptable salt thereof.

3. The compound according to claim 2, wherein $R^2$ is pyridyl substituted with hydroxy and optionally substituted with one to two substituents independently selected from $(C_1-C_6)$alkoxy or halo; or a pharmaceutically acceptable salt thereof.

4. The compound according to claim 1, wherein $R^2$ is pyridyl substituted with hydroxy and optionally substituted with one substituent selected from $(C_1-C_6)$alkoxy or halo; or a pharmaceutically acceptable salt thereof.

5. The compound according to claim 2, wherein $R^2$ is 3-hydroxy-pyridin-2-yl; wherein said 3-hydroxy-pyridin-2-yl is optionally substituted with one to two substituents independently selected from $(C_1-C_6)$alkoxy or fluoro; or a pharmaceutically acceptable salt thereof.

6. The compound according to claim 5, wherein $R^1$ is $(C_1-C_6)$alkyl-Q; and Q is phenyl optionally substituted with one or two fluoro; or a pharmaceutically acceptable salt thereof.

7. The compound according to claim 1, wherein $R^1$ is phenethyl or 1-methyl-2-(phenyl)ethyl, wherein said phenethyl or 1-methyl-2-(phenyl)ethyl is optionally substituted on phenyl with one or two halo; $R^2$ is 3-hydroxy-pyridin-2-yl, wherein said 3-hydroxy-pyridin-2-yl is optionally substituted with one or two substituents independently selected from $(C_1-C_3)$alkyl or halo; or a pharmaceutically acceptable salt thereof.

8. The compound according to claim 7 wherein $R^3$ is $(C_1-C_6)$alkyl, $(C_1-C_6)$alkyl-Q, aryl, heteroaryl, $OR^6$, or $NR^7R^8$, wherein said $(C_1-C_6)$alkyl, aryl or heteroaryl is optionally substituted with one to three substituents independently selected from halo, cyano, trifluoromethyl, trifluoromethoxy, $(C_1-C_6)$alkyl, $(C_1-C_6)$alkoxy, $NR^7R^8$ or hydroxy; and $R^4$ and $R^5$ are each hydrogen; or a pharmaceutically acceptable salt thereof.

9. The compound according to claim 8, wherein $R^3$ is trifluoromethyl; or a pharmaceutically acceptable salt thereof.

10. The compound according to claim 1, wherein $R^3$ is trifluoromethyl; or a pharmaceutically acceptable salt thereof.

11. The compound according to claim 10, wherein $R^4$ and $R^5$ are each independently hydrogen or methyl; or a pharmaceutically acceptable salt thereof.

12. The compound according to claim 11, wherein $R^2$ is hydroxy-pyridyl optionally substituted with one to three substituents independently selected from $(C_1-C_6)$alkoxy or halo; or a pharmaceutically acceptable salt thereof.

13. The compound according to claim 12, wherein $R^2$ is hydroxy-pyridyl; wherein said hydroxy-pyridyl is optionally substituted with one to two substituents independently selected from $(C_1-C_6)$alkoxy or fluoro; or a pharmaceutically acceptable salt thereof.

14. The compound according to claim 13, wherein $R^1$ is $(C_1-C_6)$alkyl-Q; and Q is phenyl optionally substituted with one or two substituents independently selected from fluoro, methyl or methoxy; or a pharmaceutically acceptable salt thereof.

15. The compound according to claim 11, wherein $R^1$ is phenethyl or 1-methyl-2-(phenyl)ethyl, wherein said phenethyl or 1-methyl-2-(phenyl)ethyl is optionally substituted on phenyl with one or two fluoro; or a pharmaceutically acceptable salt thereof.

16. The compound according to claim 11, wherein $R^2$ is 3-hydroxy-pyridin-2-yl, wherein said 3-hydroxy-pyridin-2-yl is optionally substituted with one or two substituents independently selected from $(C_1-C_3)$alkyl or halo; or a pharmaceutically acceptable salt thereof.

17. The compound according to claim 1 wherein $R^1$ is phenethyl or 1-methyl-2-(phenyl)ethyl, wherein said phenethyl or 1-methyl-2-(phenyl)ethyl is optionally substituted on phenyl with one or two substituents independently selected from halo or $(C_1-C_3)$alkyl or $(C_1-C_3)$alkoxy;

$R^2$ is 3-hydroxy-pyridin-2-yl, wherein said 3-hydroxy-pyridin-2-yl is optionally substituted with one or two substituents independently selected from $(C_1-C_3)$alkyl or halo;

$R^3$ is $(C_1-C_6)$alkyl, $(C_3-C_7)$cycloalkyl, $(C_1-C_6)$alkyl-Q, aryl, heteroaryl, or $OR^6$; wherein said $(C_1-C_6)$alkyl, $(C_3-C_7)$cycloalkyl, aryl or heteroaryl is optionally substituted with one to three substituents independently selected from fluoro, cyano, trifluoromethyl, trifluoromethoxy, $(C_1-C_3)$alkyl; $(C_1-C_3)$alkoxy, $NR^7R^8$ or hydroxy; and $R^4$ and $R^5$ are each independently hydrogen or methyl; or a pharmaceutically acceptable salt thereof.

18. A compound selected from the group consisting of:

2-(3-Hydroxy-pyridin-2-yl)-3-phenethyl-5-trifluoromethyl-3H-pyrido[4,3-d]pyrimidin-4-one;

(R)-2-(3-Hydroxy-pyridin-2-yl)-3-(1-methyl-2-phenylethyl)-5-trifluoromethyl-3H-pyrido[4,3-d]pyrimidin-4-one;

(R,S)-2-(3-Hydroxy-pyridin-2-yl)-3-(1-methyl-2-(2-fluorophenyl)ethyl)-5-trifluoromethyl-3H-pyrido[4,3-d]pyrimidin-4-one;

(R)-2-(3-Hydroxy-pyridin-2-yl)-3-(1-methyl-2-(2-fluorophenyl)ethyl)-5-trifluoromethyl-3H-pyrido[4,3-d]pyrimidin-4-one;

(S)-2-(3-Hydroxy-pyridin-2-yl)-3-(1-methyl-2-(2-fluorophenyl)ethyl)-5-trifluoromethyl-3H-pyrido[4,3-d]pyrimidin-4-one;

3-[2-(2-Fluoro-phenyl)-ethyl]-2-(3-hydroxy-pyridin-2-yl)-5-trifluoromethyl-3H-pyrido[4,3-d]pyrimidin-4-one;

3-[2-(3,4-Difluoro-phenyl)-ethyl]-2-(3-hydroxy-pyridin-2-yl)-5-trifluoromethyl-3H-pyrido[4,3-d]pyrimidin-4-one;

3-[2-(2,4-Difluoro-phenyl)-ethyl]-2-(3-hydroxy-pyridin-2-yl)-5-trifluoromethyl-3H-pyrido[4,3-d]pyrimidin-4-one;

3-[2-(3,4-Difluoro-phenyl)-ethyl]-2-(3-hydroxy-pyridin-2-yl)-5-trifluoromethyl-3H-pyrido[4,3-d]pyrimidin-4-one;

3-(1-(3,4-difluorophenyl) propan-2-yl)-2-(3-hydroxypyridin-2-yl)5-(trifluoromethyl)pyrido[4,3-d]pyrimidin-4(3H)-one;

(R)-3-(1-(3,4-difluorophenyl) propan-2-yl)-2-(3-hydroxy-pyridin-2-yl)5-(trifluoromethyl)pyrido[4,3-d]pyrimidin-4(3H)-one;

(S)-3-(1-(3,4-difluorophenyl) propan-2-yl)-2-(3-hydroxy-pyridin-2-yl)5-(trifluoromethyl)pyrido[4,3-d]pyrimidin-4(3H)-one;

3-(1-(2,4-difluorophenyl)propan-2-yl)-2-(3-hydroxypyridin-2-yl)-5-(trifluoromethyl)pyrido[4,3-d]pyrimidin-4(3H)-one;

3-(1-(2,4-difluorophenyl)propan-2-yl)-2-(3-hydroxypyridin-2-yl)-5-(trifluoromethyl)pyrido[4,3-d]pyrimidin-4(3H)-one;

3-(2-methoxyphenethyl)-2-(3-hydroxypyridin-2-yl)-5-(trifluoromethyl) pyrido[4,3-d]pyrimidin-4(3H)-one;

3-(2,3-difluorophenethyl)-2-(3-hydroxypyridin-2-yl)-5-(trifluoromethyl) pyrido[4,3-d]pyrimidin-4(3H)-one;

3-(5-fluoro-2-methoxyphenethyl)-2-(3-hydroxypyridin-2-yl)-5-(trifluoromethyl) pyrido[4,3-d]pyrimidin-4(3H)-one;

3-(2-fluoro-6-methoxyphenethyl)-2-(3-hydroxypyridin-2-yl)-5-(trifluoromethyl) pyrido[4,3-d]pyrimidin-4(3H)-one;

2-(3-hydroxypyridin-2-yl)-3-(1-(2-methoxyphenyl)propan-2-yl)-5-(trifluoromethyl)pyrido[4,3-d]pyrimidin-4(3H)-one;

2-(3-hydroxypyridin-2-yl)-3-(1-(2-methoxyphenyl)propan-2-yl)-5-(trifluoromethyl)pyrido[4,3-d]pyrimidin-4(3H)-one;

2-(3-hydroxypyridin-2-yl)-3-(1-(2-methoxyphenyl)propan-2-yl)-5-(trifluoromethyl)pyrido[4,3-d]pyrimidin-4(3H)-one;

3-(1-(2-fluorophenyl)butan-2-yl)-2-(3-hydroxypyridin-2-yl)-5-(trifluoromethyl) pyrido[4,3-d]pyrimidin-4(3H)-one;

3-(3-fluoro-2-methoxyphenethyl)-2-(3-hydroxypyridin-2-yl)-5-(trifluoromethyl) pyrido[4,3-d]pyrimidin-4(3H)-one;

3-(2-cyclopentylethyl)-2-(3-hydroxypyridin-2-yl)-5-(trifluoromethyl)pyrido[4,3-d]pyrimidin-4(3H)-one;

3-(2-cyclohexylethyl)-2-(3-hydroxypyridin-2-yl)-5-(trifluoromethyl)pyrido[4,3-d]pyrimidin-4(3H)-one;

(R)-3-(1-cyclohexylpropan-2-yl)-2-(3-hydroxypyridin-2-yl)-5-(trifluoromethyl) pyrido[4,3-d]pyrimidin-4(3H)-one;

(S)-3-(1-cyclohexylpropan-2-yl)-2-(3-hydroxypyridin-2-yl)-5-(trifluoromethyl) pyrido[4,3-d]pyrimidin-4(3H)-one;

(R,S)-2-(3-hydroxypyridin-2-yl)-3-(2-(tetrahydro-2H-pyran-2-yl)ethyl)-5-(trifluoromethyl)pyrido[4,3-d]pyrimidin-4(3H)-one;

N-(2-(3-(2-fluorophenethyl)-4-oxo-5-(trifluoromethyl)-3,4-dihydropyrido[4,3-d]pyrimidin-2-yl)pyridin-3-yl)acetamide;

2-(3-aminopyridin-2-yl)-3-phenethyl-5-(trifluoromethyl) pyrido[4,3-d]pyrimidin-4(3H)-one;

2-(3-hydroxypyridin-2-yl)-3-isopentyl-5-(trifluoromethyl)pyrido[4,3-d]pyrimidin-4(3H)-one;

2-(3-hydroxypyridin-2-yl)-3-((tetrahydro-2H-pyran-4-yl)methyl)-5-(trifluoromethyl)pyrido[4,3-d]pyrimidin-4(3H)-one;

2-(3-hydroxypyridin-2-yl)-3-(2-(tetrahydro-2H-pyran-4-yl)ethyl)-5-(trifluoromethyl)pyrido[4,3-d]pyrimidin-4(3H)-one;

3-(2-fluoro-5-methoxyphenethyl)-2-(3-hydroxypyridin-2-yl)-5-(trifluoromethyl)pyrido[4,3-d]pyrimidin-4(3H)-one;

3-(2-fluoro-3-methoxyphenethyl)-2-(3-hydroxypyridin-2-yl)-5-(trifluoromethyl)pyrido[4,3-d]pyrimidin-4(3H)-one;

N-(2-(3-(2-fluorophenethyl)-4-oxo-5-(trifluoromethyl)-3,4-dihydropyrido[4,3-d]pyrimidin-2-yl)pyridin-3-yl)-2,2,2-trifluoroacetamide;

(R)-2,2,2-trifluoro-N-(2-(4-oxo-3-(1-phenylpropan-2-yl)-5-(trifluoromethyl)-3,4-dihydropyrido[4,3-d]pyrimidin-2-yl)pyridin-3-yl)acetamide;

3-cyclohexyl-2-(3-hydroxypyridin-2-yl)-5-(trifluoromethyl)pyrido[4,3-d]pyrimidin-4(3H)-one;

3-(cyclohexylmethyl)-2-(3-hydroxypyridin-2-yl)-5-(trifluoromethyl)pyrido[4,3-d]pyrimidin-4(3H)-one;

3-Phenethyl-5-trifluoromethyl-2-(3-trifluoromethyl-pyridin-2-yl)-3H-pyrido[4,3-d]pyrimidin-4-one;

2-(3-(difluoromethyl)pyridin-2-yl)-3-phenethyl-5-(trifluoromethyl)pyrido[4,3-d]pyrimidin-4(3H)-one; and 3-(2-cyclohexylethyl)-5-(trifluoromethyl)-2-(3-(trifluoromethyl)pyridin-2-yl)pyrido[4,3-d]pyrimidin-4(3H)-one; or a pharmaceutically acceptable salt thereof.

19. The compound according to claim 1 which is (R)-3-(1-(3,4-difluorophenyl)propan-2-yl)-2-(3-hydroxypyridin-2-yl)5-(trifluoromethyl)pyrido [4,3-d]pyrimidin-4(3H)-one or (S)-3-(1-(3,4-difluorophenyl)propan-2-yl)-2-(3-hydroxypyridin-2-yl)5-(trifluoromethyl)pyrido[4,3-d]pyrimidin-4 (3H)-one or a pharmaceutically acceptable salt thereof.

20. The compound (R)-3-(1-(3,4-difluorophenyl) propan-2-yl)-2-(3-hydroxypyridin-2-yl)5-(trifluoromethyl)pyrido [4,3-d]pyrimidin-4(3H)-one or a pharmaceutically acceptable salt thereof.

21. A pharmaceutical composition comprising a therapeutically effective amount of a compound according to claim 1 or a pharmaceutically acceptable salt thereof and a pharmaceutically acceptable carrier, adjuvant or diluent.

22. The pharmaceutical composition of claim 21 wherein the compound is (R)-3-(1-(3,4-difluorophenyl)propan-2-yl)-2-(3-hydroxypyridin-2-yl)5-(trifluoromethyl)pyrido[4,3-d]pyrimidin-4(3H)-one or a pharmaceutically acceptable salt thereof.

* * * * *